(12) United States Patent
Griffiths et al.

(10) Patent No.: US 9,220,733 B2
(45) Date of Patent: Dec. 29, 2015

(54) SOLUBILIZATION OF ANTIGEN COMPONENTS FOR REMOVAL FROM TISSUES

(71) Applicant: THE REGENTS OF THE UNIVERSITY OF CALIFORNIA, Oakland, CA (US)

(72) Inventors: Leigh G. Griffiths, Davis, CA (US); Angeliki Papalamprou, Davis, CA (US); Maelene L. Wong, Woodland, CA (US)

(73) Assignee: The Regents of The University of California, Oakland, CA (US)

( * ) Notice: Subject to any disclaimer, the term of this patent is extended or adjusted under 35 U.S.C. 154(b) by 68 days.

(21) Appl. No.: 13/792,577

(22) Filed: Mar. 11, 2013

(65) Prior Publication Data

US 2013/0243738 A1    Sep. 19, 2013

Related U.S. Application Data

(60) Provisional application No. 61/612,964, filed on Mar. 19, 2012, provisional application No. 61/727,738, filed on Nov. 18, 2012.

(51) Int. Cl.
| | |
|---|---|
| *A61K 35/34* | (2015.01) |
| *A61L 27/36* | (2006.01) |
| *A61L 27/38* | (2006.01) |
| *C12N 5/077* | (2010.01) |

(52) U.S. Cl.
CPC ............. *A61K 35/34* (2013.01); *A61L 27/3633* (2013.01); *A61L 27/3687* (2013.01); *A61L 27/3804* (2013.01); *C12N 5/0657* (2013.01); *C12N 5/0658* (2013.01); *A61L 2430/40* (2013.01)

(58) Field of Classification Search
None
See application file for complete search history.

(56) References Cited

U.S. PATENT DOCUMENTS

2011/0008397 A1  1/2011  Cohen
2011/0236949 A1  9/2011  Orton

FOREIGN PATENT DOCUMENTS

WO    WO 2014/077934    5/2014

OTHER PUBLICATIONS

Griffiths et al, Biomaterials 2008, vol. 29, No. 26, pp. 3514-3520.*
Cordwell et al, Methods in Molecular Biology, 2008, vol. 424 pp. 139-146.*
International Search Report and Written Opinion dated Dec. 23, 2013 issued in PCT/US2013/57741.
Chang, et al. (2013) "Engineering Adult and Neonate Cardiac Myocardinal Patches" *NHLBI Conference on Cardiovascular Regenerative Medicine* Sep. 25-26, 2013, One Page.
Chung, et al. (2011) "Contribution of titin and extracellular matrix to passive pressure and measurement of sarcomere length in the mouse left ventricle" *Journal of Molecular and Cellular Cardiology*, 50: 731-739.
Filatov, et al. (2003) "Direct and indirect antibody-induced TX-100 resistance of cell surface antigens." *Immunology Letters* 85: 287-295.
Gillies, et al. (2011) "Structure and Function of the Skeletal Muscle Extracellular Matrix" *Muscle & Nerve*, 44: 318-331.
Gillies, et al. (2011) "Method for Decellularizing Skeletal Muscle Without Detergents or Proteolytic Enzymes" *Tissue Engineering: Part C*, 17(4): 383-389.
Nakashima, et al. (1979) "Comparison of structure and function of human erythrocyte and human muscle actin" *Proc. Natl. Acad. Sci. USA* 76(2): 935-938.
Papalamprou (2013) "Antigen Removal for the Production of Immunoacceptable Xenogenic Scaffolds for Myocardial Patch Tissue Engineering" presented to *Molecular, Cellular & Integrative Physiology (MCIP) Colloquium at University of California*, Davis on Mar. 1, 2013, 17 Pages.
Papalamprou, et al. (2013) "Antigen Removal for the Production of Immunoacceptable Xenogenic Scaffolds for Myocardial Patch Tissue Engineering" *Biomedical Engineering Society, 2013 annual meeting*: Sep. 25-28, 2013, One Page.
Petersen, et al. (2012) "Matrix composition and mechanics of decellularized lung scaffolds." *Cells Tissues Organs*. 195(3):222-31; Epub Apr. 18, 2011 [Abstract].
Soicher, et al. (2014) "Remineralized bone matrix as a scaffold for bone tissue engineering" *J Biomed Mater Res Part A*, 102A(12):4480-4490.
Spudich, et al. (1971) "The Regulation of Rabbit Skeletal Muscle Contraction." *J. Biol. Chem*. 246: 4866-4871.
Wong, et al. (2010) "Maintained Protein Solubility Enhances Antigen Removal from Xenogeneic Tissue for Heart Valve Tissue Engineering" *Tissue Engineering and Regenerative Medicine, International Society*, 2010 North America annual meeting: Dec. 5-8, 2010, One Page [Abstract].
Wong, et al. (2010) "Protein Solubilization for Antigen Removal from Bovine Pericardium in Heart Valve Tissue Engineering" *Biomedical Engineering Society*, 2010 annual meeting: Oct. 6-9, 2010, One Page [Abstract].
Wong, et al. (2011) "Antigen Removal Does Not Compromise Xenograft Properties or Correlate to Histological Acellularity" *Biomedical Engineering Society*, 2011 annual meeting: Oct. 12-15, 2011, One Page [Abstract].
Wong, et al. (2011) "Effect of Chaotropes on Antigen Removal in Xenogeneic Scaffold Generation" *Tissue Engineering and Regenerative Medicine, International Society*, 2011 North America annual meeting: Dec. 11-14, 2011, One Page [Abstract].

(Continued)

*Primary Examiner* — Allison Fox
(74) *Attorney, Agent, or Firm* — Weaver Austin Villeneuve & Sampson LLP

(57) ABSTRACT

The present invention relates to methods for removing antigens from tissues by sequentially destabilizing and/or depolymerizing cytoskeletal components and removing and/or reducing water-soluble antigens and lipid-soluble antigens. The invention further relates to tissue scaffolding and decellularized extracellular matrix produced by such methods.

35 Claims, 13 Drawing Sheets

(56) References Cited

OTHER PUBLICATIONS

Wong, et al. (2011) "Sequential, Differential Solubilization for Antigen Removal in Xenogeneic Scaffold Generation" *Tissue Engineering and Regenerative Medicine, International Society*, 2011 North America annual meeting: Dec. 11-14, 2011, One Page [Abstract].

Wong, et al. (2012) "Stepwise, Solubilization-Based Antigen Removal Maintains Xenogeneic Scaffold Properties" *Biomedical Engineering Society*, 2012 annual meeting: Oct. 24-27, 2012, One Page [Abstract].

Wong, et al. (2013) "Stepwise, Solubilization-Based Antigen Removal Maintains Xenogeneic Scaffold Recellularization Capacity" *Biomedical Engineering Society*, 2013 annual meeting: Sep. 25-28, 2013, One Page [Abstract].

Wong, et al. (2013) "Effect of stepwise, solubilization-based antigen removal on in vivo immune response to xenogeneic scaffolds" *Cellular and Molecular Bioengineering* 2013 Annual Conference: Jan. 2-5, 2013, One Page [Abstract].

Wong, et al. (2014) "Immunogenicity in xenogeneic scaffold generation: Antigen removal vs. decellularization" *Acta Biomaterialia* 10:1806-1816.

Wong, et al, "The role of protein solubilization in antigen removal from xenogeneic tissue for heart valve tissue engineering," Biomaterials 32 (2011) 8129-138.

Wong, et al., "Stepwise solubilization-based antigen removal for xenogeneic scaffold generation in tissue engineering," Acta Biomater. May 2013;9(5):6492-501.

* cited by examiner

SOLUBILIZATION OF ANTIGEN COMPONENTS FOR REMOVAL FROM TISSUES

CROSS-REFERENCE TO RELATED APPLICATIONS

This application claims the benefit under 35 U.S.C. §119 (e) of U.S. Provisional Application No. 61/612,964 filed on Mar. 19, 2012 and U.S. Provisional Application No. 61/727,738 filed on Nov. 18, 2012, both of which are hereby incorporated herein by reference in their entirety for all purposes.

FIELD

Provided are methods for removing antigens from tissues by sequentially removing and/or reducing water-soluble antigens and lipid-soluble antigens. Also provided are tissue scaffolding and decellularized extracellular matrix produced by such methods.

Further provided are methods for removing antigens from tissues by sequentially destabilizing and/or depolymerizing cytoskeletal components and removing and/or reducing water-soluble antigens and lipid-soluble antigens. Also provided are tissue scaffolding and decellularized extracellular matrix produced by such methods.

BACKGROUND

The ability of xenoantigens to elicit the immune response represents the critical barrier in the generation of scaffolds from xenogeneic tissues for tissue engineering and regenerative medicine applications (Platt, et al., *Circulation*. (2002) 106:1043-1047). Decellularization approaches were originally developed with the intention of addressing antigens in xenogeneic tissues. The decellularization paradigm attributes xenograft antigenicity to the cellular component of a tissue and uses the absence of cells by light microscopy as the principle determinant of success of the process. Implantation of decellularized porcine valve tissue into sheep, rats, and dogs showed little immunogenic response for up to one year, encouraging confidence in decellularization methods (Goldstein, et al., *Ann. Thorac. Surg.* (2000) 70:1962-1969; Iwai, et al., *J. Artificial Organs*. (2007) 10:29-35). Unfortunately, in vivo studies have reported the rapid failure of SynerGraft decellularized porcine heart valves following implantation into juvenile patients (Simon, et al, *Eur. J. Cardiothorac. Surg.* (2003) 23:1002-1006). Failure of the acellular SynerGraft prosthetic has been attributed to inadequate xenoantigen removal with decellularization (Simon, et al., supra). Foreign body type reaction and inflammatory cell infiltration into implanted SynerGraft valves has also been demonstrated (Simon, et al., supra; Sayk, et al., *Ann. Thorac. Surg.* (2005) 79:1755-1758). Additionally, persistent cellular debris following the SynerGraft decellularization process has been shown to be sufficient to elicit an immunogenic reaction and calcification (Schmidt, et al., *Biomaterials*. (2000) 21:2215-2231). Recent studies have indicated that acellularity on light microscopy does not equate to removal of known xenoantigens from the biomaterial (Goncalves, et al., *J. Heart Valve Dis.* (2005) 14:212-217; Meyer, et al., *J. Biomed. Mater. Res. A*. (2006) 79A:254-262; Wong, et al., *Acta Biomaterialia* (2013) epub ahead of print (doi: 10.1016/j.actbio.2012.12.034). We have shown the lack of correlation between residual nuclei counts in bovine pericardium (BP) and residual water-soluble protein (WSP) antigenicity of the biomaterial (Wong, et al., *Biomaterials* (2011) 32:8129-8138). Taken together, these results indicate that the fundamental principles behind the use of decellularization as the sole process necessary for xenogeneic scaffold generation and principal determinant of biomaterial antigenicity appear to be flawed. Thus, a void remains in the development of an antigen removal (AR) process to effectively reduce xenogeneic scaffold antigenicity.

A critical error in previous decellularization approaches was focusing merely on cell disruption without regard to the need for the antigenic molecules to be solubilized for efficient removal from the xenogeneic tissue. We have demonstrated previously that by promoting the solubilization of WSPs using a reducing agent and salt to prevent intermolecular aggregation and subsequent precipitation from solution, removal of WSP antigens from BP is significantly enhanced (Wong, et al., *Biomaterials*, supra). Our solubilization-based AR approach reduced the residual WSP antigenicity of BP by an additional 80% compared to hypotonic solution and 60% compared to 0.1% (w/v) sodium dodecyl sulfate (SDS) decellularization methods while maintaining biomaterial tensile properties and extracellular matrix (ECM) structure and composition (Wong, et al., *Biomaterials*, supra). However, by only promoting WSP solubilization for removal, lipid-soluble protein (LSP) antigens are likely to persist within the tissue. Thus, a means to encourage LSP solubilization for subsequent removal, following initial WSP solubilization, could reduce overall residual antigenicity in BP post-AR (BP-AR).

The concept of differential protein solubility has long been recognized in proteomics wherein a sequential, differential approach is used for the serial extraction of protein fractions from a homogenized tissue. Protein extraction methods exploit the physiochemical properties of proteins in order to differentially and sequentially extract various subsets of proteins for downstream analyses (Beers, et al., *Am. J. Physiol.* (1992) 262:L773-778; DuPont. *J. Agric. Food Chem.* (2005) 53:1575-1584; Cordwell, et al., *Methods Mol. Biol.* (2008) 424:139-146; Wilson, et al., *Matrix Biol.* (2008) 27:709-712). The use of a series of solutions to promote protein solubilization along a spectrum of solubilities (e.g., WSP extraction followed by LSP extraction) is critical for such sequential, differential extraction protocols, since proteins can only be extracted from the material into solutions in which they are soluble (Cordwell, et al., *Methods Mol. Biol.*, supra). However, the importance of promoting sequential, differential protein solubility during AR from intact tissues in the generation of xenogeneic scaffolds has not been investigated. This is a surprising oversight given the complex composition of protein antigens within a tissue requiring removal prior to implementation in tissue engineering applications.

The present invention is based, in part, on the discovery that a series of solutions, each promoting the solubilization and subsequent removal of a different subset of tissue proteins based on their solubility, enhances overall AR from BP. Furthermore, such a sequential, differential AR strategy significantly reduces BP antigenicity while maintaining biomaterial functional properties. In this study, several LSP solubilization promoting agents were applied as a second step of AR following initial WSP solubilization and assessed for their ability to reduce the residual LSP antigenicity of the resultant BP-AR. The effectiveness of this two-step sequential, differential strategy for reducing LSP antigens in BP was compared to a one-step AR strategy (WSP solubilization) (Wong, et al., *Biomaterials*, supra) and the literature gold standard (1% (w/v) SDS). See, Wong, et al., *Acta Biomaterialia* (2013) epub ahead of print (doi: 10.1016/j.actbio.2012.12.034). The effect of this two-step AR protocol on ECM mechanical properties, structure and composition of BP-AR was assessed by uniaxial tensile testing, histological analysis and biochemical quantification of ECM components, respectively.

Previously described myocardial tissue decellularization methods have also been solely based on the ubiquitous use of harsh denaturing detergents, mainly SDS, in concentrations as high as 2% in hypotonic water solutions. See, Elder, et al., *Biomaterials*. (2009) 30(22): 3749-3756. Although effective in solubilizing cellular and tissue components, it has been shown that these methods are not successful in removing antigenic determinants, while they are often detrimental to the extracellular matrix (removing elastin, glycosaminoglycans and damaging collagen structure). Further, commonly utilized detergents are toxic to repopulating cells reducing the chances of successful recellularization strategies for the produced scaffolds.

Reported methods to produce a myocardial scaffold have been based on detergent-based decellularization methods. More specifically, these approaches included the use of one detergent (SDS, Triton-X100, Saponin) with protease inhibitors (to prevent extracellular matrix protein degradation) and occasionally enzymatic treatments (such as trypsin) and nucleases for nucleic acid degradation in different concentrations and combinations. All these reports determine loss of nuclei and cellular components and production of an acellular scaffold as their outcome measure for protocol success. As we have already shown in our laboratory this assumption is not valid, since antigens may be associated with non-cellular components of the tissue. Additionally, the omission of a reducing agent in all these treatments would be expected to result in protein precipitation rather than solubilization and extraction, regardless of the concentration of the detergent used.

SUMMARY

The present invention relates to methods for removing antigen components from tissue, e.g., to create a tissue scaffolding and/or a substantially decellularized extracellular matrix, e.g., for use in tissue transplantation, tissue regeneration, and/or model matrices for study of cellular/ECM interactions. In various embodiments, the tissue is an intact tissue. As appropriate, the tissue may be a part of an organ or an intact organ. Generally, the methods are performed in vitro.

In various embodiments, the methods comprise sequentially solubilizing and removing water soluble antigen components and solubilizing and removing lipid-soluble antigen components. In various embodiments, the water-soluble antigen components are first solubilized and removed from the tissue, and then the lipid-soluble antigen components are subsequently solubilized and removed from the tissue. In various embodiments, the lipid-soluble antigen components are first solubilized and removed from the tissue, and then the water-soluble antigen components are subsequently solubilized and removed from the tissue.

In various embodiments, the methods comprise sequentially, destabilizing and/or depolymerizing cytoskeletal components (e.g., filamentous actin and/or microtubules) to solubilize the macromolecular structure of the cellular cytoskeleton and thereby facilitate solubilization and removal of those water-soluble antigen components and lipid-soluble antigen components which are associated with the cytoskeleton In various embodiments, the tissue is first contacted with a solution comprising one or more cytoskeletal destabilizing and/or depolymerizing agents. In various embodiments, the water-soluble antigen components are solubilized and removed from the tissue, and then the lipid-soluble antigen components are subsequently solubilized and removed from the tissue. In various embodiments, the lipid-soluble antigen components are solubilized and removed from the tissue, and then the water-soluble antigen components are subsequently solubilized and removed from the tissue.

Accordingly, in one aspect, the invention provides methods of removing immunogenic antigens from a tissue. In some embodiments, the methods comprise:
 a) solubilizing water-soluble antigens in the tissue;
 b) separating the tissue from the solubilized water-soluble antigens;
 c) solubilizing lipid-soluble antigens in the tissue; and
 d) separating the tissue from the solubilized lipid-soluble antigens; thereby removing immunogenic antigens from the tissue.

In one aspect, the invention provides methods for removing immunogenic antigens from a tissue. In some embodiments, the methods comprise:
 a) contacting the tissue with one or more cytoskeletal destabilizing and/or depolymerizing agents;
 b) solubilizing water-soluble antigens in the tissue;
 c) separating the tissue from the solubilized water-soluble antigens;
 d) solubilizing lipid-soluble antigens in the tissue; and
 e) separating the tissue from the solubilized lipid-soluble antigens; thereby removing immunogenic antigens from the tissue. In various embodiments, a wash or rinse step is performed after step a), separating the tissue from the one or more cytoskeletal destabilizing agents and destabilized and/or depolymerized cytoskeletal proteins and associated antigens. In varying embodiments, the steps of the method are performed in the order set forth above. In varying embodiments, one or more of the steps are repeated, e.g., one, two, three or more times, as appropriate or desired.

In a related aspect, the invention provides methods for removing immunogenic antigens from a muscle tissue, comprising:
 a) relaxing the muscle tissue in a relaxing solution comprising an energy source molecule or other molecule to dissociate actin-myosin crossbridges;
 b) contacting the muscle tissue with one or more cytoskeletal destabilizing and/or depolymerizing agents;
 c) contacting the muscle tissue with a concentrated salt solution;
 d) solubilizing water-soluble antigens in the tissue;
 e) separating the muscle tissue from the solubilized water-soluble antigens;
 f) solubilizing lipid-soluble antigens in the tissue; and
 g) separating the muscle tissue from the solubilized lipid-soluble antigens; thereby removing immunogenic antigens from the muscle tissue. In various embodiments, a wash or rinse step is performed after step a), separating the tissue from the relaxing solution. In various embodiments, a wash or rinse step is performed after step b), separating the tissue from the one or more cytoskeletal destabilizing agents and destabilized and/or depolymerized cytoskeletal proteins. In various embodiments, a wash or rinse step is performed after step c), separating the tissue from the concentrated salt solution and solubilized sarcomeric components. In varying embodiments, the steps of the method are performed in the order set forth above. In varying embodiments, the steps for removing immunogenic antigens from a muscle tissue are performed in the following order: a), b), c), d), e), f) and g). In varying embodiments, the steps for removing immunogenic antigens from a muscle tissue are performed in the following order: a), f), g), b), c), d) and e). In varying embodiments, the steps for removing immunogenic antigens from a muscle tissue are performed in the following order: a), d), e), b), c), f) and g). In varying embodiments, the steps for removing immunogenic antigens from a muscle tissue are performed in the following order: a), d), e), f), g), b) and c). In varying embodiments, one or more of the steps are repeated, e.g., one, two, three or more times, as appropriate or desired. For example, in some embodiments, steps b), c), d) and e) are repeated one or more times. In varying embodiments, the steps for removing immunogenic antigens from a muscle tissue are performed in the following order: a), b), c), d), e), f), g), b), c), and e). In varying embodiments, the steps for removing immunogenic antigens from a muscle tissue are performed in the following order: a), f), g), b), c), d), e), f), and g).

In varying embodiments of the methods, the lipid-soluble antigens are solubilized and separated first, and then the water-soluble antigens are solubilized and separated. In varying embodiments, the water-soluble antigens are solubilized and separated first, and then the lipid-soluble antigens are solubilized and separated. In varying embodiments, the tissue is contacted with one or more one or more cytoskeletal destabilizing and/or depolymerizing agents concurrently with the solubilization and separation of water soluble antigens.

With respect to further embodiments of the methods, in some embodiments, the immunogenic antigens are selected from the group consisting of protein antigens, lipid antigens and carbohydrate antigens. In some embodiments, the method does not comprise contacting the tissue with a detergent selected from the group consisting of sodium dodecyl sulfate, Triton-X-100, Triton-X-114, Triton-X-200 and sodium deoxycholate. In some embodiments, the method does not comprise contacting the tissue with a protease, for example, trypsin.

In some embodiments, the one or more cytoskeletal destabilizing agents comprise one or more actin depolymerization agents. In some embodiments, the one or more actin depolymerization agents are selected from the group consisting of Cytochalasin A, Cytochalasin B, Cytochalasin C, Cytochalasin D, Cytochalasin E, Cytochalasin F, Cytochalasin G, Cytochalasin H, Cytochalasin I, Cytochalasin J, Latrunculin A, Latrunculin B, Swinholide A, Misakinolide A, Bistheonelide A, Scytophycin A, Scytophycin B, Scytophycin D, Scytophycin E, 19-O-Demethylscytophycin C, 6-Hydroxyscytophycin B, 6-Hydroxy-7-o-methylscytophycin E and tolytoxin, Mycalolide A, Mycalolide B, Mycalolide C, seco-mycalolide A and 30-hydroxymycalolide A, Halichondramide, (19Z)-halichondramide, kabiramides B, kabiramides C, kabiramides D, kabiramides G, kabiramides J, kabiramides K, ulapualide A, jaspamide, Dihydrohalichondramide, Aplyronine A, Aplyronine B, Aplyronine C, Pectenotoxin 2, Pectenotoxin 6, and Migrastatin. In some embodiments, the actin depolymerization agents depolymerize filamentous cytoskeletal actin (F-actin). In some embodiments, the actin depolymerization agents depolymerize filamentous α-sarcomeric actin (F-actin).

In some embodiments, the one or more cytoskeletal destabilizing agents comprise one or more microtubule depolymerization or destabilizing agents. In some embodiments, the one or more microtubule depolymerization or destabilizing agents is selected from the group consisting of colchicine, colcemid, vinblastine, vincristine, myoseverin, nocodazole, podophyllotoxin, polygamain and taxol.

In some embodiments, the water-soluble antigens are solubilized in a solution comprising a buffering agent, a reducing agent, a protease inhibitor, and one or more salts suitable for maintaining protein solubility. In some embodiments, the buffering agent maintains a pH in the range of about 4-11, e.g., a pH in the range of about 4-6, 8-11, 5-10 or 6-9. In some embodiments, the buffering agent maintains a pH of at least about 8. In some embodiments, the one or more salts comprise a monovalent or a divalent anion. In some embodiments, the one or more salts comprise a metal halide salt. In some embodiments, the metal halide salt is selected from the group consisting of LiF, LiCl, LiBr, LiI, NaF, NaCl, NaBr, NaI, KF, KCl, KBr, KI, RbF, RbCl, RbBr, RbI, CsF, CsCl, CsBr, CsI, $BeF_2$, $BeCl_2$, $BeBr_2$, $BeI_2$, $MgF_2$, $MgCl_2$, $MgBr_2$, $MgI_2$, $CaF_2$, $CaCl_2$, $CaBr_2$, $CaI_2$, $SrF_2$, $SrCl_2$, $SrBr_2$, $SrI_2$, $BaF_2$, $BaCl_2$, $BaBr_2$, $BaI_2$, and mixtures thereof. In some embodiments, the reducing agent is selected from the group consisting of Tributylphosphine (TBP), beta mercaptoethanol, 2-mercaptoethylamine, tris(2-carboxyethyl)phosphine (TCEP), cysteine-HCl, and dithiothreitol (DTT). In some embodiments, the water-soluble antigens are solubilized in a solution that comprises one or more of an antibacterial agent and/or an antifungal agent. In some embodiments, the water-soluble antigens are solubilized in a solution that comprises a chelation agent. In some embodiments, the chelation agent is selected from the group consisting of ethylenediaminetetraacetic acid (EDTA), diethylenetriaminepentaacetic acid (DTPA), Citric Acid, N,N-bis(carboxymethyl)glycine (NTA), and the meso isomer of Dimercaptosuccinic acid (DMSA). In some embodiments, the water-soluble antigens are solubilized in a solution that does not comprise an amphiphile. In some embodiments, the water-soluble antigens are solubilized in a solution that does not comprise a detergent. In some embodiments, the water-soluble antigens are solubilized in a solution that comprises a non-detergent sulfobetaine. In some embodiments, the water-soluble antigens are solubilized in a solution comprising Tris-HCl, dithiothreitol (DTT), a protease inhibitor, and KCl.

In some embodiments, the lipid-soluble antigens are solubilized in a solution comprising a buffering agent, a reducing agent, a protease inhibitor, one or more salts suitable for maintaining protein solubility and an amphiphile. In some embodiments, the amphiphile is a zwitterionic detergent. In some embodiments, the amphiphile is a sulfobetaine. In some embodiments, the sulfobetaine is selected from the group consisting of 3-[N,N-Dimethyl(3-myristoylaminopropyl) ammonio]propanesulfonate (amidosulfobetaine-14; ASB-14); amidosulfobetaine-16 (ASB-16); 4-n-Octylbenzoylamido-propyl-dimethylammonio sulfobetaine (ASB-C8Ø); 3-(N,N-Dimethyloctylammonio) propanesulfonate inner salt (SB 3-8); N-Decyl-N,N-dimethyl-3-ammonio-1-propanesulfonate (SB 3-10), N-Decyl-N,N-dimethyl-3-ammonio-1-propanesulfonate (SB 3-12), N-Tetradecyl-N,N-dimethyl-3-ammonio-1-propanesulfonate (SB 3-14); 3-(N,N-Dimethylpalmitylammonio) propanesulfonate (SB3-16); 3-(N,N-Dimethyloctadecylammonio) propanesulfonate (SB3-18); 3-(1-Pyridinio)-1-propanesulfonate (NDSB-201); 3-(Benzyldimethylammonio) propanesulfonate (NDSB-256); NDSB-211, NDSB-195, NDSB-221; 3-[(3-Cholamidopropyl)dimethylammonio]-1-propanesulfonate (CHAPS), 3-[(3-Cholamidopropyl)dimethylammonio]-2-hydroxy-1-propanesulfonate (CHAPSO), and mixtures thereof. In some embodiments, the lipid-soluble antigens are solubilized in a solution comprising Tris-HCl, dithiothreitol (DTT), a protease inhibitor, KCl and ASB-14.

In some embodiments, the method yields a substantially intact extracellular matrix (ECM) compatible with viable cell repopulation. In some embodiments, the methods further comprise repopulating the ECM with live cells. In some embodiments, the live cells are autologous, allogeneic or xenogeneic to the ECM. In some embodiments, the live cells comprise mesenchymal stem cells. In some embodiments, the live cells comprise cells of the same tissue type as the tissue from which the antigens are removed.

In some embodiments, the tissue is epithelial tissue, endothelial tissue, muscle tissue, or connective tissue. In some embodiments, the tissue is selected from the group consisting of cardiac muscle tissue, striated or skeletal muscle tissue, or smooth muscle tissue, heart, pericardium, heart valve, vessel, vascular conduit, artery, vein, skin, dermis, pericardium, dura, intestinal submucosa, ligament, tendon, bone, cartilage, ureter, urinary bladder, kidney, skin, lung, liver, and umbilical cord. In some embodiments, the tissue is an intact tissue. In some embodiments, the tissue is within or a part of an intact organ. In some embodiments, at least about 80%, for example, at least about 85%, 90%, 93%, 95%, 97%, 99%, or more, of the water soluble antigens are removed from the tissue. In some embodiments, at least about 60%, for example, at least about 65%, 70%, 75%, 80%, 85%, 90%, 93%, 95%, 97%, 99%, or more, of the lipid soluble antigens are removed from the tissue.

In some embodiments, the tissue is muscle tissue. In some embodiments, the muscle tissue is cardiac muscle tissue, striated or skeletal muscle tissue, or smooth muscle tissue. In some embodiments, the method comprises the step of relaxing the muscle tissue prior to contacting the tissue with one or more cytoskeletal destabilizing agents. In some embodiments, the muscle tissue is relaxed in a relaxing solution comprising an energy source molecule or other actin-myosin dissociation agent. In some embodiments, the energy source molecule is selected from the group consisting of a nucleotide 5'-triphosphate (NTP), adenosine, inosine, aspartate, glutamate, creatine phosphate, a Kreb's cycle precursor or intermediate, glucose, and dextrose. In some embodiments, the energy source molecule is pyrophosphate (PPi) or a nucleotide 5'-triphosphate (NTP) selected from the group consisting of adenosine 5'-triphosphate (ATP), inosine 5'-triphosphate (ITP), guanidine 5'-triphosphate (GTP), cytidine 5'-triphosphate (CTP), and uridine 5'-triphosphate (UTP). In some embodiments, the energy source molecule is a precursor of adenosine 5'-triphosphate (ATP). In some embodiments, the energy source molecule is adenosine 5'-triphosphate (ATP). In some embodiments, the energy source molecule is Pyrophosphate (PPi). In some embodiments, the energy source molecule comprises vanadate and adenosine 5'-diphosphate (ADP). In some embodiments, the relaxing solution further comprises a calcium ion chelating agent. In some embodiments, the relaxing solution further comprises a permeabilization agent. In some embodiments, the muscle tissue is contacted with a concentrated salt solution. In some embodiments, the concentrated salt solution comprises one or more salts in a concentration range from about 0.5 M to about 3.0 M, e.g., about 0.6 M, 0.7 M, 0.8 M, 0.9 M, 1.0 M, 1.1 M, 1.2 M, 1.3 M, 1.4 M, 1.5 M, 1.6 M, 1.7 M, 1.8 M, 1.9 M, 2.0 M, 2.1 M, 2.2 M, 2.3 M, 2.4 M, 2.5 M, 2.6 M, 2.7 M, 2.8 M, 2.9 M, or 3.0 M. In some embodiments, the concentrated salt solution comprises one or more metal halide salts. In some embodiments, the metal halide salt is selected from the group consisting of LiF, LiCl, LiBr, LiI, NaF, NaCl, NaBr, NaI, KF, KCl, KBr, KI, RbF, RbCl, RbBr, RbI, CsF, CsCl, CsBr, CsI, $BeF_2$, $BeCl_2$, $BeBr_2$, $BeI_2$, $MgF_2$, $MgCl_2$, $MgBr_2$, $MgI_2$, $CaF_2$, $CaCl_2$, $CaBr_2$, $CaI_2$, $SrF_2$, $SrCl_2$, $SrBr_2$, $SrI_2$, $BaF_2$, $BaCl_2$, $BaBr_2$, $BaI_2$, and mixtures thereof. In some embodiments, the concentrated salt solution comprises KCl and KI.

In some embodiments, the concentrated salt solution comprises 0.6 M KCl and 1.0 M KI. In some embodiments, sarcomeric constituents are not detectable in the muscle tissue. In some embodiments, at least about 90% of the sarcomeric constituents are removed, e.g., at least about 93%, 95%, 97%, 98%, 99% or all (100%) sarcomeric constituents are removed.

In a further aspect, the invention provides tissue scaffolds produced by the methods described above and herein. In another aspect, the invention provides kits comprising a tissue scaffold produced by the methods described above and herein. In a related aspect, the invention provides decellularized extracellular matrix (ECM) produced by the methods described above and herein. In varying embodiments, the ECM and/or tissue scaffolds are free of residual sodium dodecyl sulfate. In varying embodiments, the ECM and/or tissue scaffolds induce little or no immune response in a host that is xenogeneic or allogeneic to the ECM. In some embodiments, the ECM and/or tissue scaffolds do not comprise detectable sarcomeric consituents. In varying embodiments, the ECM comprises ECM structure, ECM biochemical composition and ECM tensile strength that is substantially the same as the ECM prior to decellularization, wherein the ECM is compatible with viable cell repopulation, and is substantially free of endogenous antigens.

In another aspect, the invention provides kits comprising (i) a solution for solubilizing water-soluble antigens and (ii) a solution for solubilizing lipid-soluble antigens. In a further aspect, the invention provides kits comprising (i) a solution for destabilizing cytoskeletal polymers, (ii) a solution for solubilizing water soluble antigens and (iii) a solution for solubilizing lipid soluble antigens. Further embodiments, of the solution for solubilizing water-soluble antigens and of the solution for solubilizing lipid-soluble antigens are as described herein. In some embodiments, the kits further comprise a control tissue scaffold and/or a decellularized extracellular matrix (ECM) produced by the methods described herein.

With respect to embodiments of the kits, in some embodiments, the solution for destabilizing cytoskeletal polymers comprises one or more actin depolymerization agents. In some embodiments, the one or more actin depolymerization agents are selected from the group consisting of Cytochalasin A, Cytochalasin B, Cytochalasin C, Cytochalasin D, Cytochalasin E, Cytochalasin F, Cytochalasin G, Cytochalasin H, Cytochalasin I, Cytochalasin J, Latrunculin A, Latrunculin B, Swinholide A, Misakinolide A, Bistheonelide A, Scytophycin A, Scytophycin B, Scytophycin D, Scytophycin E, 19-O-Demethylscytophycin C, 6-Hydroxyscytophycin B, 6-Hydroxy-7-o-methylscytophycin E and tolytoxin, Mycalolide A, Mycalolide B, Mycalolide C, secomycalolide A and 30-hydroxymycalolide A, Halichondramide, (19Z)-halichondramide, kabiramides B, kabiramides C, kabiramides D, kabiramides G, kabiramides J, kabiramides K, ulapualide A, jaspamide, Dihydrohalichondramide, Aplyronine A, Aplyronine B, Aplyronine C, Pectenotoxin 2, Pectenotoxin 6, and Migrastatin. In some embodiments, the actin depolymerization agents depolymerize filamentous cytoskeletal actin. In some embodiments, the actin depolymerization agents depolymerize α-sarcomeric actin (F-actin). In some embodiments, the solution for destabilizing cytoskeletal polymers comprises one or more microtubule depolymerization or destabilizing agents. In some embodiments, the one or more microtubule depolymerization or destabilizing agents is selected from the group consisting of colchicine, colcemid, vinblastine, vincristine, myoseverin, nocodazole, podophyllotoxin, polygamain and taxol.

In some embodiments, the solution for solubilizing water soluble antigens comprises a buffering agent, a reducing agent, a protease inhibitor, and one or more salts suitable for maintaining protein solubility. In some embodiments, the buffering agent maintains a pH in the range of about 4-11, e.g., a pH in the range of about 4-6, 8-11, 5-10 or 6-9. In some embodiments, the buffering agent maintains a pH of at least about 8. In some embodiments, the one or more salts comprise a monovalent or a divalent anion. In some embodiments, the one or more salts comprise a metal halide salt. In some embodiments, the metal halide salt is selected from the group consisting of LiF, LiCl, LiBr, LiI, NaF, NaCl, NaBr, NaI, KF, KCl, KBr, KI, RbF, RbCl, RbBr, RbI, CsF, CsCl, CsBr, CsI, $BeF_2$, $BeCl_2$, $BeBr_2$, $BeI_2$, $MgF_2$, $MgCl_2$, $MgBr_2$, $MgI_2$, $CaF_2$, $CaCl_2$, $CaBr_2$, $CaI_2$, $SrF_2$, $SrCl_2$, $SrBr_2$, $SrI_2$, $BaF_2$, $BaCl_2$, $BaBr_2$, $BaI_2$, and mixtures thereof. In some embodiments, the reducing agent is selected from the group consisting of Tributylphosphine (TBP), beta mercaptoethanol, 2-mercaptoethylamine, tris(2-carboxyethyl)phosphine (TCEP), cysteine-HCl, and dithiothreitol (DTT). In some embodiments, the solution for solubilizing water soluble antigens comprises one or more of an antibacterial agent and/or an antifungal agent. In some embodiments, the solution for solubilizing water soluble antigens comprises a chelation agent. In some embodiments, the chelation agent is selected from the group consisting of ethylenediaminetetraacetic acid (EDTA), diethylenetriaminepentaacetic acid (DTPA), Citric Acid, N,N-bis(carboxymethyl)glycine (NTA), and the meso isomer of Dimercaptosuccinic acid (DMSA). In some embodiments, the solution for solubilizing water soluble antigens does not comprise an amphiphile. In some embodiments, the solution for solubilizing water soluble antigens does not comprise a detergent. In some embodiments, the solution for solubilizing water soluble antigens comprises a non-detergent sulfobetaine. In some embodiments, the solution for solubilizing water soluble antigens comprises Tris-HCl, dithiothreitol (DTT), a protease inhibitor, and KCl.

In some embodiments, the solution for solubilizing lipid soluble antigens comprises a buffering agent for maintaining pH of at least 8.0, a reducing agent, a protease inhibitor, one or more salts suitable for maintaining protein solubility and an amphiphile. In some embodiments, the amphiphile is a zwitterionic detergent. In some embodiments, the amphiphile is a sulfobetaine. In some embodiments, the sulfobetaine is selected from the group consisting of 3-[N,N-Dimethyl(3-myristoylaminopropyl)ammonio]propanesulfonate (amidosulfobetaine-14; ASB-14); amidosulfobetaine-16 (ASB-16); 4-n-Octylbenzoylamido-propyl-dimethylammonio sulfobetaine (ASB-C8Ø); 3-(N,N-Dimethyloctylammonio) propanesulfonate inner salt (SB3-8); N-Decyl-N,N-dimethyl-3-ammonio-1-propanesulfonate (SB 3-10), N-Decyl-N,N-dimethyl-3-ammonio-1-propanesulfonate (SB 3-12), N-Tetradecyl-N,N-dimethyl-3-ammonio-1-propane-sulfonate (SB 3-14); 3-(N,N-Dimethylpalmitylammonio) propanesulfonate (SB3-16); 3-(N,N-Dimethyloctadecylammonio) propanesulfonate (SB3-18); 3-(1-Pyridinio)-1-propanesulfonate (NDSB-201); 3-(Benzyldimethylammonio) propanesulfonate (NDSB-256); NDSB-211, NDSB-195, NDSB-221; 3-[(3-Cholamidopropyl)dimethylammonio]-1-propanesulfonate (CHAPS), 3-[(3-Cholamidopropyl)dimethylammonio]-2-hydroxy-1-propanesulfonate (CHAPSO), and mixtures thereof. In some embodiments, the lipid-soluble antigens are solubilized in a solution comprising Tris-HCl, dithiothreitol (DTT), a protease inhibitor, KCl and ASB-14.

In some embodiments, the kits further comprise (iv) a relaxing solution comprising an energy source molecule. In some embodiments, the energy source molecule is selected from the group consisting of a nucleotide 5'-triphosphate (NTP), adenosine, inosine, aspartate, glutamate, creatine phosphate, a Kreb's cycle precursor or intermediate, glucose, and dextrose. In some embodiments, the energy source molecule is pyrophosphate (PPi) or a nucleotide 5'-triphosphate (NTP) selected from the group consisting of adenosine 5'-triphosphate (ATP), inosine 5'-triphosphate (ITP), guanidine 5'-triphosphate (GTP), cytidine 5'-triphosphate (CTP), and uridine 5'-triphosphate (UTP). In some embodiments, the energy source molecule is a precursor of adenosine 5'-triphosphate (ATP). In some embodiments, the energy source molecule is adenosine 5'-triphosphate (ATP). In some embodiments, the energy source molecule is Pyrophosphate (PPi). In some embodiments, the energy source molecule comprises vanadate and adenosine 5'-diphosphate (ADP). In some embodiments, the relaxing solution further comprises a calcium ion chelating agent. In some embodiments, the energy source molecule is a precursor of adenosine 5'-triphosphate (ATP). In some embodiments, the relaxing solution further comprises a permeabilization agent.

In some embodiments, the kits further comprise (v) a concentrated salt solution. In some embodiments, the concentrated salt solution comprises one or more salts in a concentration range from about 0.5 M to about 3.0 M, e.g., about 0.6 M, 0.7 M, 0.8 M, 0.9 M, 1.0 M, 1.1 M, 1.2 M, 1.3 M, 1.4 M, 1.5 M, 1.6 M, 1.7 M, 1.8 M, 1.9 M, 2.0 M, 2.1 M, 2.2 M, 2.3 M, 2.4 M, 2.5 M, 2.6 M, 2.7 M, 2.8 M, 2.9 M, or 3.0 M. In some embodiments, the concentrated salt solution comprises one or more metal halide salts. In some embodiments, the metal halide salt is selected from the group consisting of LiF, LiCl, LiBr, LiI, NaF, NaCl, NaBr, NaI, KF, KCl, KBr, KI, RbF, RbCl, RbBr, RbI, CsF, CsCl, CsBr, CsI, $BeF_2$, $BeCl_2$, $BeBr_2$, $BeI_2$, $MgF_2$, $MgCl_2$, $MgBr_2$, $MgI_2$, $CaF_2$, $CaCl_2$, $CaBr_2$, $CaI_2$, $SrF_2$, $SrCl_2$, $SrBr_2$, $SrI_2$, $BaF_2$, $BaCl_2$, $BaBr_2$, $BaI_2$, and mixtures thereof. In some embodiments, the concentrated salt solution comprises KCl and KI. In some embodiments, the concentrated salt solution comprises 0.6 M KCl and 1.0 M KI.

DEFINITIONS

The terms "tissue" or "biological tissue" interchangeably refer to a collection of interconnected cells and extracellular matrix that perform a similar function or functions within an organism. Biological tissues include, without limitation, connective tissue, muscle tissue, nervous tissue (of the brain, spinal cord, and nerves), epithelial tissue, and organ tissue. Connective tissue includes fibrous tissue, e.g., fascia, tendon, ligaments, heart valves, bone, and cartilage. Muscle tissue includes skeletal muscle tissue, smooth muscle tissue, e.g., esophageal, stomach, intestinal, bronchial, uterine, urethral, bladder, and blood vessel tissue, and cardiac muscle tissue. Epithelial tissue includes simple epithelial tissue, e.g., alveolar epithelial tissue, blood vessel endothelial tissue, and heart mesothelial tissue, and stratified epithelial tissue. The biological tissue can additionally be selected, without limitation, from the group consisting of heart valve, vessel, vascular conduit, artery, vein, skin, dermis, pericardium, dura, intestinal submucosa, ligament, tendon, bone, cartilage, ureter, urinary bladder, liver, lung, umbilical cord, and heart. Multiple tissues/tissue types comprise organs. Organs are included herein under the terms "tissue and/or "biological tissue."

The phase "intact tissue" refers to tissue that has not been minced or homogenized. The intact tissue may be a whole tissue or a complete organ.

The term "organ" as used herein refers to a collection of tissues joined in a structural unit to serve a common function.

The term "dermis" as used herein refers to the layer of skin between the epidermis and the subcutaneous tissues.

The term "epithelial tissue" as used herein refers to the tissue covering the whole surface of the body or lining certain organ systems exposed to the external environment, such as the gastrointestinal tract, the urogenital tract, or the lung. It is made up of cells closely packed and arranged in at least one layer. This tissue is specialized to form a covering or lining of all internal and external body surfaces.

The terms "patient," "subject" or "individual" interchangeably refers to a mammal, for example, a human or a non-human mammal, including primates (e.g., macaque, pan troglodyte, pongo), a domesticated mammal (e.g., felines, canines), an agricultural mammal (e.g., bovine, ovine, porcine, equine) and a laboratory mammal or rodent (e.g., rattus, murine, lagomorpha, hamster).

The term "cellular and/or soluble macromolecular component" as used herein refers to soluble substances constituting portions of the cell or produced by cells, including cell membranes, cytosol, and soluble macromolecules (e.g. proteins, nucleic acids, polypeptides, glycoproteins, carbohydrates, lipids, phospholipids, etc.). Cellular and/or soluble macromolecular components that induce an immune response in a subject are immunogenic antigens.

The term "recellularization" as used herein refers to removing the cells from a biological tissue, for example, an organ, leaving only the extracellular matrix to be subsequently repopulated with cells, preferably live cells. Recellularization is especially useful in tissue engineering.

The term "extracellular matrix" (ECM) as used herein refers to the extensive and complex structure between the cells—the extracellular part of the biological tissue. The ECM generally comprises the structural component of the tissue, including its organization, shape, and strength (i.e., ability to resist external forces). Due to its diverse nature and composition, the ECM can serve many additional functions, such as providing support and anchorage for cells, segregating tissues from one another, and regulating intercellular communication. The ECM can influence a cell's dynamic behavior. In addition, it sequesters a wide range of cellular growth factors and acts as a local depot for them. Included in the ECM are insoluble structural molecules that have been secreted by cells and comprise components such as collagen, elastin, and large soluble proteoglycans.

A "decellularized extracellular matrix" refers to an ECM wherein the endogenous cells have been substantially removed. In various embodiments, the decellularized ECM is isolated or separated from at least about 60%, 70%, 80%, 90%, 95%, 99%, or more, of endogenous cellular material. The presence or extent of endogenous cellular material can be determined using any method known in the art, e.g., Western blotting, detection of nuclei, microscopy, etc.

The phrase "substantially intact" with respect to a tissue scaffold and/or decellularized extracellular matrix (ECM) refers to an ECM that has been subject to antigen removal and has structural integrity, biochemical composition and tensile strength that is not significantly different from an ECM from the same tissue before it is subject to antigen removal.

The phrase "substantially free of endogenous antigens" with respect to a tissue scaffold and/or decellularized extracellular matrix (ECM) refers to a tissue scaffold and/or ECM wherein the endogenous antigen components (e.g., proteins, lipids, carbohydrates, nucleic acids) have been substantially removed. In various embodiments, the decellularized ECM is isolated or separated from at least about 60%, 70%, 80%, 90%, 95%, 99%, or more, of endogenous antigen components. The presence or extent of endogenous antigen components can be determined using any method known in the art, e.g., immunoassays, Western blotting, ELISA, gel electrophoresis, lymphocyte proliferation assays, etc. In various embodiments, tissue scaffolds and/or ECM that are substantially free of endogenous antigens do not elicit a significant or destructive immune response, e.g., an allogeneic and/or xenogeneic immune response, in vitro or in vivo, directed against the tissue scaffolds and/or ECM.

The term "sulfobetaine" refers to zwitterionic amphiphilic molecules that contain a polarized sulfobetaine head group (e.g., dimethylsulfonioacetate $(CH_3)_2S^+$—$CH_2$—$CO_2^-$). In various embodiments, the head group is followed by a three-carbon linkage between the quaternary ammonium and the amido nitrogen. In various embodiments, the sulfobetaine comprises a linear hydrocarbon tail composed of 13 to 16 carbons. The sulfobetaine can be a detergent or a non-detergent molecule.

DETAILED DESCRIPTION

1. Introduction

Figure 1:
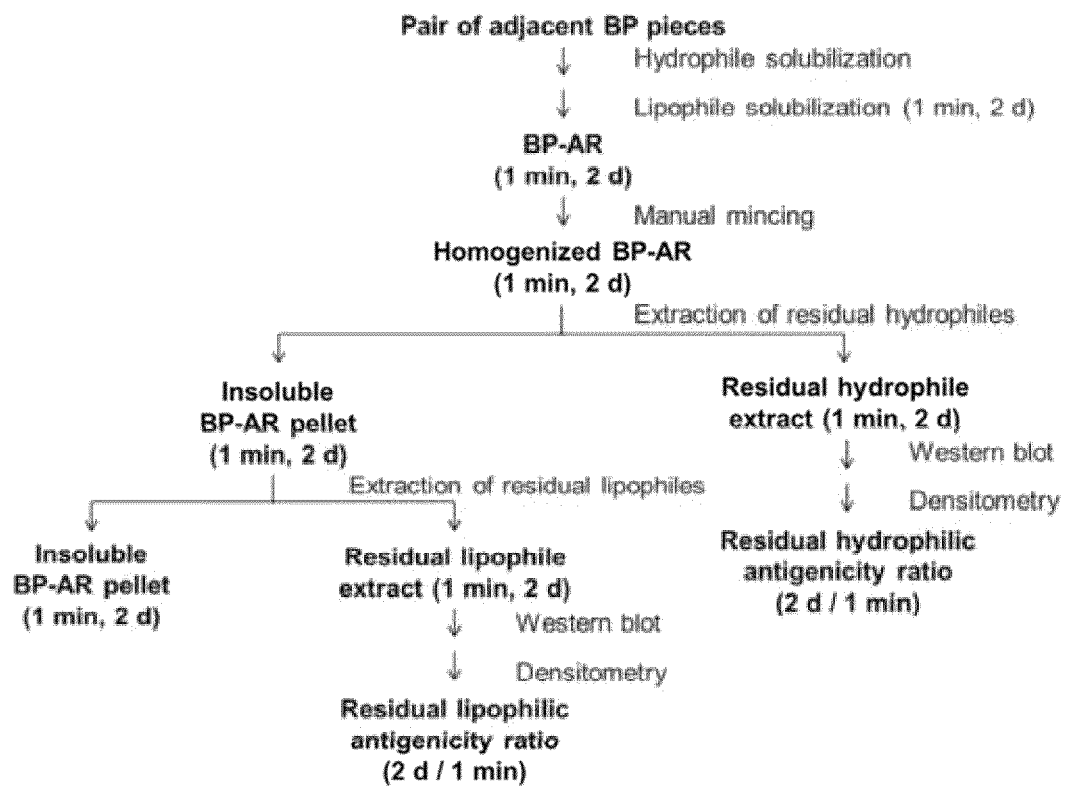
FIG. 1 illustrates a schematic of antigen removal (AR) and assessment of residual antigenicity. Residual hydrophiles (e.g., WSPs) and lipophiles (e.g., LSPs) extracted from bovine pericardium following AR (BP-AR) were subjected to Western blot and probed with rabbit serum generated against native bovine pericardium. Residual hydrophilic and lipophilic antigenicity ratios were defined as the intensity of banding following 2 days of AR divided by 1 min of AR.
Figure 2:
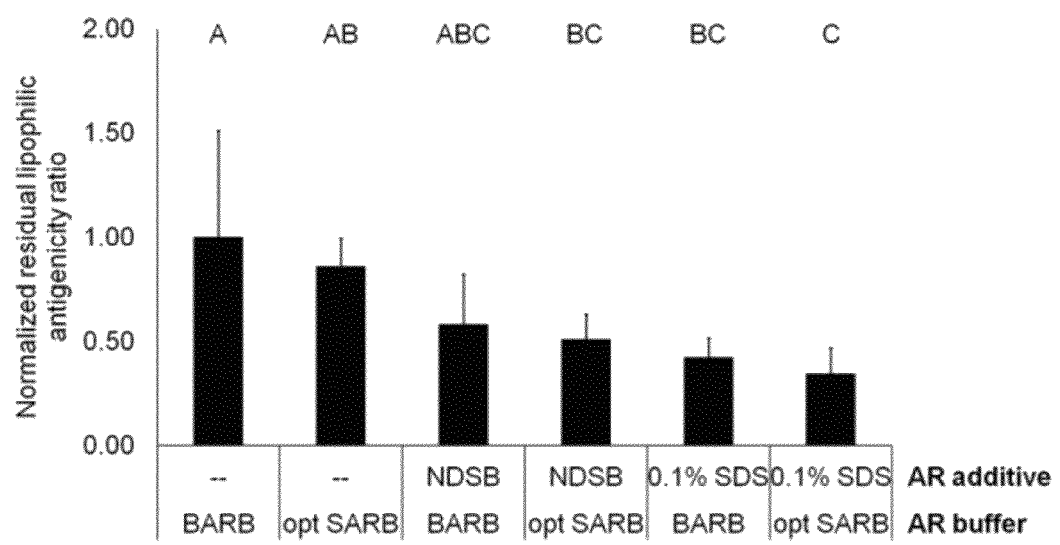
FIG. 2 illustrates residual lipophilic antigenicity of bovine pericardium following one-step AR. Residual lipophilic antigenicity is not significantly decreased with hydrophile solubilization (optimized solubilizing AR buffer (opt SARB) vs. basic AR buffer (BARB)) containing no additional additive, 134 mM 3-(benzyldimethylammonio) propanesulfonate (NDSB-256) or 0.1% (w/v) SDS. Results are plotted as mean±standard deviation. Groups not connected by the same letter are significantly different, $p<0.05$ (n=6 per group).

The present invention is based, in part, on methods for the sequential solubilization and extraction of water-soluble antigenic components and lipid-soluble antigenic components from tissue to produce tissue scaffold or decellularized extracellular matrix (ECM) with ECM structure, biochemical composition, mechanical properties, and recellularization capacity that is substantially the same as the tissue prior to antigen removal procedures. Stepwise or sequential antigen removal of water-soluble and lipid-soluble antigens from tissue substantially reduce in vivo immune response towards the produced tissue scaffold or decellularized ECM. Sequential solubilization and extraction of water-soluble antigenic components and lipid-soluble antigenic components from tissue allows for the production of an immunologically-acceptable, structurally-integral, mechanically-sound, tissue scaffold compatible with recellularization, e.g., for use in tissue engineering and/or tissue regeneration.

The present invention is further based, in part, on methods for the sequential solubilization and extraction of cytoskeletal components (e.g., filamentous actin and/or microtubules), water-soluble antigenic components and lipid-soluble antigenic components from tissue to produce tissue scaffold or decellularized extracellular matrix (ECM) with ECM structure, biochemical composition, mechanical properties and recellularization capacity that is substantially the same as the tissue prior to antigen removal procedures. Stepwise or sequential antigen removal of cytoskeletal components, water-soluble and lipid-soluble antigens from tissue substantially reduces in vivo immune response towards the produced tissue scaffold or decellularized ECM. Sequential solubilization and extraction of cytoskeletal components, water-soluble antigenic components and lipid-soluble antigenic components from tissue allows for the production of an immunologically-acceptable, structurally integral, mechanically sound, tissue scaffold compatible with recellularization, e.g., for use in tissue engineering and/or tissue regeneration. When applied to muscle tissues, the methods can further comprise the step of relaxing, solubilizing and removing sarcomeric components.

Biomaterial antigenicity is the primary hurdle for the use of xenogeneic scaffolds in tissue engineering and regenerative medicine. To reduce or eliminate the persistent presence of antigens on decellularized tissue to elicit the immune response upon implantation we have developed a more rigorous antigen removal (AR) process. Solubilization-based AR has been shown to enhance the removal of water-soluble protein (WSP) antigens in tissues, including bovine pericardium (BP), beyond that achieved by decellularization using hypotonic solution or SDS (e.g., at a concentration in the range of 0.1-1.0% w/v). However, the diversity of protein antigens within a tissue necessitates development of AR strategies capable of addressing a spectrum of protein antigen solubilities. The present invention is based, in part, on the discovery of antigen removal (AR) methods promoting the solubilization of lipid-soluble proteins (LSPs) to reduce the residual LSP antigenicity of tissues, including BP, when applied as a separate step of AR to solubilizing WSP. Promoting the solubilization of a protein subset (cytoskeletal components, WSPs and/or LSPs) significantly reduces the residual antigenicity of that specific subset of protein antigens (cytoskeletal components, WSPs and/or LSPs, respectively). However, promoting the solubilization of a protein subset (cytoskeletal components, WSPs and/or LSPs) does not significantly reduce residual antigenicity of the other subset of protein antigens (cytoskeletal components, WSPs and/or LSPs, respectively). Facilitating solubilization of cytoskeletal components (e.g., by including one or more cytoskeletal destabilizing and/or depolymerizing agents), WSP (e.g., using 100 mM dithiothreitol and 100 mM potassium chloride in solubilizing antigen removal buffer) and LSP (e.g., using 1-4% (w/v) ASB-14 in solubilizing antigen removal buffer) in a multi-step sequential, differential AR strategy markedly reduces the residual antigenicity of tissues beyond that achieved with either one-step AR or decellularization by 1% (w/v) SDS. Use of 1-4% (w/v) ASB-14 for LSP AR does not compromise the biomaterial properties of tissue following antigen removal. A multi-step AR strategy promoting sequential, differential protein solubilization significantly reduced residual LSP antigens beyond that achieved with one-step AR of WSPs while maintaining biomaterial functional properties. Moreover, total DNA content and/or residual nuclei counts may not be an appropriate indicator of residual LSP antigenicity. This study demonstrates the importance of a sequential, differential protein solubilization approach for the reduction of biomaterial antigenicity in xenogeneic scaffold generation for tissue engineering.

For the application to muscle tissue, principles of protein chemistry can be applied to antigen removal of each antigenic class from muscle tissue. The methods entail a multimodal approach to disassemble and solubilize the myocyte sarcomere structure (the functional rigid force-producing units that make up myocytes). This approach produces more complete removal of antigens from myocytes than previously reported methods, while maintaining ECM structure-function relationships and improving recellularization capacity. The methods described herein produce decellularized tissue and ECM scaffolds with significantly reduced antigenicity, due to more complete removal of cytoskeletal, sarcomeric, hydrophilic and lipophilic antigens. This present methods employ macromolecular disassembly of the basic structural unit of myocytes (sarcomeres) combined with the principles of sequential, differential solubilization of water-soluble antigens and lipid-soluble antigens for sequential myocyte solubilization and antigen removal from muscle tissue (e.g., cardiac muscle tissue, striated or skeletal muscle tissue, smooth muscle tissue).

With respect to muscle tissue, the methods generally involve the treatment of allogeneic (e.g., from a different individual of the same species of the subject receiving the tissue) and xenogeneic (e.g., from a different species of the subject receiving the tissue) muscle tissues (e.g., myocardial, skeletal or smooth muscle) for the purpose of removing cells, cellular debris, antigens, proteins, nucleic acids, phospholipids, and other macromolecules prior to implantation. The approach to production of such ECM scaffolds described herein is based on the protein chemistry principles of sequential, differential solubilization, utilized for protein extraction from homogenized tissues, e.g., for proteomic applications. Protein solubilization is known to be important for achieving protein extraction from homogenized sample material for use in subsequent two-dimensional gel electrophoresis (2-DE). Protein precipitation tends to occur due to molecular interactions which result in protein aggregation (e.g., disulfide bond formation, hydrophobic interactions, non-covalent interactions). Consequently, disruption of macromolecular interactions within and between proteins is important for achieving and maintaining protein solubility. Therefore, the goal of most protein extraction protocols is to disaggregate, denature, reduce and consequentially solubilize the protein type of interest. Furthermore, various protein types within a tissue exhibit different physicochemical properties (e.g., cytoplasmic proteins are generally water soluble, integral membrane proteins are generally hydrophobic). No single extraction condition is capable of simultaneously solubilizing all proteins within a tissue.

Protein extraction protocols, therefore, generally utilize sequential extraction techniques to solubilize proteins in a stepwise manner from the tissue by serial application of extraction solutions with characteristics designed to favor solubilization of a particular protein type. Previously reported decellularization and AR methods have largely failed to apply the principles of protein chemistry required to achieve solubilization of various antigenic protein types within the tissue. The present methods are based, in part, on the recognition that the macromolecular structure of the sarcomere prevents solubilization and subsequent removal of these components from the material. We therefore designed a specifically targeted stepwise approach to relax, depolymerize and render the components of the sarcomere amenable to solubilization. Combining sarcomere disassembly and solubilization with sequential, differential solubilization of water soluble antigens and lipid soluble antigens for antigen removal results in enhanced removal of cellular components and antigens from muscle tissues.

2. Methods for Removing Antigen Components from Tissue

The present methods relate to the removal of antigens from tissues, e.g., cells, cellular debris, proteins, nucleic acids, phospholipids, carbohydrates, and other macromolecules, e.g., from tissues allogeneic (i.e., derived from within the same species) to or xenogeneic (i.e., derived from different species) to a recipient of the tissue, e.g., in tissue or organ transplantation or regeneration.

a. Tissues

The tissues subject to sequential antigen removal can be from any tissue suitable for transplantation. Generally, the tissue is live and unfixed. In various embodiments, tissues subject to sequential antigen removal include without limitation connective tissue, muscle tissue, nervous tissue (of the brain, spinal cord, and nerves), epithelial tissue, and organ tissue. Connective tissue includes fibrous tissue like fascia, tendon, ligaments, heart valves, bone, and cartilage. Muscle tissue includes skeletal muscle tissue, smooth muscle tissue, such as esophageal, stomach, intestinal, bronchial, uterine, urethral, bladder, and blood vessel tissue, and cardiac muscle tissue. Epithelial tissue includes simple epithelial tissue, such as alveolar epithelial tissue, blood vessel endothelial tissue, and heart mesothelial tissue, and stratified epithelial tissue. In various embodiments, the tissue is subject to antigen removal is heart, heart valve, vessel, vascular conduit, artery, vein, skin, dermis, pericardium, dura, intestinal submucosa, ligament, tendon, bone, cartilage, ureter, urinary bladder, liver, lung, and umbilical cord. The tissue may be a part of an organ or be an intact organ.

The tissue may be from the intended recipient (e.g., is syngeneic), from the same species as the intended recipient (e.g., is allogeneic) or from a different species from the intended recipient (e.g., is xenogeneic) of the tissue scaffold or decellularized ECM produced by removal of the antigens. In various embodiments, the tissue is from a first human and intended to be transplanted into second human. In various embodiments, the tissue is from a porcine, ovine, bovine, ostrich (e.g., of the genus *Struthio*) or a non-human primate and intended to be transplanted into a human.

As appropriate, the tissue can be submerged in solubilization solution or perfused with solubilizing solution. Antigens can be effectively removed from thinner tissues (e.g., tissues having less about 1 mm thickness) by submerging. Antigens can be effectively removed from thicker tissues and intact organs by perfusion of the tissue with solubilizing solution.

Generally, the tissue is subjected to solubilization as soon as practicable after extraction from the original host and before the tissue is substantially decomposed. In various embodiments, the tissue is subjected to solubilization within 12 hours after extraction, e.g., within 10, 8, 6, 4, 3, 2, 1 hours after extraction from the original host.

b. Destabilizing and/or Depolymerizing Cytoskeletal Components

In various embodiments, the tissue can be contacted with (e.g., submerged in or perfused with) a solution for destabilizing and/or depolymerizing one or more cytoskeletal components (e.g., filamentous actin and/or microtubules) under sufficient conditions and for a sufficient time to depolymerize, solubilize and extract a portion of the cytoskeletal components, e.g., polymerized and/or filamentous cytoskeletal components. In various embodiments, the tissue is contacted with one or more agents that destabilize and/or depolymerize filamentous actin and/or microtubules.

In some embodiments, the one or more cytoskeletal destabilizing and/or depolymerizing agents comprise one or more actin destabilizing and/or depolymerization agents. In some embodiments, the one or more actin destabilizing and/or depolymerizing agents are selected from the group consisting of Cytochalasin A, Cytochalasin B, Cytochalasin C, Cytochalasin D, Cytochalasin E, Cytochalasin F, Cytochalasin G, Cytochalasin H, Cytochalasin I, Cytochalasin J, Latrunculin A, Latrunculin B, Swinholide A, Misakinolide A, Bistheonelide A, Scytophycin A, Scytophycin B, Scytophycin D, Scytophycin E, 19-O-Demethylscytophycin C, 6-Hydroxyscytophycin B, 6-Hydroxy-7-O-methylscytophycin E and tolytoxin, Mycalolide A, Mycalolide B, Mycalolide C, seco-mycalolide A and 30-hydroxymycalolide A, Halichondramide, (19Z)-halichondramide, kabiramides B, kabiramides C, kabiramides D, kabiramides G, kabiramides J, kabiramides K, ulapualide A, jaspamide, Dihydrohalichondramide, Aplyronine A, Aplyronine B, Aplyronine C, Pectenotoxin 2, Pectenotoxin 6, and Migrastatin. In some embodiments, the actin depolymerization agents depolymerize filamentous cytoskeletal actin (F-actin). In some embodiments, the actin depolymerization agents depolymerize filamentous α-sarcomeric actin (F-actin).

In some embodiments, the one or more cytoskeletal destabilizing and/or depolymerizing agents comprise one or more microtubule depolymerization and/or destabilizing agents. In some embodiments, the one or more microtubule depolymerization and/or destabilizing agents is selected from the group consisting of colchicine, colcemid, vinblastine, vincristine, myoseverin, nocodazole, podophyllotoxin, polygamain and taxol.

In various embodiments, the solution comprising the one or more cytoskeletal component destabilizing and/or depolymerizing agents is an aqueous solution. In varying embodiments, the solution comprising the one or more cytoskeletal component destabilizing and/or depolymerizing agents is a physiologically isotonic aqueous solution (e.g., serum free cell culture solution). In varying embodiments, the one or more cytoskeletal component destabilizing and/or depolymerizing agents is added to a solution for solubilizing the water-soluble antigens, as described below, in the section entitled "Solubilizing Water-Soluble Antigens in the Tissue." In some embodiments, the aqueous solution comprises glucose, e.g., at a concentration in the range of about 5-50 mM, e.g., about 5-25 mM, e.g., about 5 mM, 10 mM, 15 mM, 20 mM, 25 mM, 30 mM, 35 mM, 40 mM, 45 mM, or 50 mM.

In varying embodiments, the tissue is contacted with (e.g., is submerged in or perfused with) each cytoskeletal destabilizing and/or depolymerizing agent at a concentration in the range of about 1 nM to about 10 µM, e.g., at a concentration of about 1 nM, 5 nM, 10 nM, 25 nM, 50 nM, 75 nM, 100 nM, 500 nM, 750 nM, 1 µM, 5 µM, 10 µM, 15 µM, 20 µM, 25 µM, 30 µM, 35 µM, 40 µM, 45 µM and 50 µM.

In various embodiments, the tissue is submerged in or perfused with the solution comprising one or more cytoskeletal depolymerizing and/or destabilizing agents for at least about 0.5, 1, 2, 4, 6, 8, 10, 12, 14, 16, 18, 20, 22 or 24 hours, e.g., for at least about 2, 3, 4, 5, 6, 7 days, as appropriate. The tissue may be washed one or more times during the time period of submerging or perfusing, e.g., to promote diffusion and separation of cytoskeletal antigens from the tissue.

In various embodiments, the depolymerization, solubilization, extraction and/or removal of depolymerized cytoskeletal components is performed at a temperature above freezing (e.g., above 0° C.) and at or below body temperature (e.g., at or below about 37° C.). In various embodiments, the depolymerization, solubilization, extraction and/or removal of depolymerized cytoskeletal components is performed at a refrigerated temperature, e.g., between about 4-10° C. In various embodiments, the depolymerization, solubilization, extraction and/or removal of depolymerized cytoskeletal components is performed at room temperature, e.g., between about 20-30° C., e.g., about 25° C. In various embodiments, the depolymerization, solubilization, extraction and/or removal of depolymerized cytoskeletal components is performed at human body temperature, e.g., about 37° C. The depolymerization, solubilization, extraction and/or removal steps can be performed at the same or different temperatures.

In performing the methods, the step of contacting the tissue with a solution comprising one or more cytoskeletal destabilizing and/or depolymerizing agents can be conducted concurrently with or in a separate step from the step of contacting the tissues with a solution for solubilizing the water-soluble antigens. After a portion of the cytoskeletal components are depolymerized, solubilized and extracted from the tissue, the solubilized and extracted cytoskeletal components are separated from the tissue, e.g., in a wash step. In various embodiments, washing is performed by contacting tissue (e.g., submerging in or perfusing with) with fresh physiologically isotonic solution (e.g., serum free cell culture solution) or a solution for solubilizing the water-soluble antigens, as described below. The step of depolymerizing, solubilizing and extracting cytoskeletal components can be performed for one or multiple iterations, e.g., 2, 3, 4, 5, or more iterations, as appropriate. For example, the iterations of solubilizing depolymerized cytoskeletal components and separating (e.g., rinsing) the cytoskeletal components from the tissue can be repeated until extracted cytoskeletal components are no longer detected in the depolymerizing solution or the tissue, or until the detectable cytoskeletal components in the extraction solution or the tissue fall below a predetermined threshold level, as appropriate.

c. Solubilizing Water-Soluble Antigens in the Tissue

The tissue can be contacted with (e.g., submerged in or perfused with) a solution for solubilizing the water-soluble antigens under sufficient conditions and for a sufficient time to extract a portion of the water soluble antigens from the tissue or to reach an equilibrium between the water-soluble antigens within the tissue and water soluble antigens in the solution, as appropriate.

In various embodiments, the tissue is submerged in or perfused with the solution for solubilizing the water-soluble antigens for at least about 0.5, 1, 2, 4, 6, 8, 10, 12, 14, 16, 18, 20, 22 or 24 hours, e.g., for at least about 2, 3, 4, 5, 6, 7 days, as appropriate. The tissue may be washed one or more times during the time period of submerging or perfusing, e.g., to promote diffusion and separation of water-soluble antigens from the tissue.

In various embodiments, removal of water-soluble antigens is performed at a temperature above freezing (e.g., above 0° C.) and at or below body temperature (e.g., at or below about 37° C.). In various embodiments, removal of water-soluble antigens is performed at a refrigerated temperature, e.g., between about 4-10° C. In various embodiments, removal of water-soluble antigens is performed at room temperature, e.g., between about 20-30° C., e.g., about 25° C. In various embodiments, removal of water-soluble antigens is performed at human body temperature, e.g., about 37° C.

In various embodiments, the water-soluble antigens are solubilized in a solution comprising a buffering agent, a reducing agent, a protease inhibitor, and one or more salts suitable for maintaining protein solubility.

In various embodiments, the buffering agent maintains a pH (e.g., has a pKa) to allow for solubility of the antigens in aqueous solution. For example, in some embodiments, the buffering agent maintains a pH in the range of about 4-11, e.g., a pH in the range of about 4-6, 8-11, 5-10 or 6-9. In some embodiments, the buffering agent maintains a pH of at least about 8. In some embodiments, the buffering agent maintains a pH of less than about 5. Illustrative buffering agents include without limitation Tris-HCl, phosphate, citric acid, acetate, imidazole, carbonate, MES, Bis-Tris, ADA, aces, PIPES, MOPSO, Bis-Tris propane, BES, MOPS, TES, HEPES, DIPSO, MOBS, TAPSO, Trizma, HEPPSO, POPSO, TEA, EPPS, Tricine, Gly-Gly, Bicine, HepBS, TAPS, AMPD, CHES, CAPSO, AMP, CAPS and CABS. These and other buffering agents of use are well-known in the art and commercially available, e.g., from Sigma-Aldrich (on the internet at sigmaaldrich.com). In some embodiments, the buffering is Tris-HCl.

In some embodiments, the one or more salts comprise a monovalent or a divalent anion. In some embodiments, the one or more salts comprise a metal halide salt. Illustrative metal halide salts of use include without limitation LiF, LiCl, LiBr, LiI, NaF, NaCl, NaBr, NaI, KF, KCl, KBr, KI, RbF, RbCl, RbBr, RbI, CsF, CsCl, CsBr, CsI, $BeF_2$, $BeCl_2$, $BeBr_2$, $BeI_2$, $MgF_2$, $MgCl_2$, $MgBr_2$, $MgI_2$, $CaF_2$, $CaCl_2$, $CaBr_2$, $CaI_2$, $SrF_2$, $SrCl_2$, $SrBr_2$, $SrI_2$, $BaF_2$, $BaCl_2$, $BaBr_2$, $BaI_2$, and mixtures thereof. In some embodiments, the one or more salts comprise KCl. In various embodiments, the one or more salts are included at a concentration of at least about 50 mM, 75 mM, or 100 mM, for example, at least about 150 mM, 200 mM, 250 mM, 300 mM, 350 mM, 400 mM, 450 mM, 500 mM. 600 mM, 700 mM, 800 mM, 900 mM or 1000 mM, for example, in the range of about 100-500 mM or about 100-200 mM.

Illustrative reducing agents for use in the solution for solubilizing the water-soluble antigens include without limitation Tributylphosphine (TBP), beta mercaptoethanol, 2-mercaptoethylamine, tris(2-carboxyethyl)phosphine (TCEP), cysteine-HCl, and dithiothreitol (DTT). In some embodiments, the reducing agent is DTT.

Illustrative protease inhibitors for use in the solution for solubilizing the water-soluble antigens include without limitation aspartic protease inhibitors, cysteine protease inhibitors, metalloprotease inhibitors, serine protease inhibitors (serpins), threonine protease inhibitors, trypsin inhibitors, and mixtures thereof. In various embodiments, the protease inhibitor is an 19, 110, 114, 124, 129, 134, 136, 142, 148, 153, 167, 168, 178 inhibitor, or a mixture thereof. In some embodiments, the protease inhibitor is AEBSF (4-(2-Aminoethyl) benzenesulfonyl fluoride hydrochloride), also sold as PEFABLOC®. In some embodiments, the protease inhibitor is Phenylmethylsulfonyl fluoride (PMSF). Numerous protease inhibitor cocktails of use are commercially available from Roche Molecular Biochemicals.

In some embodiments, the water-soluble antigens are solubilized in a solution that comprises one or more of an antibacterial agent and/or an antifungal agent.

In some embodiments, the water-soluble antigens are solubilized in a solution that comprises a chelation agent. Illustrative chelation agents include without limitation ethylenediaminetetraacetic acid (EDTA), diethylenetriaminepentaacetic acid (DTPA), Citric Acid, N,N-bis(carboxymethyl)glycine (NTA), and the meso isomer of Dimercaptosuccinic acid (DMSA).

In some embodiments, the water-soluble antigens are solubilized in a solution that does not comprise an amphiphile. In some embodiments, the water-soluble antigens are solubilized in a solution that does not comprise a detergent. In some embodiments, the water-soluble antigens are solubilized in a solution that comprises a non-detergent sulfobetaine. Illustrative non-detergent sulfobetaines include without limitation NDSB-256, NDSB-211, NDSB-195, NDSB-221 and NDSB-201.

In some embodiments, the water-soluble antigens are solubilized in a solution comprising Tris-HCl, dithiothreitol (DTT), a protease inhibitor, and KCl. In a particular embodiment, the water-soluble antigens are solubilized in a solution comprising 10 mM Tris-HCl, 100 mM DTT, 100 mM KCl and 2 mM $MgCl_2$. A protease inhibitor and/or an antibacterial agent and/or an antifungal agent may also be included.

d. Separating the Tissue from the Solubilized Water-Soluble Antigens

Once the tissue has been submerged in or perfused with the solution for solubilizing the water-soluble antigens under sufficient conditions and for a sufficient time, the tissue can be separated from the solution, now containing a portion of the water soluble antigens extracted from the tissue. Separation of the tissue and the solubilizing solution can be performed using any methods known in the art. In various embodiments, the tissue can be rinsed, e.g., in the same solution for solubilizing the water-soluble antigens. Optionally, the tissue can be subject to saturation with (e.g., submerged in or perfused with) solubilization solution and separated for one or more iterations in fresh solution for solubilizing the water-soluble antigens for a sufficient time to extract a further portion of the water soluble antigens from the tissue or to reach an equilibrium between the water-soluble antigens within the tissue and water soluble antigens in the solution, as appropriate. The iterations of submerging in or perfusing with solution for solubilizing the water-soluble antigens and separating (e.g., rinsing) can be repeated until extracted water-soluble antigens are no longer detected in the solution for solubilizing the water-soluble antigens, or until the detectable extracted water-soluble antigens fall below a predetermined threshold level, as appropriate.

In various embodiments, the separation and removal of the water-soluble antigens from the tissue can involve centrifugation and/or filtration, as appropriate, to separate the tissue from the solution for solubilizing the water-soluble antigens containing a portion of and/or saturated with extracted water-soluble antigens. In other embodiments, the tissue is removed from solution for solubilizing the water-soluble antigens and rinsed with being subjected to centrifugation or filtration.

In various embodiments, more frequent iterations of submerging or perfusing and separation (e.g., rinsing) and a larger number of iterations of submerging or perfusing and separating (e.g., rinsing) can allow for faster solubilization and removal of water-soluble antigens from the tissue. For example, the tissue can be saturated with (e.g., submerged in or perfused with) a first solution for solubilizing the water-soluble antigens for a sufficient time to extract at least a portion of the water soluble antigens; separated from the first solution, now containing a portion of extracted water soluble antigens, before equilibrium is reached between the water-soluble antigens within the tissue and water soluble antigens in the solution; saturated with (e.g., submerged in or perfused with) a second solution for solubilizing the water-soluble antigens for a sufficient time to extract at least a portion of the water soluble antigen; and separated from the second solution, now containing a portion of extracted water soluble antigens, before equilibrium is reached between the water-soluble antigens within the tissue and water soluble antigens in the solution. Further iterations of submerging or perfusing and separation can be performed, as appropriate or desired, until a sufficiently low level of water soluble antigens extracted into the solution for solubilizing the water-soluble antigens is achieved.

e. Solubilizing Lipid-Soluble Antigens in the Tissue

In various embodiments, tissues that have been subject to extraction and separation of water-soluble antigens can subsequently be subject to extraction of lipid-soluble antigens. In other embodiments, tissues are first subject to extraction of lipid soluble antigens and second subject to extraction of water-soluble antigens.

The tissue can be saturated with (e.g., submerged in or perfused with) a solution for solubilizing the lipid-soluble antigens for a sufficient time to extract a portion of the lipid soluble antigens from the tissue or to reach an equilibrium between the lipid-soluble antigens within the tissue and lipid soluble antigens in the solution, as appropriate.

In various embodiments, the tissue is saturated with (e.g., submerged in or perfused with) the solution for solubilizing the lipid-soluble antigens for at least about 0.5, 1, 2, 4, 6, 8, 10, 12, 14, 16, 18, 20, 22 or 24 hours, e.g., for at least about 2, 3, 4, 5, 6, 7 days, as appropriate. The tissue may be washed one or more times during the time period of submerging or perfusing, e.g., to promote diffusion and separation of lipid-soluble antigens from the tissue.

In various embodiments, removal of lipid-soluble antigens is performed at a temperature above freezing (e.g., above 0° C.) and at or below body temperature (e.g., at or below about 37° C.). In various embodiments, removal of lipid-soluble antigens is performed at a refrigerated temperature, e.g., between about 4-10° C. In various embodiments, removal of lipid-soluble antigens is performed at room temperature, e.g., between about 20-30° C., e.g., about 25° C. In various embodiments, removal of lipid-soluble antigens is performed at human body temperature, e.g., about 37° C.

In some embodiments, the lipid-soluble antigens are solubilized in a solution comprising a buffering agent, a reducing agent, a protease inhibitor, one or more salts suitable for maintaining protein solubility and an amphiphile.

In various embodiments, the amphiphile is a zwitterionic detergent. In some embodiments, the amphiphile is a sulfobetaine. Illustrative sulfobetaines of use include without limitation 3-[N,N-Dimethyl(3-myristoylaminopropyl)ammonio] propanesulfonate (amidosulfobetaine-14; ASB-14); amidosulfobetaine-16 (ASB-16); 4-n-Octylbenzoylamidopropyl-dimethylammonio sulfobetaine (ASB-C8Ø); 3-(N,N-Dimethyloctylammonio) propanesulfonate inner salt (SB3-8); N-Decyl-N,N-dimethyl-3-ammonio-1-propanesulfonate (SB 3-10), N-Decyl-N,N-dimethyl-3-ammonio-1-propanesulfonate (SB 3-12), N-Tetradecyl-N,N-dimethyl-3-ammonio-1-propanesulfonate (SB 3-14); 3-(N,N-Dimethylpalmitylammonio) propanesulfonate (SB3-16); 3-(N,N-Dimethyloctadecylammonio) propanesulfonate (SB3-18); 3-(1-Pyridinio)-1-propanesulfonate (NDSB-201); 3-(Benzyldimethylammonio) propanesulfonate (NDSB-256); NDSB-211, NDSB-195, NDSB-221; 3-[(3-Cholamidopropyl)dimethylammonio]-1-propanesulfonate (CHAPS), 3-[(3-Cholamidopropyl)dimethylammonio]-2-hydroxy-1-propanesulfonate (CHAPSO), and mixtures thereof. In various embodiments, the sulfobetaine is an amidosulfobetaine. Illustrative amidosulfobetaines include without limitation, ASB-14, ASB-16 and ASB-C8Ø. In various embodiments, the sulfobetaine is a non-detergent sulfobetaine. Illustrative non-detergent sulfobetaines include without limitation NDSB-256, NDSB-211, NDSB-195, NDSB-221 and NDSB-201.

In various embodiments, the buffering agent maintains a pH (e.g., has a pKa) to allow for solubility of the antigens in aqueous solution. For example, in some embodiments, the buffering agent maintains a pH in the range of about 4-11, e.g., a pH in the range of about 4-6, 8-11, 5-10 or 6-9. In some embodiments, the buffering agent maintains a pH of at least about 8. Illustrative buffering agents include without limitation Tris-HCl, phosphate, citric acid, acetate, imidazole, carbonate, MES, Bis-Tris, ADA, aces, PIPES, MOPSO, Bis-Tris propane, BES, MOPS, TES, HEPES, DIPSO, MOBS, TAPSO, Trizma, HEPPSO, POPSO, TEA, EPPS, Tricine, Gly-Gly, Bicine, HepBS, TAPS, AMPD, CHES, CAPSO, AMP, CAPS and CABS. These and other buffering agents of use are well-known in the art and commercially available, e.g., from Sigma-Aldrich (on the internet at sigmaaldrich.com). In some embodiments, the buffering is Tris-HCl.

In some embodiments, the one or more salts comprise a monovalent or a divalent anion. In some embodiments, the one or more salts comprise a metal halide salt. Illustrative metal halide salts of use include without limitation LiF, LiCl, LiBr, LiI, NaF, NaCl, NaBr, NaI, KF, KCl, KBr, KI, RbF, RbCl, RbBr, RbI, CsF, CsCl, CsBr, CsI, BeF$_2$, BeCl$_2$, BeBr$_2$, BeI$_2$, MgF$_2$, MgCl$_2$, MgBr$_2$, MgI$_2$, CaF$_2$, CaCl$_2$, CaBr$_2$, CaI$_2$, SrF$_2$, SrCl$_2$, SrBr$_2$, SrI$_2$, BaF$_2$, BaCl$_2$, BaBr$_2$, BaI$_2$, and mixtures thereof. In some embodiments, the one or more salts comprise KCl. In various embodiments, the one or more salts are included at a concentration of at least about 50 mM, 75 mM, or 100 mM, for example, at least about 150 mM, 200 mM, 250 mM, 300 mM, 350 mM, 400 mM, 450 mM or 500 mM.

Illustrative reducing agents for use in the solution for solubilizing the lipid-soluble antigens include without limitation Tributylphosphine (TBP), beta mercaptoethanol, 2-mercaptoethylamine, tris(2-carboxyethyl)phosphine (TCEP), cysteine-HCl, and dithiothreitol (DTT). In some embodiments, the reducing agent is DTT.

Illustrative protease inhibitors for use in the solution for solubilizing the lipid-soluble antigens include without limitation aspartic protease inhibitors, cysteine protease inhibitors, metalloprotease inhibitors, serine protease inhibitors (serpins), threonine protease inhibitors, trypsin inhibitors, and mixtures thereof. In various embodiments, the protease inhibitor is an 19, 110, 114, 124, 129, 134, 136, 142, 148, 153, 167, 168, 178 inhibitor, or a mixture thereof. In some embodiments, the protease inhibitor is AEBSF (4-(2-Aminoethyl) benzenesulfonyl fluoride hydrochloride), also sold as PEFABLOC®. In some embodiments, the protease inhibitor is Phenylmethylsulfonyl fluoride (PMSF). Numerous protease inhibitor cocktails of use are commercially available from Roche Molecular Biochemicals.

In some embodiments, the lipid-soluble antigens are solubilized in a solution that comprises one or more of an antibacterial agent and/or an antifungal agent.

In some embodiments, the lipid-soluble antigens are solubilized in a solution that comprises a chelation agent. Illustrative chelation agents include without limitation ethylenediaminetetraacetic acid (EDTA), diethylenetriaminepentaacetic acid (DTPA), Citric Acid, N,N-bis(carboxymethyl)glycine (NTA), and the meso isomer of Dimercaptosuccinic acid (DMSA).

In some embodiments, the lipid-soluble antigens are solubilized in a solution comprising Tris-HCl, dithiothreitol (DTT), a protease inhibitor, KCl and ASB-14. In a particular embodiment, the lipid-soluble antigens are solubilized in a solution comprising 10 mM Tris-HCl, 100 mM DTT, 100 mM KCl, 2 mM MgCl$_2$ and 1-4% ASB-14. A protease inhibitor and/or an antibacterial agent and/or an antifungal agent may also be included.

f. Separating the Tissue from the Solubilized Lipid-Soluble Antigens

Once the tissue has been saturated with (e.g., submerged in or perfused with) the solution for solubilizing the lipid-soluble antigens for a sufficient time, the tissue can be separated from the solution, now containing a portion of the lipid soluble antigens extracted from the tissue. Separation of the tissue and the solubilizing solution can be performed using any methods known in the art. In various embodiments, the tissue can be rinsed, e.g., in the same solution for solubilizing the lipid-soluble antigens. Optionally, the tissue can be saturated with (e.g., submerged in or perfused with) and separated for one or more iterations in fresh solution for solubilizing the lipid-soluble antigens for a sufficient time to extract a further portion of the lipid soluble antigens from the tissue or to reach an equilibrium between the lipid-soluble antigens within the tissue and lipid soluble antigens in the solution, as appropriate. The iterations of submerging or perfusing in solution for solubilizing the lipid-soluble antigens and separating (e.g., rinsing) can be repeated until extracted lipid-soluble antigens are no longer detected in the solution for solubilizing the lipid-soluble antigens, or until the detectable extracted lipid-soluble antigens fall below a predetermined threshold level, as appropriate.

In various embodiments, the separation and removal of the lipid-soluble antigens from the tissue can involve centrifugation and/or filtration, as appropriate, to separate the tissue from the solution for solubilizing the lipid-soluble antigens containing a portion of and/or saturated with extracted lipid-soluble antigens. In other embodiments, the tissue is removed from solution for solubilizing the lipid-soluble antigens and rinsed with being subjected to centrifugation or filtration.

In various embodiments, more frequent iterations of submerging or perfusing and separation (e.g., rinsing) and a larger number of iterations of submerging or perfusing and separating (e.g., rinsing) can allow for faster solubilization and removal of lipid-soluble antigens from the tissue. For example, the tissue can be saturated with (e.g., submerged in or perfused with) a first solution for solubilizing the lipid-soluble antigens for a sufficient time to extract at least a portion of the lipid soluble antigens; separated from the first solution, now containing a portion of extracted lipid soluble antigens, before equilibrium is reached between the lipid-soluble antigens within the tissue and lipid soluble antigens in the solution; saturated with (e.g., submerged in or perfused with) a second solution for solubilizing the lipid-soluble antigens for a sufficient time to extract at least a portion of the lipid soluble antigen; and separated from the second solution, now containing a portion of extracted lipid soluble antigens, before equilibrium is reached between the lipid-soluble antigens within the tissue and lipid soluble antigens in the solution. Further iterations of submerging or perfusing and separation can be performed, as appropriate or desired, until a sufficiently low level of lipid soluble antigens extracted into the solution for solubilizing the lipid-soluble antigens is achieved.

g. Recellularizaton/Repopulation with Live Cells

In various embodiments, the tissue scaffold and/or decellularized ECM (e.g., heart valves, vascular conduits, arteries, veins, skin, dermis, ligaments, tendons, bone, cartilage, muscle, ureter, urinary bladder, liver, heart, and other organs) can be recellularized or repopulated prior to implantation by co-culturing the tissue processed according to a method of the invention with live cells, e.g., cells autologous to the recipient of the tissue; cells of the same tissue type as the tissue to be transplanted into the recipient; mesenchymal stem cells; and mixtures thereof.

In various embodiments, the tissue scaffold and/or decellularized ECM is repopulated or recellularized with mesenchymal stem cells exhibit immunomodulatory properties through mechanisms involving both cell-to-cell contact and secretion of soluble factors (PGE2, TGF-β1, IL-6 and hepatocyte growth factor (HGF)). Specifically, in the allogeneic setting, MSCs induce T-cell anergy, reduce dendritic cell type 1 (DC1) TNF-α secretion, increase DC2 IL-10 secretion, decrease T-helper cell type 1 (Th1) IFN-γ secretion, increase Th2 IL-4 secretion, increase the proportion of regulatory T-cells (Treg) and decrease natural killer (NK) cell IFN-γ secretion. Furthermore, previous studies have demonstrated the ability of MSCs to reconstitute all heart valve layers, making them a potentially ideal source for recellularization of a tissue engineered heart valve scaffold. Finally, MSCs exhibit multipotent capacity, autologous availability, clinical relevance and increased proliferative capacity compared to terminally differentiated cells. Recellularizaton with MSCs complements antigen removal in producing an immunologically-acceptable, recellularized tissue scaffold.

As appropriate, in vitro co-culture conditions can, in specific embodiments, be under static conditions for cell culture or can take place in a bio-reactor mimicking certain desired in vivo conditions. As mentioned above, processed tissue can, in some embodiments, be treated with growth factors (e.g., basic fibroblast growth factor) or chemokines to enhance cellular ingrowth/migration into the tissue and/or to direct cells to adopt appropriate phenotypes. Such treatments could be employed to enhance in vitro recellularization before implantation of the recellularized tissue scaffold or ECM or to enhance in vivo recellularization after implantation of the tissue scaffold and/or decellularized ECM, and would be familiar to the ordinarily skilled artisan.

In further embodiments, the tissue scaffolds and/or decellularized ECM can be treated or impregnated with agents, e.g., growth factors and/or pharmaceuticals. Growth factors may, for example, be used to promote recellularization, vascularization, or epithelialization. Antibodies or antibiotics may be used to prevent potential infection from implant. Matrix components may also be used. Other so-called recellularization agents include, without limitation, chemoattractants, cytokines, chemokines, and derivatives thereof.

3. Decellularization and Antigen Removal from Muscle Tissue

In embodiments where the tissue is a muscle tissue, e.g., cardiac muscle tissue, striated or skeletal muscle tissue, or smooth muscle tissue, the methods can further comprise the steps of relaxing the muscle tissue and washing the muscle tissue in a concentrated salt solution to disassemble and remove the sarcomeric components.

Muscle tissue, including cardiac muscle tissue, contains four main cell types: endothelial cells, fibroblasts, myocytes and smooth muscle cells. Cardiomyocytes have the highest percentage in volume of myocardium. Cardiomyocytes, as well as myocytes in striated or skeletal muscle tissue, are made up of sarcomeres aligned in series and in parallel. Since actin filaments represent an important component of the sarcomere structure, we investigated the addition of an actin depolymerization step (e.g., utilizing swinholide, mycalolide B, Latrunculin B and/or Cytochalasin D) to convert filamentous cytoskeletal (cortical) and α-sarcomeric actin (F-actin) to globular actin monomers (G-actin). Conversion of F-actin to G-actin monomers increased solubility and therefore the removal of actin monomers, associated cytoskeletal proteins and antigens. Actin depolymerization alone was insufficient to facilitate complete solubilization of all macromolecular components of the sarcomere. An integrated multimodal approach is employed that complements the actin depolymerization step with additional steps specifically targeted to remove sarcomeric myosin and titin. Bathing muscle tissue in a basic "relaxing solution" designed to render the myosin heads on the sarcomeric apparatus in the relaxed state (e.g., switched from the ADP-bound or "rigor state" to the ATP-bound or relaxed state) prior to the antigen removal improved removal of sarcomeric proteins and associated antigens from the resulting scaffold. In varying embodiments, antigen removal and decellularization of muscle tissue comprises the step of relaxation of the muscle tissue prior to the antigen removal process, followed by removal of lipid-soluble proteins/antigens, sarcomeric depolymerization and removal of specific sarcomeric constituents, and finally removal of water-soluble proteins/antigens. In varying embodiments, antigen removal and decellularization of muscle tissue comprises the step of relaxation of the muscle tissue prior to the antigen removal process, followed by sarcomeric depolymerization and removal of specific sarcomeric constituents, removal of water-soluble proteins/antigens and finally removal of lipid-soluble proteins/antigens. This multi-targeted approach results in successful removal of essentially all detectable macromolecular sarcomeric components and has a significant impact on removal of both sarcomere-associated, and non-sarcomere-associated antigens from the material.

a. Relaxation of Muscle Tissue

The muscle tissue is contacted with (e.g., submerged in or perfused with) a relaxing solution comprising an energy source molecule under sufficient conditions and for a sufficient time to render the myocyte sarcomere structure (e.g., the functional rigid force-producing units that make up myocytes) amenable to subsequent disassembly and solubilization. In the relaxation step, a substantial portion of the myosin heads on the sarcomeric apparatus are switched from the ADP-bound or "rigor state" to the ATP-bound or relaxed state. In varying embodiments, the energy source molecule is selected from the group consisting of a nucleotide 5'-triphosphate (NTP), adenosine, inosine, aspartate, glutamate, creatine phosphate, a Kreb's cycle precursor or intermediate, glucose, and dextrose. In some embodiments, the energy source molecule is pyrophosphate (PPi) or a nucleotide 5'-triphosphate (NTP) selected from the group consisting of adenosine 5'-triphosphate (ATP), inosine 5'-triphosphate (ITP), guanidine 5'-triphosphate (GTP), cytidine 5'-triphosphate (CTP), and uridine 5'-triphosphate (UTP). In some embodiments, the energy source molecule is a precursor of adenosine 5'-triphosphate (ATP). In some embodiments, the energy source molecule is adenosine 5'-triphosphate (ATP). In some embodiments, the energy source molecule is Pyrophosphate (PPi). In some embodiments, the energy source molecule comprises vanadate and adenosine 5'-diphosphate (ADP).

In varying embodiments, the relaxing solution comprises each of the one or more energy source molecules in a concentration range of about 1 mM to about 200 mM, e.g., about 1 mM, 2 mM, 3 mM, 4 mM, 5 mM, 6 mM, 7 mM, 8 mM, 9 mM, 10 mM, 25 mM, 50 mM, 75 mM, 100 mM, 125 mM, 150 mM, 175 mM, or 200 mM. In varying embodiments, the relaxing solution comprises 4 mM adenosine 5'-triphosphate (ATP). In varying embodiments, the relaxing solution comprises 50-200 mM glucose, glutamate and/or aspartate.

In varying embodiments, the relaxing solution is a physiologically isotonic aqueous solution. In some embodiments, the relaxing solution promotes disassembly of sarcomeric macromolecules as well as the solubilization of water soluble antigens, as described above in the section entitled "Solubilizing Water-Soluble Antigens in the Tissue," further comprising one or more energy source molecules.

In various embodiments, the tissue is submerged in or perfused with the relaxing solution for at least about 0.5, 1, 2, 4, 6, 8, 10, 12, 14, 16, 18, 20, 22 or 24 hours, e.g., for at least about 2, 3, 4, 5, 6, 7 days, as appropriate. The tissue may be washed one or more times during the time period of submerging or perfusing, e.g., to promote disassembly of sarcomeric components within the muscle tissue.

In various embodiments, relaxation of the muscle tissue is performed at a temperature above freezing (e.g., above 0° C.) and at or below body temperature (e.g., at or below about 37° C.). In various embodiments, relaxation of the muscle tissue is performed at a refrigerated temperature, e.g., between about 4-10° C. In various embodiments, relaxation of the muscle tissue is performed at room temperature, e.g., between about 20-30° C., e.g., about 25° C. In various embodiments, relaxation of the muscle tissue is performed at human body temperature, e.g., about 37° C.

In some embodiments, the relaxing solution further comprises a calcium ion chelating agent. Illustrative chelation agents include, without limitation, ethylenediaminetetraacetic acid (EDTA), diethylenetriaminepentaacetic acid (DTPA), Citric Acid, N,N-bis(carboxymethyl)glycine (NTA), and the meso isomer of Dimercaptosuccinic acid (DMSA). In some embodiments, the relaxing solution further comprises a permeabilization agent. In varying embodiments, the permeabilization is a detergent, e.g, as described above and herein. Illustrative detergents for use as permeabilization agents include without limitation, e.g., Triton-X-100, saponin and/or a sulfobetaine (e.g., ASB-14).

In a particular embodiment, the relaxing solution comprises one or more cytoskeletal destabilizing agents in a solution comprising 10 mM TrisHCl, pH 7.6; 0.12 M KCl; 4 mM $MgCl_2$ $6H_2O$; 4 mM EDTA (hydrated) and 4-6 mM energy source molecule (e.g., Na-ATP or ATP)). In varying embodiments, the relaxing solution may further comprise a protease inhibitor and one or more antimicrobial agents, e.g., 0.5 mM AEBSF (4-(2-Aminoethyl)benzenesulfonyl fluoride hydrochloride) ("PEFABLOC™") and 1% Antibiotic Antimycotic Solution (AAS).

b. High Salt Concentration Wash to Facilitate Removal of Sarcomeric Components

In varying embodiments, the muscle tissue is exposed to (e.g., submerged in or perfused with) a concentrated salt solution to facilitate the solubilization and removal of sarcomeric components. In varying embodiments, the concentrated salt solution comprises one or more salts in a concentration range from about 0.5 M to about 3.0 M, e.g., about 0.6 M, 0.7 M, 0.8 M, 0.9 M, 1.0 M, 1.1 M, 1.2 M, 1.3 M, 1.4 M, 1.5 M, 1.6 M, 1.7 M, 1.8 M, 1.9 M, 2.0 M, 2.1 M, 2.2 M, 2.3 M, 2.4 M, 2.5 M, 2.6 M, 2.7 M, 2.8 M, 2.9 M, or 3.0 M. In some embodiments, the concentrated salt solution comprises one or more metal halide salts. In some embodiments, the metal halide salt is selected from the group consisting of LiF, LiCl, LiBr, LiI, NaF, NaCl, NaBr, NaI, KF, KCl, KBr, KI, RbF, RbCl, RbBr, RbI, CsF, CsCl, CsBr, CsI, $BeF_2$, $BeCl_2$, $BeBr_2$, $BeI_2$, $MgF_2$, $MgCl_2$, $MgBr_2$, $MgI_2$, $CaF_2$, $CaCl_2$, $CaBr_2$, $CaI_2$, $SrF_2$, $SrCl_2$, $SrBr_2$, $SrI_2$, $BaF_2$, $BaCl_2$, $BaBr_2$, $BaI_2$, and mixtures thereof. In some embodiments, the concentrated salt solution comprises KCl and/or KI. In some embodiments, the tissue is concurrently exposed to KCl and KI, and the concentrated salt solution comprises 0.6 M KCl and 1.0 M KI. In varying embodiments, the tissue is sequentially exposed to KCl and KI, e.g., first 0.6 M KCl and then 1.0 M KI or first 1.0 M KI and then 0.6 M KCl. The tissue can be washed in an isotonic solution between exposure to the high concentration salt solutions. As appropriate, the high concentration salt solution may further comprise a protease inhibitor and one or more antimicrobial agents, e.g., 0.5 mM AEBSF (4-(2-Aminoethyl)benzenesulfonyl fluoride hydrochloride) ("PEFABLOC™") and 1% Antibiotic Antimycotic Solution (AAS).

In varying embodiments, the muscle tissue is submerged in or perfused with the concentrated salt solution. In some embodiments, the muscle tissue is washed or rinsed with the concentrated salt solution. In some embodiments, the relaxing solution, described above, comprises one or more salts at a high concentration. In varying embodiments, the muscle tissue is contacted with the concentrated salt solution after exposure to the relaxing solution.

In some embodiments, sarcomeric constituents are not detectable in the muscle tissue. In some embodiments, at least about 90% of the sarcomeric constituents are removed, e.g., at least about 93%, 95%, 97%, 98%, 99% or all (100%) sarcomeric constituents are removed.

4. Tissue Scaffolds and/or Decellularized Extracellular Matrix (ECM)

Removing antigen components from tissue by sequentially immersing the tissue in separate solutions for depolymerizing and/or destabilizing one or more cytoskeletal components, solubilizing water soluble antigen components and for solubilizing lipid soluble antigen components produces tissue scaffolds and/or decellularized extracellular matrix (ECM) with biophysical and biochemical properties substantially the same as the tissue before it is subject to antigen removal. The produced tissue scaffolds and/or decellularized extracellular matrix (ECM) moreover have low residual antigenicity (e.g., to an allogeneic or xenogeneic host), and do not elicit significant or destructive immune responses by the host against the tissue scaffolds and/or decellularized extracellular matrix (ECM). The tissue scaffolds and/or decellularized extracellular matrix (ECM) produced according to the methods described herein are also non-toxic to live cells and suitable for repopulation and/or recellularization with live cells, e.g., that are allogeneic or xenogeneic to the tissue scaffolds and/or decellularized extracellular matrix (ECM).

With respect to residual antigenicity, the tissue scaffolds and/or decellularized extracellular matrix (ECM) that have been subject to sequential solubilization procedures for removal of water-soluble and lipid-soluble antigenic components are substantially depleted of water soluble and lipid soluble antigen components. In various embodiments, at least about 80%, for example, at least about 85%, 90%, 93%, 95%, 97%, 99%, or more, of the water soluble antigens are removed from the tissue to produce the present tissue scaffolds and/or decellularized extracellular matrix (ECM) (e.g., the residual antigenicity of water-soluble antigens is less than about 20%, e.g, less than about 15%, 10%, 7%, 5%, 3%, 1%, or less). In some embodiments, at least about 60%, for example, at least about 65%, 70%, 75%, 80%, 85%, 90%, 93%, 95%, 97%, 99%, or more, of the lipid soluble antigens are removed from the tissue to produce the present tissue scaffolds and/or decellularized extracellular matrix (ECM) (e.g., the residual antigenicity of lipid-soluble antigens is less than about 40%, e.g, less than about 35%, 30%, 25%, 20%, 15%, 10%, 7%, 5%, 3%, 1%, or less). In various embodiments, the water-soluble and/or lipid soluble antigen components are not detectable in the produced tissue scaffolds and/or decellularized extracellular matrix (ECM). The presence and/or amount of water-soluble and/or lipid soluble antigen components remaining in the tissue scaffolds and/or decellularized extracellular matrix (ECM) after performing antigen removal can be detected using methods known in the art, e.g., in vitro and/or in vivo immunoassays, Western blotting, ELISA, gel electrophoresis, lymphocyte proliferation and/or migration assays, etc.

For determination of residual antigenicity in vivo, tissue scaffolds and/or decellularized ECM produced according to the methods described herein (e.g., repopulated or not repopulated with live cells) can be implanted subcutaneously in a host that is allogeneic or xenogeneic to the tissue scaffold or decellularized ECM. Post-implantation development of scaffold calcification, innate (histologic assessment), humoral (biomaterial specific IgG positivity, C4d deposition) and cell-mediated (IHC for CD4/CD8/Treg subtyping, lymphocyte proliferation and migration assays) immune responses can be assessed and compared to both positive (native tissue) and clinically relevant negative control tissue (e.g., native allograft heart muscle tissue/patch, glutaraldehyde-fixed tissue). Such assays are known in the art. In various embodiments, the produced tissue scaffolds and/or decellularized extracellular matrix (ECM) do not elicit a detectable immune response, e.g., by lymphocytes allogeneic or xenogeneic to the tissue scaffold and/or ECM as measured in in vitro and/or in vivo assays. In various embodiments, the produced tissue scaffolds and/or decellularized extracellular matrix (ECM) elicit a detectable but insignificant and/or non-destructive immune response, e.g., by lymphocytes allogeneic or xenogeneic to the tissue scaffold and/or ECM as measured in in vitro or in vivo assays. In various embodiments, the produced tissue scaffolds and/or decellularized extracellular matrix (ECM) have a residual antigenicity and elicit an immune response that is equal to or less than the immune response of a negative control tissue (e.g., native allograft heart muscle tissue/patch, glutaraldehyde-fixed tissue).

With respect to biophysical properties, the tissue scaffolds and/or decellularized extracellular matrix (ECM) produced according to the present methods retain structure and strength that are not significantly different from or are substantially the same as the tissue before it is subject to antigen removal, e.g., by sequential solubilization of water-soluble and lipid-soluble antigen components. For example, the matrix morphology or structural integrity of the tissue scaffolds and/or decellularized extracellular matrix (ECM) is substantially intact—not significantly collapsed, degraded, shrunken, buckled, twisted or otherwise deformed. The size, e.g., length, width, thickness and/or volume, of the tissue scaffolds and/or decellularized extracellular matrix (ECM) are not significantly different from or are substantially the same as the tissue before it is subject to antigen removal. The structure of the tissue scaffolds and/or decellularized ECM produced according to the present methods retain a size, shape and structural integrity that is not significantly different from or is substantially the same as the tissue before it is subject to antigen removal. The structural integrity of the produced tissue scaffolds and/or decellularized ECM can be determined using any method in the art, e.g., including histology and electron microscopy (e.g., transition electron and/or scanning electron microscopy). See, e.g., Williams, et al., *Acta Biomater*. (2009) 5(4):993-1005; Zou and Zhang, *J Surg Res*. (2011) PMID 21571306. Histology techniques can be utilized to assess tissue morphology, residual nuclei counts (e.g., Hematoxylin and Eosin (H&E) staining), and gross ECM structure (e.g., Verhoeff-van Gieson staining) Collagen fiber orientation, mean fiber diameter and percent volume can be evaluated using electron microscopy. The tissue scaffolds and/or decellularized extracellular matrix produced according to the present methods moreover retain tensile properties, e.g., as measured by Young's modulus, tensile stress, and tensile strain parameters, that are not significantly different from or are substantially the same as the tissue before it is subject to antigen removal. Methods for determining biophysical properties of a tissue, before and after antigen removal, are known in the art and find use. For example, the size and/or volume of a sample of tissue can be determined before and after antigen removal, e.g., using a calipers. Methods for determining Young's modulus, tensile stress, and/or tensile strain of a tissue are also known in the art and find use. Illustrative methods are described, e.g., in Wong, et al, *Biomaterials*. (2011) 32:8129-8138; Ling Y. *AMP J. Tech.* (1996) 5:37-48; Sheridan, et al., *J Mech Behav Biomed Mater*. (2012) 8:58-70; Williams, et al., *Acta Biomater*. (2009) 5(4): 993-1005; Zou and Zhang, *J Surg Res.* (2011) PMID 21571306; and Petersen, et al., *Cells Tissues Organs*. (2012) 195(3):222-31.

With respect to biochemical properties, the tissue scaffolds and/or decellularized extracellular matrix (ECM) produced according to the present methods retain quantitative biochemical properties that are not significantly different from or are substantially the same as the tissue before it is subject to antigen removal, e.g., by sequential solubilization of water-soluble and lipid-soluble antigen components. For example, quantitative content (e.g., amounts and/or ratios) of water, elastin, collagen, glycosaminoglycans and/or proteoglycans is not significantly different or is substantially the same in tissues before and after antigen removal by the present methods. Methods for quantitative determination of biochemical properties of a tissue sample, e.g., content of water, elastin, collagen, glycosaminoglycans (GAG), proteoglycans, and/or other ECM components, are known in the art and find use. Illustrative methods are described, e.g., in Wong, et al, *Biomaterials*. (2011) 32:8129-8138; Williams, et al., *Acta Biomater*. (2009) 5(4):993-1005; Petersen, et al., *Cells Tissues Organs*. (2012) 195(3):222-31 and Woessner. *Arch Biochem Biophys* (1961) 93:440e7. Assay kits for determining the content of collagen, elastin, proteoglycans and/or GAG find use and are commercially available, e.g., from Biocolor Ltd. (on the internet at biocolor.co.uk), Worthington Biochemical Corp. (on the internet at worthington-biochem.com), Sigma-Aldrich (on the internet at sigmaaldrich.com), Quickzyme (on the internet at quickzyme.com), Kamiya Biomedical Company (on the internet at kamiyabiomedical.com) and Astarte Biologics (on the internet at astartebio.com).

With respect to live cell repopulation and/or recellularization, the tissue scaffolds and/or decellularized extracellular matrix (ECM) produced according to the present methods are suitable for repopulation or recellularization with live cells. Generally, the tissue scaffolds and/or decellularized ECM do not contain toxic contaminants or residue from the antigen removal process that are toxic to live cells and impede the ability of live cells to repopulate or recellularize the tissue scaffold or ECM. For example, in various embodiments, the tissues subject to sequential solubilization of water-soluble and lipid-soluble antigens for antigen removal are not contacted with sodium dodecyl sulfate (SDS). In various embodiments, the tissue scaffolds and/or decellularized extracellular matrix (ECM) produced according to the present methods are substantially repopulated with live cells, e.g., at least about 60%, 65%, 70%, 75%. 80%, 85%, 90%, 95%, 99%, or more, of capacity repopulated or recellularized. The extent of recellularization can be determined using any method in the art. Illustrative assays for assessing recellularizaton capacity include without limitation toxicity (e.g., LDH), adhesion (e.g., histology), viability (e.g., Live/Dead), migration (e.g., hMSC tissue invasion on histology and immunohistochemistry (IHC)), and proliferation (e.g., proliferating cell nuclear antigen antibody (PCNA)) assays. As appropriate and depending on tissue to be recellularized and cell/donor availability, the tissue scaffolds and/or decellularized ECM can be repopulated and/or recellularized with cells autologous to the recipient of the tissue; allogeneic to the recipient of the tissue; cells of the same tissue type as the tissue to be transplanted into the recipient; mesenchymal stem cells; and mixtures thereof.

Tissue scaffolds and/or decellularized ECM produced according to the methods described herein have application in processing and implantation of bioprostheses, biomaterials, or xenogeneic tissues (xenografts) including, e.g., heart valves, vascular conduits, arteries, veins, skin, dermis, ligaments, tendons, bone, cartilage, muscle, ureter, urinary bladder, liver, heart, and other organs; or processing and transplantation of fresh, preserved, or banked allogeneic tissues (allografts) including vessels, vascular conduits, arteries, veins heart valves, skin, dermis ligaments, tendons, bone, cartilage, muscle, ureter, urinary bladder, liver, heart, or other organs; or the development of natural biological matrices for tissue-engineered tissues and organs including heart valves, vessels, skin, dermis, ligaments, bone, cartilage, muscle, ureter, urinary bladder, liver, heart, or other organs.

In various embodiments, the tissue scaffolds and/or decellularized ECM can be used as implants, tissue fillers, burn dressings, wound dressings, blood vessel grafts, blood vessel replacements, and the like. Medical graft materials comprising the tissue scaffolds and/or decellularized ECM produced by sequential antigen removal methods can be used in the repair or reconstruction of tissues such as nervous tissue, dermal tissue (ex: in wound care), cardiovascular tissue (including vascular and cardiac), pericardial tissue, muscle tissue, bladder tissue, ocular tissue, periodontal tissue, bone, connective tissue (tendons, ligaments), and the like. Medical graft materials of the invention can also be used in conjunction with one or more secondary components to construct a medical device (e.g., a balloon-expandable or self-expanding stent).

Another application of a method according to the invention is to mitigate, reduce, inhibit and/or prevent immune rejection of transplanted tissues/organs between individuals within a species (i.e., allografts) or between species (i.e., xenografts) by the removal of antigens from the tissue/organ.

If the tissue scaffold and/or decellularized ECM is sterilized following the antigen removal procedure, it should have a shelf life of at least 1 year, or more.

5. Kits

The invention further provides kits comprising tissue scaffolds and/or decellularized ECM, e.g., as described herein and/or produced according to the methods described herein. The kits may further comprise instructions for repopulation or recellularization of the tissue scaffolds and/or decellularized ECM with live cells. Generally, tissue scaffolds and/or decellularized ECM provided in such kits are sterilized and ready for transplantation into a host.

Also provided are kits for producing tissue scaffolds and/or decellularized ECM substantially depleted of antigenic components and suitable for live cell repopulation or recellularization. In some embodiment, the kits comprise a first container comprising a solution for solubilizing water-soluble antigens and a second container comprising a solution for solubilizing lipid-soluble antigens. In varying embodiments, the kits comprise a first container comprising a solution for depolymerizing one or more cytoskeletal components, a second container comprising a solution for solubilizing water-soluble antigens and a third container comprising a solution for solubilizing lipid-soluble antigens. The embodiments of the solutions for depolymerizing one or more cytoskeletal components, for solubilizing water-soluble antigens and for solubilizing lipid-soluble antigens are described above and herein. In varying embodiments, the kits may further comprise a container comprising a relaxing solution and a container comprising a concentrated salt solution. The embodiments of the relaxing solution and the concentrated salt solution are described above and herein. The kits may further comprise instructions for removing antigenic components from a tissue, e.g., a muscle tissue. In various embodiments, the kits also comprise a control tissue scaffold and/or decellularized ECM, e.g., that has been processed employing sequential antigen removal and produced according to methods described herein.

EXAMPLES

The following examples are offered to illustrate, but not to limit the claimed invention.

Example 1

Stepwise Solubilization-Based Antigen Removal for Xenogeneic Scaffold Generation in Tissue Engineering Materials and Methods Tissue harvest. All chemicals were from Sigma-Aldrich (St. Louis, Mo.) unless otherwise stated. Fresh BP was harvested from adult cattle as previously described [Wong, et al., *Biomaterials* (2011) 32:8129-38] (n=3).

Antiserum Production.

All animal procedures were conducted in accordance with the guidelines established by University of California, Davis IACUC and the Guide for the Care and Use of Laboratory Animals [National Research Council Institute of Laboratory Animal Resources Commission on Life Sciences. Guide for the Care and Use of Laboratory Animals. Washington, D.C.: National Academy Press; 1996]. Anti-native BP serum was generated from New Zealand white rabbits (n=4) as previously described [Griffiths, et al., *Biomaterials* (2008) 29:3514-20; Wong, et al., *Biomaterials* (2011) 32:8129-38; Griffiths, et al., *Electrophoresis* (2008) 29:4508-15]. Briefly, following subcutaneous injection of BP homogenate and Freund's adjuvant at a 1:1 ratio into New Zealand white rabbits (n=4) on days 0, 14 and 28, blood was collected at day 84. Serum was isolated following centrifugation at 3000 rpm for 10 min and stored at −80° C. until used on Western blots (Section 2.4).

Protein Extraction.

Protein extraction from minced BP-AR was adapted from a method described previously [Wong, et al., *Biomaterials* (2011) 32:8129-38; Griffiths, et al., *Electrophoresis* (2008) 29:4508-15]. All centrifugation steps were performed at 17,000 g, 4° C. for 25 min. Briefly, minced BP-AR was incubated in standard extraction solution (10 mM Tris-HCl (pH 8.0) containing 1 mM dithiothreitol, 2 mM magnesium chloride hexahydrate, 10 mM potassium chloride and 0.5 mM Pefabloc SC (Roche, Indianapolis, Ind.)) containing 0.1% (w/v) SDS (Bio-Rad, Hercules, Calif.) at 1000 rpm, 4° C. for 1 h. Following centrifugation, recovered supernatant was defined as residual hydrophilic protein extract. The insoluble pellet was washed twice in standard extraction solution containing 0.1% (w/v) SDS at 1400 rpm, 4° C. for 30 min and then incubated in standard extraction solution containing 1% (w/v) SDS at 1400 rpm, 4° C. for 1 h. Following centrifugation, recovered supernatant was defined as residual lipophilic protein extract. All extracts were stored at −80° C.

One-Dimensional Electrophoresis and Western Blot.

One-dimensional electrophoresis and Western blot was performed as previously described [Wong, et al., *Biomaterials* (2011) 32:8129-38], using equal volumes of residual hydrophilic or lipophilic protein extract per group.

Antigen Removal.

Antigen removal was adapted from a method previously described [Wong, et al., *Biomaterials* (2011) 32:8129-38]. All steps were performed in a 2 ml working volume at 4° C. and 125 rpm unless otherwise stated. Briefly, intact pieces of BP (0.2 g, approximately 1.0 cm×1.5 cm) were subjected to hydrophile solubilization for 2 days as the first step of AR. This was followed by lipophile solubilization at room temperature for 2 days as the second step of AR. For each AR sample, an anatomically adjacent piece of BP subjected to AR for 1 min served as a negative AR control for biological tissue variability and effects of AR additives. Following nucleic acid digestion for 24 h and washout for 48 h, BP-AR was stored in Dulbecco's modified Eagle's medium with 15% (v/v) dimethyl sulfoxide at −80° C. All AR experiments were conducted with n=6 per group.

Effect of Hydrophile Solubilization (One-Step AR).

Residual lipophilic antigenicity of BP-AR was assessed after hydrophile solubilization with either basic AR buffer (BARB; 10 mM Tris-HCl (pH 8.0) containing 0.5 mM Pefabloc and 1% (v/v) antibiotic antimycotic solution) or optimized solubilizing AR buffer (opt SARB; BARB containing 100 mM dithiothreitol, 2 mM magnesium chloride hexahydrate and 100 mM potassium chloride) containing: no additional additive, 134 mM 3-(benzyldimethylammonio) propanesulfonate (NDSB-256) or 0.1% (w/v) SDS.

Effect of Sequential Hydrophile and Lipophile Solubilization (Two-Step AR).

Both residual hydrophilic and lipophilic antigenicity of BP-AR were assessed after two-step AR (FIG. 1). Pieces of BP underwent hydrophile solubilization with opt SARB, followed by lipophile solubilization in opt SARB containing: no additional additive; 134 mM NDSB-256 and 1% (w/v) n-dodecyl-β,D-maltoside (Griffiths solution) [Griffiths, et al., *Biomaterials* (2008) 29:3514-20; Griffiths, et al., *Electrophoresis* (2008) 29:4508-15]; 8 M urea (Bio-Rad), 2 M thiourea, 2% (w/v) 3-[(3-cho-lamidopropyl)dimethylammonio]-1-propanesulfonate (CHAPS), 2% (w/v) N-decyl-N,N-dimethyl-3-ammonio-1-propanesulfonate (SB 3-10) and 1% (w/v) 3-[N,N-Dimethyl(3-myristoylaminopro-pyl)ammonio]propanesulfonate (ASB-14) (Cordwell solution) [Cordwell, *Methods Mol Biol* (2008) 424:139-46]; or 10% (v/v) isopropanol (Thermo Fisher Scientific) and 5% (v/v) glycerol (Leimgruber solution) [Leimgruber R M. "Extraction and solubilization of proteins for proteomic studies," In: Walker J M, editor. *The Proteomics Protocols Handbook*. Totowa: Humana Press; (2005) pp. 1-18]. These samples were compared to a literature control of BARB containing 0.1% (w/v) SDS for hydrophile solubilization, followed by 1% (w/v) SDS for lipophile solubilization [Griffiths, et al., *Electrophoresis* (2008) 29:4508-15].

Effect of Cordwell Solution Components.

Residual lipophilic antigenicity of BP-AR was assessed after hydrophile solubilization with opt SARB, followed by lipophile solubilization in opt SARB containing: no additional additive; 8 M urea and 2 M thiourea; 2% (w/v) CHAPS; 2% (w/v) SB 3-10; 1% (w/v) ASB-14; or the entire Cordwell solution during the second step of AR.

Assessment of residual antigenicity following AR. Assessment of residual BP-AR antigenicity was performed using a method previously validated [Griffiths, et al., *Biomaterials* (2008) 29:3514-20] and described [Wong, et al., *Biomaterials* (2011) 32:8129-38] on residual hydrophilic or lipophilic protein extracts (FIG. 1). Briefly, residual hydrophilic or lipophilic protein extracts (n=6 per group) were subjected to electrophoresis and Western blot, probed with anti-native BP serum and assessed for IgG positivity, with band intensity quantified by densitometry. Residual antigenicity of BP-AR was defined as the ratio of the banding intensity from 2 days of AR to that of the 1 min AR control. Residual antigenicity ratios for each AR treatment were then normalized to the negative AR control within each experiment (BARB for one-step AR or opt SARB alone for two-step AR).

Uniaxial Tensile Testing.

Tensile properties of BP were determined as previously described [Wong, et al., *Biomaterials* (2011) 32:8129-38]. Strips of BP (15×3 mm) were cut from separate 0.2 g pieces of native BP and BP-AR (n=6 per group) and made into dogbone shapes. Samples from adjacent anatomical locations were used for each replicate of AR treatment and control tissue. BP mounted under zero strain was subjected to a constant strain rate of 0.1 mm $s^{-1}$. The initial gauge length was set at 2 mm. The initial gauge width and thickness were determined from BP images using ImageJ 1.42q software (Wayne Rasband, National Institutes of Health, USA). For each sample, a stress—strain curve was generated from the load—elongation curve, and the Young's modulus and ultimate tensile stress (UTS) were determined.

Quantitative Biochemistry.

The ECM composition of native BP and BP-AR was determined as previously described [Wong, et al., *Biomaterials* (2011) 32:8129-38] from two 5 mm disks (taken from the initial 0.2 g piece, n=6 per group). One disk was subjected to papain digestion for quantification of collagen content per dry weight (DW) using a modified colorimetric hydroxyproline assay [Woessner, *Arch Biochem Biophys* (1961) 93:440-7] and sulfated glycosaminoglycan (GAG) content per DW using the Blyscan sulfated GAG assay (Biocolor Ltd., Carrickfergus, UK). The second disk was subjected to hot oxalic acid extraction for quantification of elastin content per DW using the Fastin elastin assay (Biocolor Ltd.).

Histology.

Histological assessment of native BP and BP-AR was performed as previously described [Wong, et al., *Biomaterials* (2011) 32:8129-38] from two 1 mm wide strips (taken from the initial 0.2 g piece, n=6 per group). Formalin-fixed, paraffin-embedded sections underwent Verhoeff van Gieson staining (VVG) for assessment of gross collagen and elastin organization and hematoxylin and eosin (H&E) staining Assessment of ECM fiber morphology was performed for all six replicates per AR treatment throughout the full thickness of the tissue (from the parietal surface to the mediastinal surface of the pericardium). Quantification of residual nuclei was performed on six randomized high-powered fields (HPFs) per slide. Correlation between nuclei counts and residual lipophilic antigenicity was determined by plotting average nuclei counts against residual lipophilic antigenicity for each AR method.

Immunohistochemistry.

Paraffin-embedded sections of native BP and BP-AR samples (n=6 per group) were deparaffinized in xylene (Fisher Scientific, Pittsburgh, Pa.) and rehydrated through an ethanol gradient. Endogenous peroxidase was quenched through incubation in per-oxidase block (Dako, Carpinteria, Calif., USA) for 5 min, followed by antigen retrieval using proteinase K (Dako) for 10 min. Slides were blocked in 5% normal goat serum (NGS) (Jackson ImmunoResearch Laboratories, Inc.) for 30 min and then incubated in primary antibody for 60 min. Following incubation in EnVision+ anti-mouse HRP-labelled polymer (Dako) for 30 min, bound primary antibodies were detected using EnVision+ DAB+ chromogen (Dako) for 10 min. Finally, slides were counterstained with Mayer's hematoxylin for 5 min, dehydrated through an ethanol gradient, cleared in xylene, mounted in Permount (Fisher Scientific) and coverslipped. The two primary antibodies used were anti-galactose-a(1,3)-galactose (a-gal) clone M86 (Enzo Life Sciences, Plymouth Meeting, Pa.) at a 1:5 dilution in 5% NGS and anti-major histocompatibility complex I (MHC I) heavy chain (Abcam, Cambridge, Mass.) at a 1:250 dilution in 5% NGS. Sections from all six replicates per AR treatment were assessed for the presence of α-gal and MHC I antigens throughout the full thickness of the tissue (from the parietal surface to the mediastinal surface of the pericardium).

Statistical Analysis.

Normalized residual antigenicity ratios were compared between experimental AR groups and the negative solubilization control (BARB for one-step AR and opt SARB alone for two-step AR). Values determined from tensile testing, biochemical assays and histology were compared to those for control tissues (native BP). Non-repeated measures analysis of variance and Tukey-Kramer HSD post hoc analysis were performed on sample means. Correlation was determined using bivariate fit analysis. All data are presented as mean±standard deviation from the mean. Statistical significance was defined at $p<0.05$.

Results

Antigen Removal

Effect of Hydrophile Solubilization (One-Step AR).

Promotion of hydrophile solubilization with opt SARB did not significantly change the residual lipophilic antigenicity of BP-AR compared to BARB for any of the additives assessed: no additional additive (0.86±0.14 vs. 1.00±0.51), 134 mM NDSB-256 (0.51±0.12 vs. 0.58±0.24) or 0.1% (w/v) SDS (0.35±0.12 vs. 0.42±0.03) (FIG. 2).

Effect of Sequential Hydrophile and Lipophile Solubilization (Two-Step AR).

Promotion of lipophile solubilization during a second step of AR with Griffiths, Cordwell or Leimgruber solution did not significantly change the residual hydrophilic antigenicity of BP-AR compared to opt SARB alone (0.79±0.28, 0.13±0.11, 0.72±0.27, 1.00±0.15, respectively) (FIG. 3A). However, use of opt SARB during the first of two AR steps reduced residual hydrophilic antigenicity significantly—by 75%—compared to that remaining following two-step AR with 0.1 and 1% (w/v) SDS in BARB (4.03±2.27, $p<0.0005$).

Promotion of lipophile solubilization during a second step of AR significantly decreased residual lipophilic antigenicity of BP-AR with respect to that treated with opt SARB alone (1.00±0.22) (FIG. 3B). Compared to the use of opt SARB alone, the percent reduction of residual lipophile antigenicity achieved was 44% with the Griffiths solution (0.66±0.14, $p<0.05$), 91% with the Cordwell solution (0.09±0.04, $p<0.0001$) and 33% with the Leimgruber solution (0.67±0.11, $p<0.05$). Use of 1% (w/v) SDS in BARB resulted in a 37% decrease in residual lipophilic antigenicity (0.63±0.15, $p<0.01$) compared to opt SARB alone. Furthermore, use of the Cordwell solution in opt SARB during the second step of AR significantly reduced residual lipophilic antigenicity by 54% compared to with 1% (w/v) SDS in BARB ($p<0.0001$).

Effect of Cordwell Solution Components.

Figure 4:
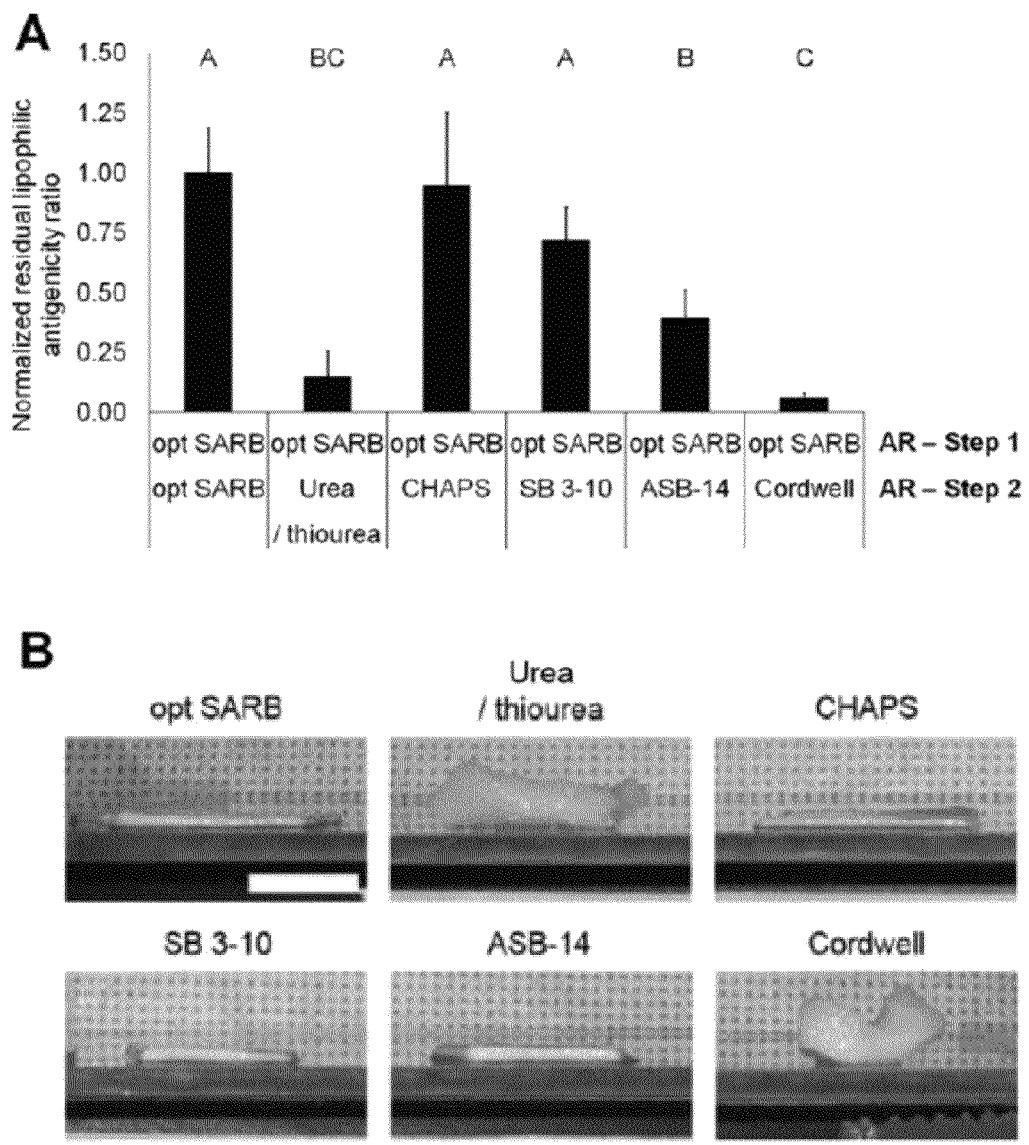
FIGS. 4A-B illustrate residual lipophilic antigenicity and gross morphology of bovine pericardium following two-step AR with either the entire Cordwell solution or its individual components. Use of opt SARB containing 8 M urea and 2 M thiourea, 1% (w/v) ASB-14 or the entire Cordwell solution significantly reduces residual lipophilic antigenicity compared to opt SARB alone (A). Results are plotted as mean±standard deviation. Groups not connected by the same letter are significantly different, $p<0.05$ (n=6 per group). Treatment with 8 M urea and 2 M thiourea in opt SARB or the entire Cordwell solution drastically changes gross tissue morphology (B). The scale bar represents 1 cm.

Promotion of lipophile solubilization during a second step of AR in opt SARB reduced the residual lipophilic antigenicity of BP-AR compared to that treated with no additional additive (1.00±0.19, p<0.0001) significantly—by 85% with 8 M urea and 2 M thiourea (0.15±0.11), 60% with 1% (w/v) ASB-14 (0.40±0.12) and 94% with the entire Cordwell solution (0.06±0.02) (FIG. 4A). However, treatment with 1% (w/v) ASB-14 in opt SARB did not reduce the residual lipophilic antigenicity of BP-AR to the level achieved with the entire Cordwell solution (p<0.05). The residual lipophilic antigenicity of BP-AR treated with opt SARB containing 8 M urea and 2 M thiourea was not significantly different from that achieved using either 1% (w/v) ASB-14 or the entire Cordwell solution.

Gross Tissue Morphology

Effect of Hydrophile Solubilization (One-Step AR).

No change in BP-AR thickness was observed following AR with opt SARB (containing no additional additive, 134 mM NDSB-256, or 0.1% (w/v) SDS) compared to BP-AR generated using BARB, 1 min AR controls or native BP.

Effect of Sequential Hydrophile and Lipophile Solubilization (Two-Step AR).

Figure 3:
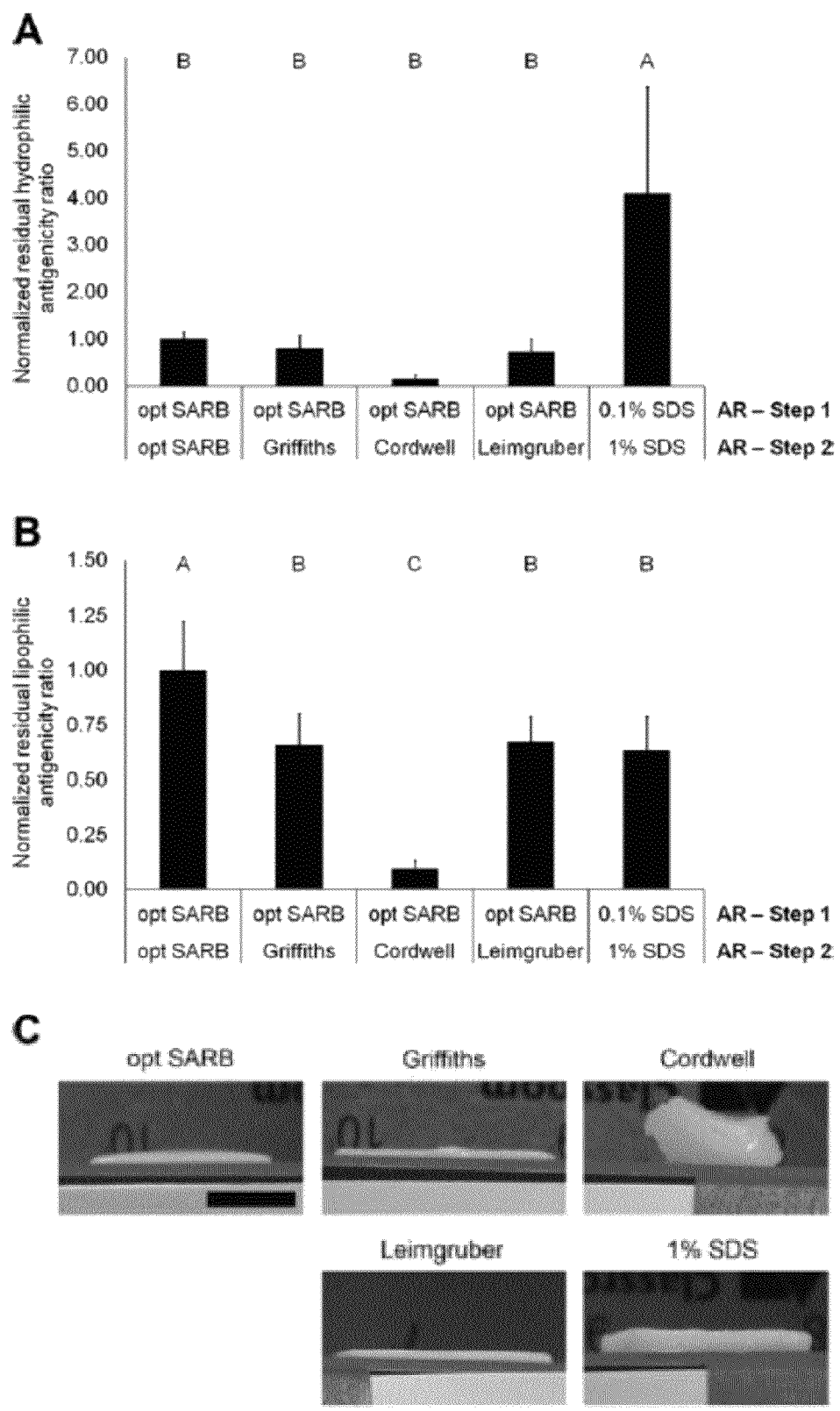
FIGS. 3A-C illustrate residual hydrophilic and lipophilic antigenicity and gross morphology of bovine pericardium following two-step AR. Hydrophilic antigenicity is not decreased further following addition of a lipophile solubilization step (A). Lipophilic antigenicity is significantly decreased following addition of lipophile solubilization (B). Results are plotted as mean±standard deviation. Groups not connected by the same letter are significantly different, $p<0.05$ (n=6 per group). Use of the Cordwell solution in opt SARB or 1% (w/v) SDS in BARB dramatically alters gross tissue morphology (C). The scale bar represents 1 cm.

Treatment with either 1% (w/v) SDS in BARB or the Cordwell solution during the second step of AR resulted in gross morphological thickening of BP-AR compared to that generated using opt SARB alone (FIG. 3C). Moreover, BP-AR subjected to the Cordwell solution curled upward, rather than remaining flat. No significant change in BP-AR thickness was observed following treatment with the Griffiths or Leimgruber solution.

Effect of Cordwell Solution Components.

Treatment with either 8 M urea and 2 M thiourea in opt SARB or the entire Cordwell solution during the second step of AR resulted in gross morphological thickening and curling of BP-AR compared to that generated using opt SARB alone (FIG. 4B). No significant change in BP-AR thickness was observed following treatment with opt SARB containing 2% (w/v) CHAPS, 2% (w/v) SB 3-10 or 1% (w/v) ASB-14.

Uniaxial Tensile Testing.

Figure 5:
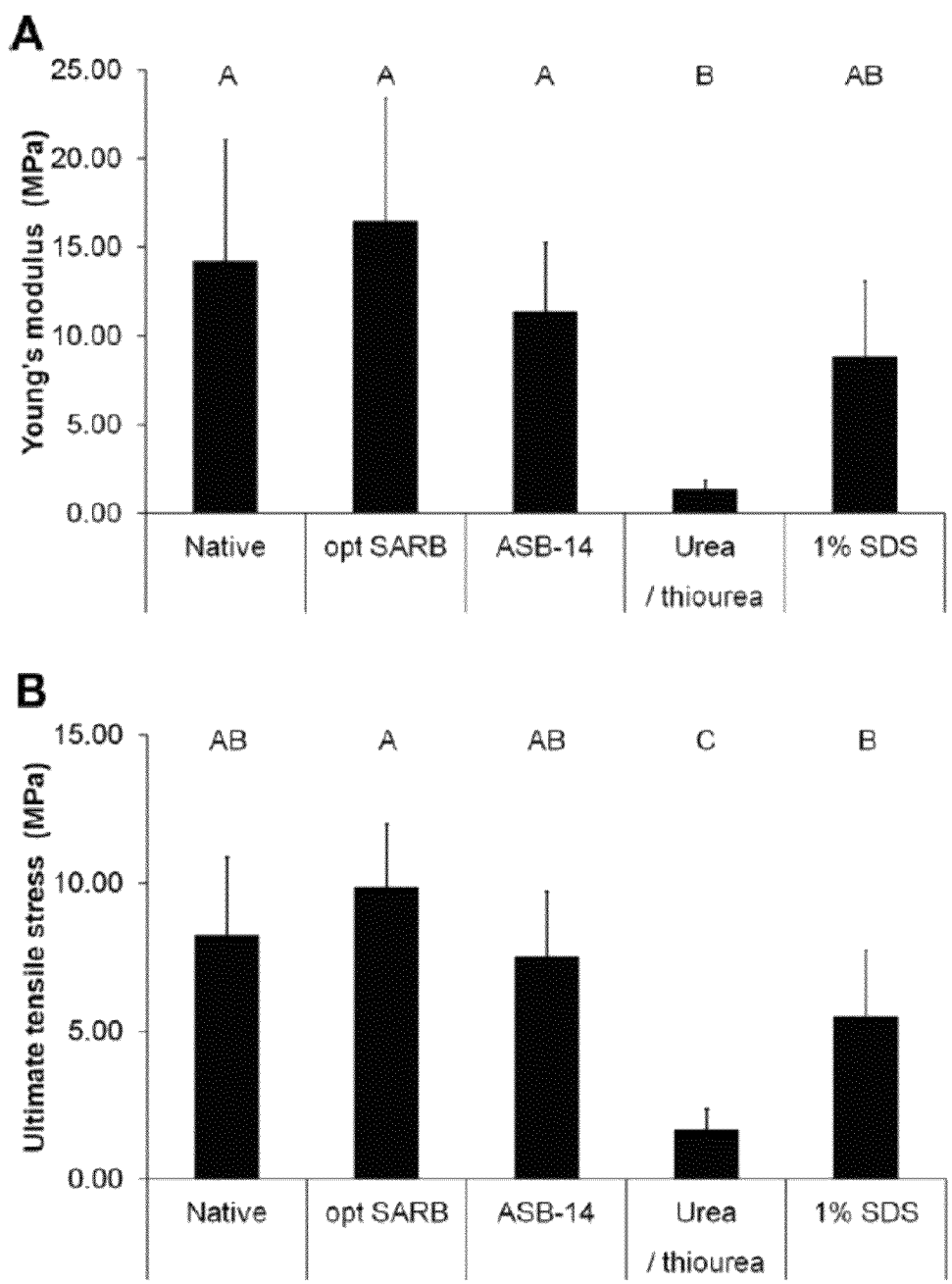
FIGS. 5A-B illustrate tensile properties of bovine pericardium (BP). Young's modulus (A) and UTS (B) of BP following two-step AR using no additive or 1% (w/v) ASB-14 in opt SARB, or 1% (w/v) SDS in basic AR buffer are not significantly different from those of native BP. A second step of AR using 8 M urea and 2 M thiourea in opt SARB results in a significant decrease in Young's modulus and UTS. Results are plotted as mean±standard deviation. Groups not connected by the same letter are significantly different, p<0.05 (n=6 per group).

No significant differences in Young's modulus and UTS were observed between native BP (14.25±6.87 and 8.25±2.64 MPa, respectively) and BP-AR generated with opt SARB alone (16.43±7.01 and 9.86±2.14 MPa, respectively), 1% (w/v) ASB-14 in opt SARB (11.36±3.94 and 7.52±2.22 MPa, respectively) or 1% (w/v) SDS in BARB (8.87±4.23 and 5.48±2.26 MPa, respectively) (FIG. 5). Use of 8 M urea and 2 M thiourea in opt SARB significantly decreased the Young's modulus and UTS (1.35±0.55 and 1.70±0.68 MPa, respectively) of BP-AR compared to native BP.

Quantitative Biochemistry.

Figure 6:
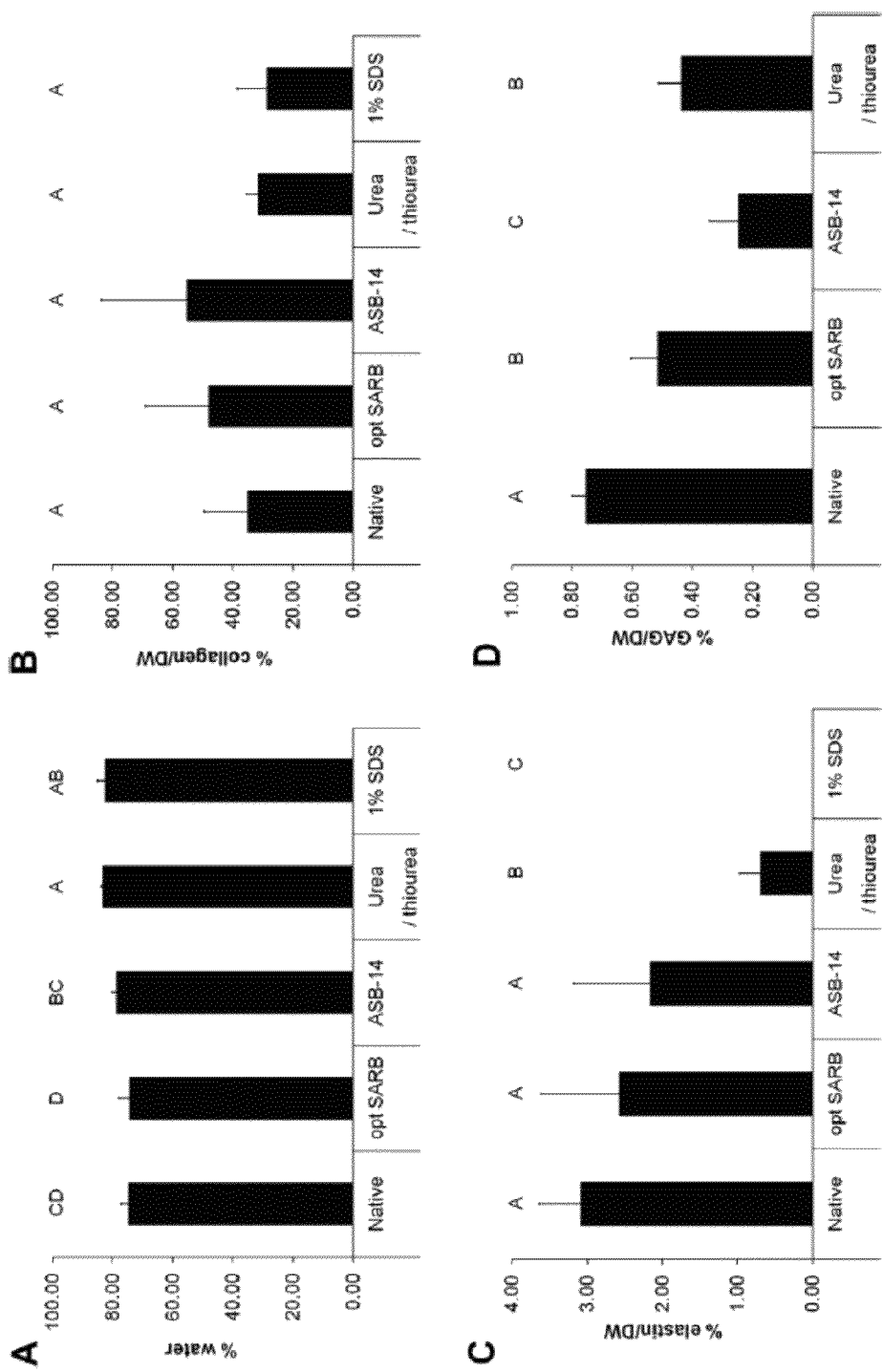
FIGS. 6A-D illustrate quantitative biochemical analysis of bovine pericardium (BP) composition. Water content is maintained following two-step AR in opt SARB containing no additional additive or 1% (w/v) ASB-14 compared to native BP (A). A second step of AR using either 8 M urea and 2 M thiourea in opt SARB or 1% (w/v) SDS in BARB significantly increases water content. The collagen content per dry weight (DW) is not significantly different following two-step AR compared to native BP (B). The elastin content per DW is maintained following two-step AR using opt SARB containing no additional additive or 1% (w/v) ASB-14 compared to native BP (C). Use of 8 M urea and 2 M thiourea in opt SARB significantly decreases the elastin content per DW. The elastin content per DW for samples treated with 1% (w/v) SDS in BARB is below the limit of detection of the assay. GAG content per DW is significantly decreased following two-step AR compared to native BP (D). Results are plotted as mean±standard deviation. Groups not connected by the same letter are significantly different, p<0.05 (n=6 per group).

The water content of BP-AR generated using opt SARB containing no additional additive (74.36±3.67%) or 1% (w/v) ASB-14 (78.74±1.39%) during the second step of AR was not significantly different from that of native BP (74.73±2.42%) (FIG. 6A). However, use of 8 M urea and 2 M thiourea in opt SARB (83.43±0.59) or 1% (w/v) SDS in BARB (82.61±2.58%) significantly increased the water content of BP-AR compared to that of native BP (p<0.0001).

The collagen content of BP-AR was not significantly different than that of native BP (34.98±14.75% per DW) following any of the tested lipophile solubilization treatments: opt SARB alone (48.10±21.07% per dry weight (DW)), 1% (w/v) ASB-14 in opt SARB (55.40±28.60% per DW), 8 M urea and 2 M thiourea in opt SARB (31.56±3.99% per DW) or 1% (w/v) SDS in BARB (28.75±9.73% per DW) (FIG. 6B).

The elastin content of BP-AR generated using opt SARB containing no additional additive (2.58±1.04% per DW) or 1% (w/v) ASB-14 (2.16±1.02% per DW) during the second step of AR was not significantly different from that of native BP (3.09±0.56% per DW) (FIG. 6C). However, use of 8 M urea and 2 M thiourea in opt SARB (0.70±0.27% per DW) significantly decreased the elastin content of BP-AR compared to that of native BP (p<0.0005). The elastin content of BP-AR generated using 1% (w/v) SDS in BARB was also significantly reduced, to a level below the limit of detection of the assay (p<0.0001).

The GAG content of BP-AR was significantly different from that of native BP (0.75±0.05% per DW) following treatment with opt SARB containing: no additional additive (0.52±0.09% per DW), 1% (w/v) ASB-14 (0.25±0.10% per DW) or 8 M urea and 2 M thiourea (0.44±0.08% per DW) during the second step of AR (p<0.0005) (FIG. 6D). The presence of residual SDS in BP-AR subjected to 1% (w/v) SDS in BARB during the second step of AR inter-fered with the Blyscan assay.

Histology.

Figure 7:
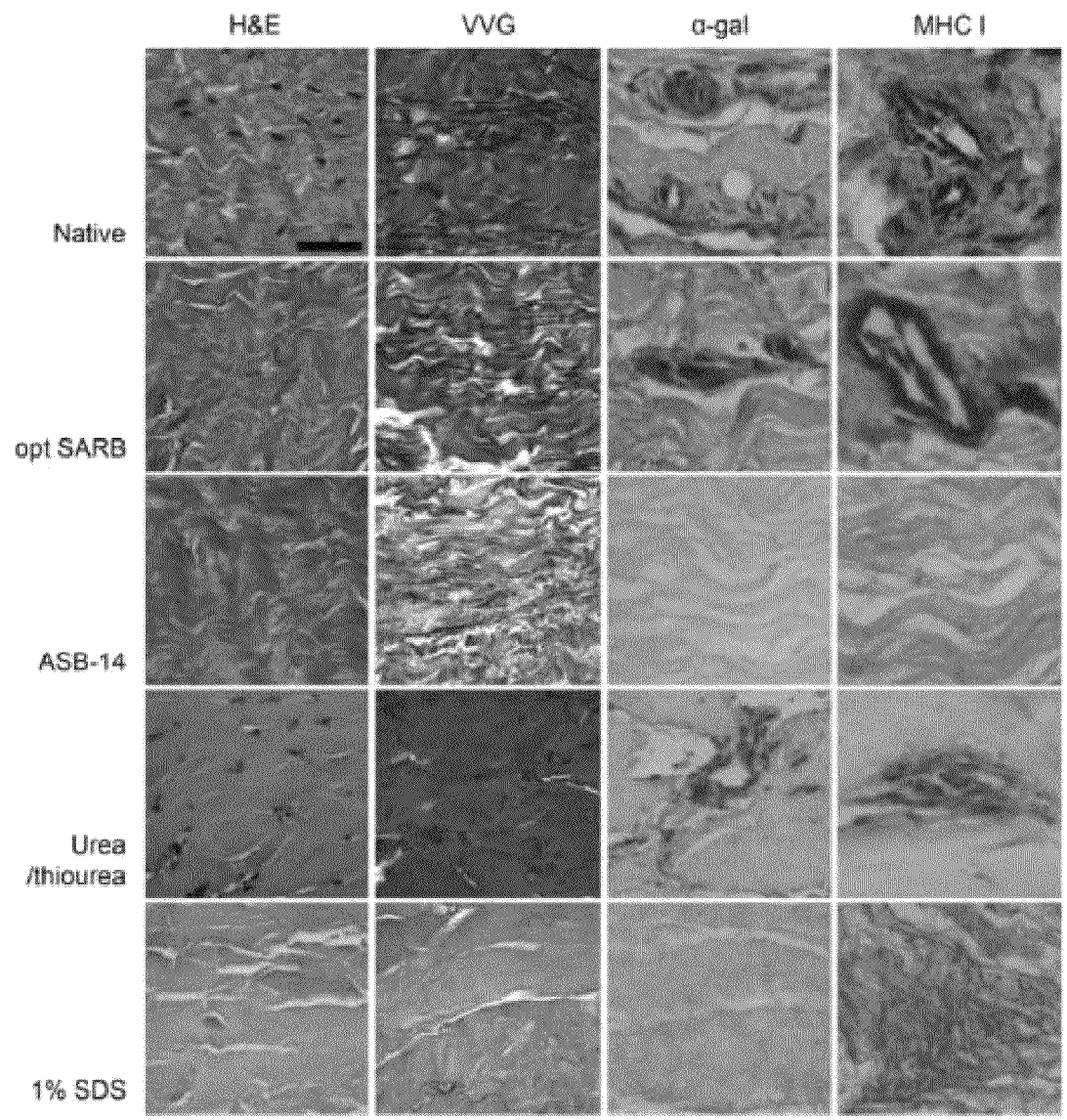
FIG. 7 illustrates gross histological morphology and residual known xenoantigens in representative images of bovine pericardium (BP). H&E staining reveals both preservation of histological ECM morphology and reduction in residual nuclei following two-step AR using 1% (w/v) ASB-14 in opt SARB. Treatment with 8 M urea and 2 M thiourea in opt SARB or 1% (w/v) SDS in BARB does not maintain histological ECM morphology. Verhoeff van Gieson staining indicates that gross collagen and elastin structure is preserved following two-step AR using no additive or 1% (w/v) ASB-14 in opt SARB for lipophile solubilization. Treatment with 8 M urea and 2 M thiourea in opt SARB or 1% (w/v) SDS in BARB does not maintain gross collagen and elastin organization. Immunohistochemical staining reveals that no α-gal antigens persist in BP treated with 1% (w/v) ASB-14 in opt SARB or 1% (w/v) SDS in BARB. Residual α-gal antigens are observed in BP subjected to no additive or 8 M urea and 2 M thiourea in opt SARB. Immunohistochemical staining indicates that no MHC I antigens persist in BP treated with 1% (w/v) ASB-14 in opt SARB. Residual MHC I antigens are observed in BP subjected to no additive or 8 M urea and 2 M thiourea in opt SARB or 1% (w/v) SDS in BARB. The scale bar represents 50 μm.

Qualitatively, no differences in collagen and elastin content and organization were observed between VVG-stained sections of native BP and BP-AR following a second step of AR in opt SARB containing no additional additive or 1% (w/v) ASB-14 (FIG. 7). However, BP-AR generated with 8 M urea and 2 M urea in opt SARB or 1% (w/v) SDS in BARB exhibited a marked loss of collagen fiber organization and elastin content. Minor differences in staining intensity were attributed to processing artifacts and not a change in collagen and elastin organization.

In H&E-stained BP sections, ECM morphology was grossly maintained following a second step of AR using no additive or 1% (w/v) ASB-14 in opt SARB compared to native BP (FIG. 7). However, treatment with 8 M urea and 2 M thiourea in opt SARB or 1% (w/v) SDS in BARB resulted in marked disruption of native ECM morphology.

Figure 8:
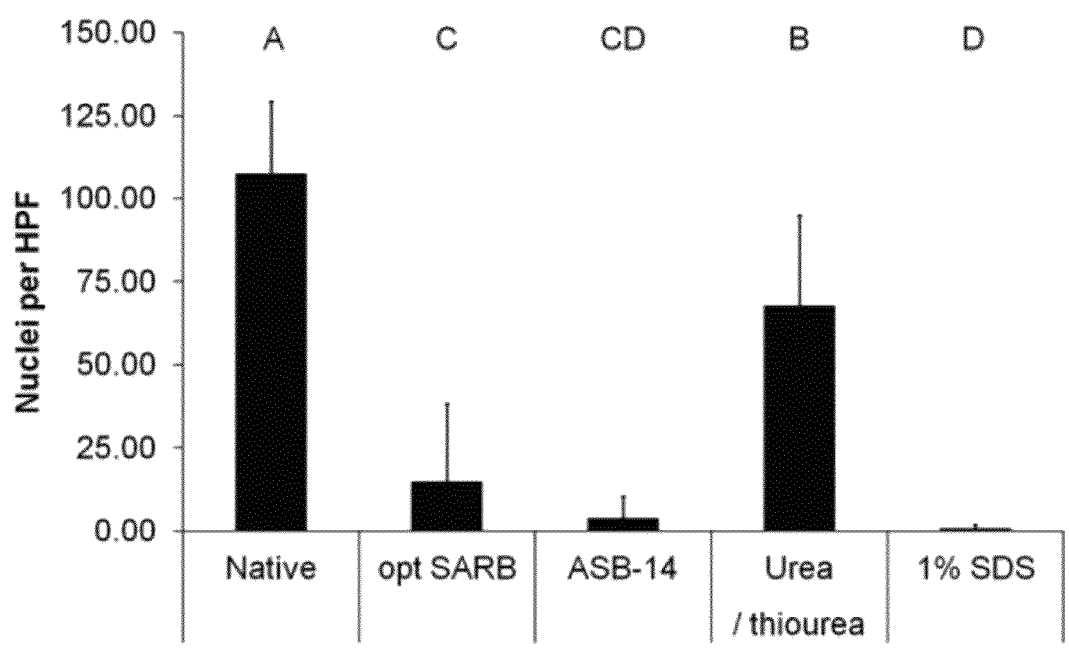
FIG. 8 illustrates residual nuclei per HPF in bovine pericardium (BP). Following two-step AR, 1% (w/v) ASB-14 in opt SARB or 1% (w/v) SDS in BARB reduces nuclei most significantly compared to native BP. Results are plotted as mean±standard deviation. Groups not connected by the same letter are significantly different, p<0.05 (n=6 per group).
Figure 9:
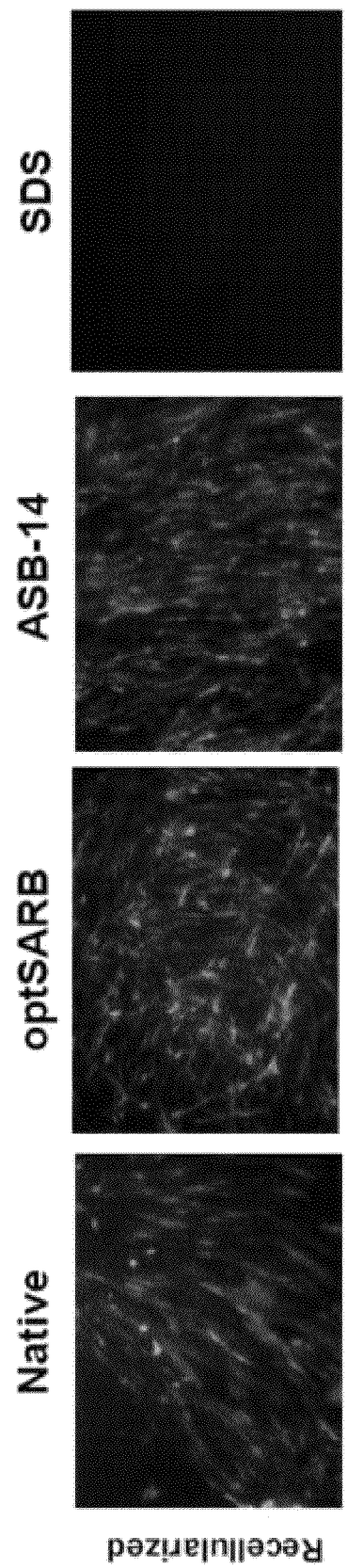
FIG. 9 illustrates fluorescence appearance of bovine pericardium (BP) recellularized with eGFP transfected human mesenchymal stem cells (hMSC). Native group is composed of untreated BP, optSARB (100 mM DTT plus 100 mM KCl) group is treated for removal of water-soluble antigens only using the solubility methods described in this patent application, ASB-14 group comprises both removal of water-soluble antigens (using optSARB) plus lipid-soluble antigens using ASB-14 as described in the present methods, SDS group is treated with 1% SDS which represents the current most commonly utilized literature control method for decellularization of xenogeneic tissue. Note that recellularization efficiency, as demonstrated by presence of eGFP-expressing hMSCs is unchanged between the native, optSARB and ASB-14 groups. In comparison, SDS group is incapable of supporting recellularization with eGFP labeled hMSCs (note complete absence of green fluorescence).

All two-step AR treatments significantly reduced the number of nuclei per HPF compared to native BP (107.42±21.95) (p<0.0001) (FIG. 8). Use of opt SARB containing no additional additive (14.81±23.44) or 1% (w/v) ASB-14 (3.81±6.47), or 1% (w/v) SDS in BARB (0.75±1.11), significantly reduced residual nuclei per HPF in BP-AR compared to 8 M urea and 2 M thiourea in opt SARB (67.56±27.27) (p<0.0001). Moreover, two-step AR using 1% (w/v) ASB-14 in opt SARB reduced residual nuclei per HPF to a similar degree to 1% (w/v) SDS in BARB. No statistically significant correlation was observed between residual nuclei counts per HPF and the normalized residual lipophilic antigenicity ratio of BP-AR following two-step AR (p=0.2740, R2=0.5270).

Immunohistochemistry.

Immunohistochemical staining revealed the presence of α-gal and MHC I antigens in native BP and BP-AR using opt SARB alone (FIG. 7). Low levels of α-gal and MHC I antigens localized to vascular structures were observed in BP-AR generated with 8 M urea and 2 M thiourea in opt SARB. Although no α-gal antigens were detected in BP-AR using 1% (w/v) SDS in BARB, a low level of MHC I antigens was observed. No detectable α-gal and MHC I antigens were found in BP-AR treated with 1% (w/v) ASB-14 in opt SARB or the negative primary antibody controls.

Discussion

There were four objectives to this study: (i) to determine if solubilization of one protein subset affects the residual antigenicity of a second protein subset (i.e., is residual lipophilic antigenicity reduced with hydrophile solubilization, or is residual hydrophilic antigenicity reduced with lipophile solubilization?); (ii) to determine whether a two-step sequential, differential protein solubilization AR strategy (hydrophile solubilization, followed by lipophile solubilization) reduces xenogeneic tissue antigenicity beyond that achieved by a one-step AR method (hydrophile solubilization alone) or the positive literature control (decellularization with 1% (w/v) SDS); (iii) to identify which of the tested lipophile solubilizing factors most effectively reduce residual lipophilic antigenicity of BP-AR in a two-step AR strategy; and (iv) to assess whether two-step sequential, differential solubilization-based AR methods adversely affect biomaterial structure-function properties, defined as uniaxial tensile properties and ECM structure and composition. We demonstrate that: (i) promotion of hydrophile or lipophile solubilization does not significantly alter residual lipophilic or hydrophilic antigenicity, respectively; (ii) promotion of hydrophile solubilization, followed by lipophile solubilization, in a two-step sequential, differential AR procedure enhances the removal of antigens from intact BP beyond that achieved using a one-step AR method; and (iii) 1% (w/v) ASB-14 enhances the removal of lipophilic antigens from BP, eliminating the two most critical known barriers to xenotransplantation (a-gal and MHC I), without compromising biomaterial structure-function properties.

Previously, we reported that hydrophile solubilization using a reducing agent and salt (opt SARB) enhances removal of hydrophilic antigens from BP [Wong, et al., *Biomaterials* (2011) 32:8129-38]. In the current study, we demonstrate that hydrophile solubilization has no effect on the removal of lipophilic antigens from BP. Additionally, we show that application of lipophile solubilization as a second AR step has no effect in further reducing residual hydrophilic antigenicity of BP following one-step AR. Furthermore, the 75% reduction in residual hydrophilic antigenicity observed with opt SARB compared to 1% (w/v) SDS is comparable to our previously published results for residual hydrophilic antigenicity observed with opt SARB compared to 0.1% (w/v) SDS [Wong, et al., *Biomaterials* (2011) 32:8129-38]. This suggests that the increase in concentration of SDS from 0.1% (w/v) to 1% (w/v) does not remove markedly more hydrophilic antigens. In sum, these findings are in agreement with the observation that protein extraction from homogenized tissue can only occur into a solution in which the particular protein subset of interest is soluble [Cordwell, *Methods Mol Biol* (2008) 424:139-46]. Therefore, removal of antigenic proteins from intact tissue is heavily dependent on the ability of the AR buffer to effectively solubilize the protein antigen subset(s) of interest.

Persistence of lipophilic antigens following one-step AR underscores the need for lipophile solubilization in a sequential AR strategy. Incorporation of lipophile solubilizing factors into a second AR step facilitates a significant reduction in the residual lipophilic antigenicity of BP-AR compared to hydrophile solubilization alone (opt SARB alone). Additionally, lipophile solubilization reduces residual lipophilic antigenicity of BP-AR to a degree comparable to (Griffiths [Griffiths, et al., *Biomaterials* (2008) 29:3514-20; Griffiths, et al., *Electrophoresis* (2008) 29:4508-15] or Leimgruber [Leimgruber R M. "Extraction and solubilization of proteins for proteomic studies," In: Walker J M, editor. *The Proteomics Protocols Handbook*. Totowa: Humana Press; (2005) pp. 1-18] solutions) or beyond (Cordwell solution [Cordwell, *Methods Mol Biol* (2008) 424:139-46]) that achieved by the current most commonly used decellularization agent (1% (w/v) SDS) [Zhou, et al., *Biomaterials* (2010) 31:2549-54; Cebotari, et al., *Artif Organs* (2010) 34:206-10; Gilbert, et al., *Biomaterials* (2006) 27:3675-83]. Furthermore, use of opt SARB for hydrophile solubilization significantly reduces residual hydrophilic antigenicity compared to 1% (w/v) SDS. Consequently, a two-step sequential, differential AR strategy using opt SARB, followed by lipophile solubilization is more effective than 1% (w/v) SDS at reducing both residual hydrophilic and lipophilic antigenicity of BP-AR. Further studies will be necessary to determine if the sequence in which solubilization is promoted has any effect on the residual antigenicity of BP-AR. These findings high-light the importance of a two-step sequential, differential AR approach, consisting of hydrophile solubilization followed by lipophile solubilization, for effective reduction of residual BP antigenicity compared to a one-step AR methodology or positive decellularization control.

After validating the need for lipophile solubilization, we sought the best candidate for use in two-step AR. Cordwell solution, the only tested two-step AR treatment to significantly reduce residual lipophilic antigenicity compared to the literature control (1% (w/v) SDS), reduces the lipophilic antigenicity of BP-AR impressively—by 91%—compared to opt SARB alone, but drastically alters the gross morphological appearance of BP-AR. Assessment of the individual components of Cordwell solution revealed that chaotropes (8 M urea and 2 M thiourea) reduce residual lipophilic antigenicity—by 85%—compared to opt SARB alone. However, chaotropes were also found to be responsible for the gross morphological disruption of BP-AR observed with the entire Cordwell solution. In contrast, 1% (w/v) ASB-14 reduces residual lipophilic BP-AR antigenicity—by 60%—compared to opt SARB alone, while avoiding the detrimental changes in gross morphology of BP-AR. Additionally, lipophile solubilization using 1% (w/v) ASB-14 eliminates detection of the two most critical known barriers to xenotransplantation (α-gal and MHC I) from resultant BP-AR. The α-gal epitope is a carbohydrate moiety present on glycolipids and glycoproteins within the cell membrane [Galili, *Biochimie* (2001) 83:557-63] and the principal determinant of hyperacute rejection in discordant xenotransplants [Yang, et al., *Nat Rev Immunol* (2007) 07:519-31]. The cell surface molecule MHC I is the most ubiquitously known stimulator of both innate and adaptive xenogeneic immune responses [Yang, et al., *Nat Rev Immunol* (2007) 07:519-31; Cascalho, *Immunity* (2001) 14:437-46]. Thus, removal of these known cell membrane-associated xenoantigens is likely to be crucial in reducing recipient immune response to xenogeneic biomaterials. Conversely, persistence of α-gal and MHC I antigens in the absence of lipophile solubilization (opt SARB alone) suggests that BP-AR undergoing only one-step AR would likely be subject to a substantial immune response. Similarly, detectable α-gal and/or MHC I antigens in BP-AR generated with 8 M urea and 2 M thiourea or 1% (w/v) SDS suggest that the resultant scaffolds would be unlikely to avoid the immune response. At first glance, these immunohistochemical findings appear to run counter to the Western blot findings when, in fact, it is likely that they are complementary. The rabbit serum used to assess residual lipophilic antigenicity of BP-AR via Western blot comprises polyclonal antibodies to a broad range of antigens, representing the global lipophilic antigenicity of BP-AR. Immunohistochemical analysis of an individual known antigen using a monoclonal antibody represents a semi-quantitative assessment of residual antigenicity for a specific epitope. Since removal of individual antigens is dependent on their solubility in the AR solution used, it is conceivable for a large proportion of an individual antigen to be removed while global antigenicity is minimally affected or a small proportion of an individual antigen be removed while global antigenicity is significantly reduced. Additional studies will be necessary to determine if this potential mechanism accurately accounts for the observed discrepancy between our Western blot and immunohistochemistry results. Furthermore, future in vivo studies will be crucial in determining what level of xenogeneic scaffold residual antigenicity (including insoluble components) is compatible with development of immune tolerance upon implantation, both for the presented small animal model and ultimately in human patients. Nonetheless, the ability of 1% (w/v) ASB-14 to significantly reduce residual lipophilic antigenicity and eliminate cell membrane-associated xenoantigens known to facilitate immune rejection of xenogeneic tissue makes it a strong candidate for lipophile solubilization in two-step AR, warranting further characterization of structure-function properties for the resultant scaffold.

A successful two-step AR strategy must preserve xenogeneic scaffold structure-function properties. Use of 1% (w/v) ASB-14 for lipophile solubilization resulted in BP-AR with tensile properties, ECM composition and ECM organization indistinguishable from native BP. This is likely attributed to the ability of zwitterionic detergents such as ASB-14 to accomplish lipophile solubilization while maintaining native protein conformation [Nagy, et al., "Sample preparation for 2D electrophoresis and CE-based proteomics," *Sample preparation in biological mass spectrometry*. New York: Springer; (2011) pp. 41-60]. The presence of both hydrophilic and hydrophobic domains on detergent molecules enables their incorporation into the cell membrane, leading to bilayer destabilization and fragmentation and, ultimately, the solubilization of resultant detergent-protein complexes [le Maire, et al., *Biochim Biophys Acta* (2000) 1508:86-111]. In contrast, chaotropes such as 8 M urea and 2 M thiourea have been reported to achieve lipophile solubilization through protein denaturation [Frank, et al., *J Chem Phys* (1968) 48:4746-57; Hua, et al., *Proc Natl Acad Sci USA* (2008) 105:16928-33; Gordon, et al., *Biochemistry* (1963) 2:47-57]. Denaturation, but not loss, of collagen may account for disrupted collagen fiber organization, and subsequent gross thickening, increased water content and altered tensile properties of BP-AR following AR using 8 M urea and 2 M thiourea [Hua, et al., *Proc Natl Acad Sci USA* (2008) 105:16928-33; Gordon, et al., *Biochemistry* (1963) 2:47-57]. Additionally, elastin denaturation, manifested as a loss of elastin organization and content, may also contribute to the unacceptable loss of structure-function properties in chaotrope-treated BP-AR. In aortic valve leaflets, elastin fibers maintain leaflet structure-function properties by facilitating changes in collagen fiber configuration throughout the cardiac cycle [Vesely, *J Biomech* (1997) 31:115-23]. By compromising elastin-mediated pre-stress on the collagen fibers in BP-AR, 8 M urea and 2 M thiourea may adversely alter collagen fiber organization and, ultimately, the structure-function properties of BP-AR. Similarly, lipophile solubilization using 1% (w/v) SDS was also found to result in significant alterations to biomaterial structure-function properties. Increasing concentrations of SDS increases collagen swelling [Krejci, *Int J Cosmetic Sci* (2007) 29:121-9; Henriquez, Macromolecules (1994) 27:6834-40] due to destabilization of the triple helical domain [Samouillan, et al., *J Biomed Mater Res* (1999) 46:531-8]. Thus, SDS-mediated disruption of collagen architecture and removal of elastin fibers may explain the noticeable gross tissue thickening and increased water content observed in the resultant BP-AR. The structural and compositional alterations associated with 1% (w/v) SDS may account for tensile properties trending lower than those of native BP, although this finding failed to reach statistical significance. Amongst the antigen removal agents tested for two-step AR, 1% (w/v) ASB-14 demonstrates the most promise in xenogeneic scaffold generation by achieving significant reduction in residual lipophilic antigenicity while maintaining structure-function properties comparable to native BP. Future studies will be necessary to determine the compatibility of scaffolds generated using a two-step AR process (opt SARB, followed by 1% (w/v) ASB-14 in opt SARB) with recellularization, in vivo physiological function and in vivo recipient immune response.

Previously, we questioned the appropriateness of using residual nuclei counts as the sole indicator of sufficient AR after demonstrating that overall residual hydrophilic antigenicity does not correlate significantly with residual nuclei counts [Wong, et al., *Biomaterials* (2011) 32:8129-38]. The lack of significant correlation was not surprising as one would not expect one-step AR, solely promoting hydrophile solubilization, to efficiently solubilize the nuclear membrane. Thus, residual nuclei counts were expected to better represent residual lipophilic antigenicity of BP-AR. While lipophile solubilization reduces residual nuclei counts in BP-AR significantly, no significant correlation was found between residual lipophilic antigenicity and residual nuclei counts. As residual nuclei counts merely serve as an indicator of DNA that persists within the tissue, they do not reflect the level of either residual hydrophilic or lipophilic antigenicity within the biomaterial. Thus, assessment of biomaterial decellularization does not provide an accurate assessment of AR from xenogeneic biomaterials.

Conclusions

By targeting the solubilization of multiple protein subsets using a sequential, differential approach (first removing hydrophiles, then lipophiles), biomaterial antigenicity can be more efficiently reduced compared to a single solution that only solubilizes one protein antigen subset. Sequential application of opt SARB, followed by 1% (w/v) ASB-14 in opt SARB, to BP reduces residual hydrophilic antigenicity by an additional 75% compared to that achieved by 1% (w/v) SDS in BARB and residual lipophilic antigenicity by an additional 60% compared to that achieved by opt SARB alone. Excitingly, this two-step AR method eliminates the presence of the two most critical known barriers to xenotransplantation (α-gal and MHC I) without significantly compromising structure-function properties of the resultant scaffold. In sum, these findings illustrate that facilitating the sequential, differential solubilization of hydrophiles and lipophiles in a two-step AR strategy, utilizing opt SARB followed by 1% (w/v) ASB-14 in opt SARB, (i) significantly reduces the residual hydrophilic and lipophilic antigenicity of BP— AR, and (ii) maintains biomaterial structure-function properties. Beyond the generation of BP-derived scaffolds for heart valve tissue engineering, application of this stepwise AR strategy to other tissues or organs of the body represents a more efficient alternative to decellularization for the generation of immune system-tolerant, tissue engineering scaffolds from xenogeneic tissues.

Example 2

In Vivo Implantation of Decellularized Tissue

Results

Figure 10:
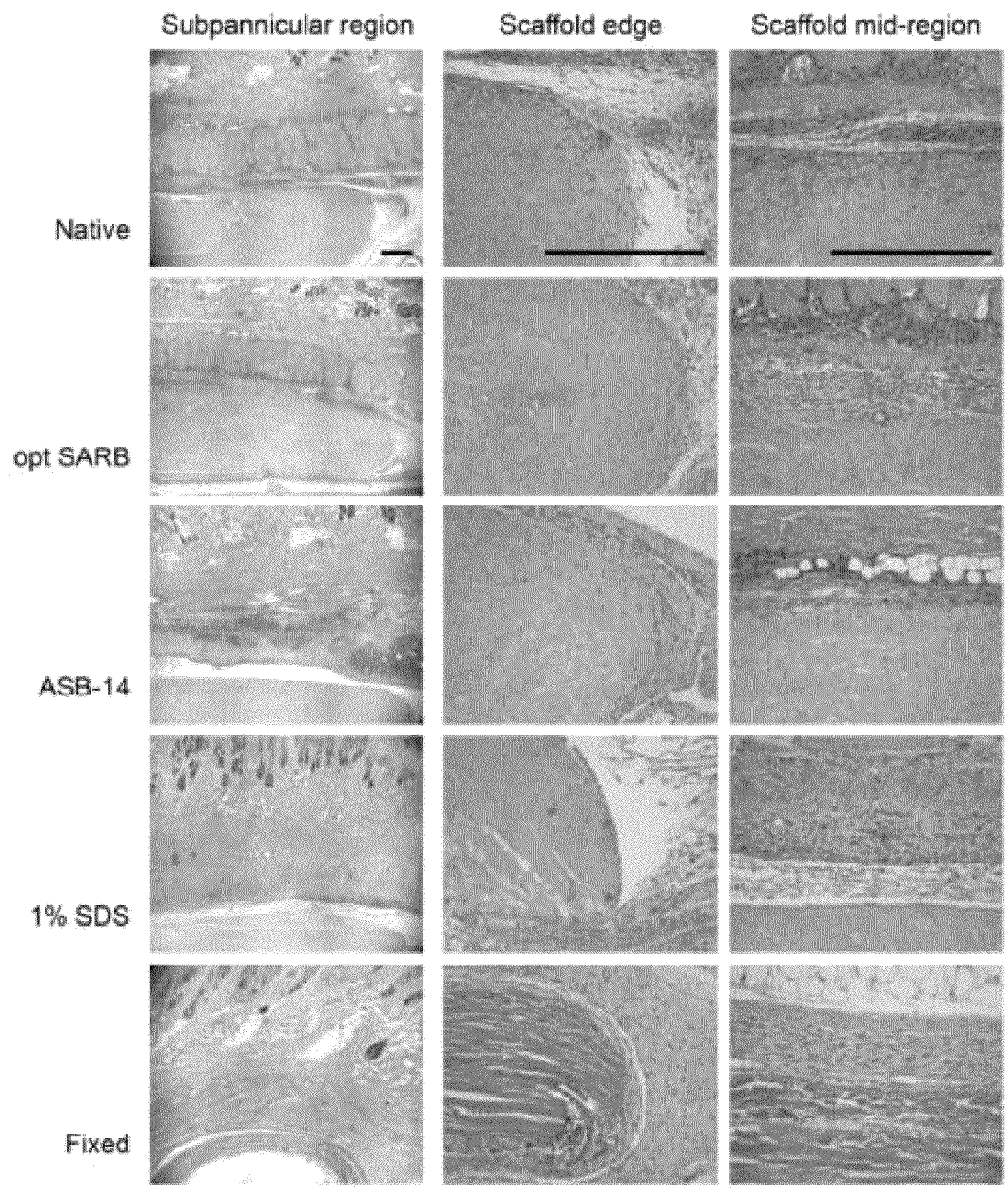
FIG. 10 illustrates histological analysis of bovine pericardium (BP) explants following one week of implantation in New Zealand White rabbits. Native group consists of native BP, optSARB group is treated for removal of water-soluble antigens only using the solubility methods described in this patent application, ASB-14 group comprises both removal of water-soluble antigens (using optSARB) plus lipid-soluble antigens using ASB-14 as described in the present methods, SDS group is treated with 1% SDS which represents the current most commonly utilized literature control method for decellularization of xenogeneic tissue, fixed group consists of commercially available (St Jude medical) glutaraldehyde-fixed BP which is a currently licensed FDP approved heart valve and vessel patch material. All groups demonstrate mild to moderate inflammatory cell infiltration. Scale bar represents 500 μm.

One week after subpannicular implantation, a non-specific inflammatory response following the surgery was observed toward all bovine pericardium (BP) scaffolds. No dramatic differences in this response were observed between treatment groups (FIG. 10).

Figure 11:
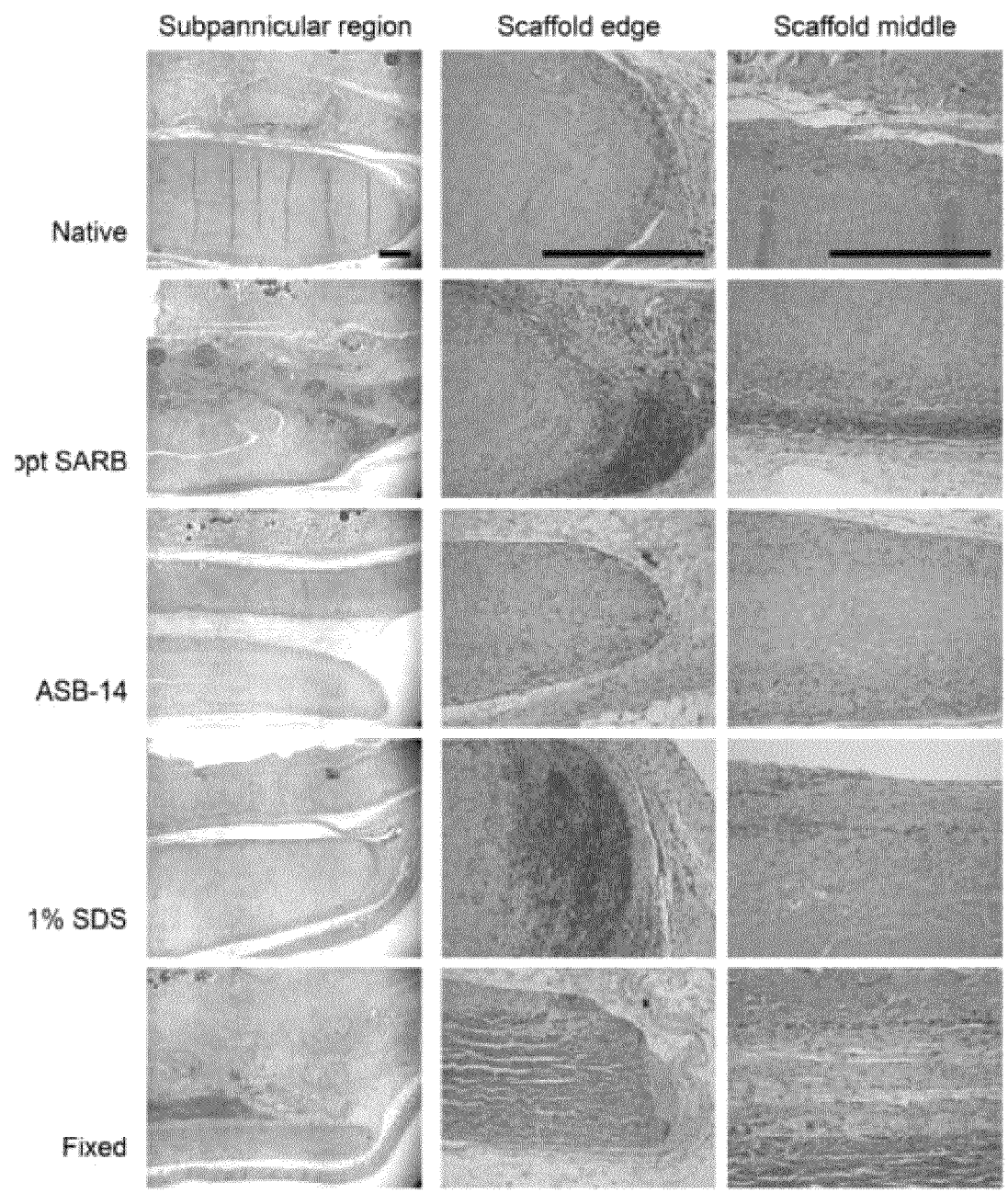
FIG. 11 illustrates histological analysis of bovine pericardium (BP) explants following six weeks of implantation in New Zealand White rabbits. Native group consists of native BP, optSARB group is treated for removal of water-soluble antigens only using the solubility methods described in this patent application, ASB-14 group comprises both removal of water-soluble antigens (using optSARB) plus lipid-soluble antigens using ASB-14 as described in the present methods, SDS group is treated with 1% SDS which represents the current most commonly utilized literature control method for decellularization of xenogeneic tissue, fixed group consists of commercially available (St Jude medical) glutaraldehyde-fixed BP which is a currently licensed FDP approved heart valve and vessel patch material. A minimal amount of small mononuclear cells (MNCs) are observed in the subdermal, subpannicular, and peri-scaffold regions associated with ASB-14 treated BP-AR. A mild level of small MNCs is associated with SDS-decellularized BP. A moderate amount of small MNCs were found with fixed BP or native BP. A severe level of small MNCs, including formation of lymphoid follicles, is associated with opt SARB alone-treated BP-AR. Stepwise antigen removal using ASB-14 decreases the amount of MNCs in the peri-scaffold region compared to native BP, opt SARB-treated BP, SDS-decellularized BP, or fixed BP. Little to no fibrous encapsulation is seen with ASB-14 treated BP-AR, opt SARB-treated BP-AR, or native BP. Conversely, notable fibrous encapsulation is associated with SDS-decellularized BP or fixed BP. Stepwise antigen removal using ASB-14 is associated with less fibrous encapsulation than SDS-decellularized BP or fixed BP. Finally, marked cellular ingrowth is observed with ASB-14 treated BP-AR or opt SARB-treated BP-AR. However, minimal cellular ingrowth is associated with SDS-decellularized BP or fixed BP. Stepwise antigen removal using ASB-14 supports robust cellular repopulation of BP-AR. In contrast to clinically-approved fixed BP or SDS-decellularized BP: (1) Less small MNCs are elicited to respond to ASB-14 treated BP-AR at six weeks following implantation. (2) ASB-14 treated BP-AR has not been walled off by fibrous encapsulation in the rabbit. (3) ASB-14 treated BP-AR is able to support recellularization with host cells. Taken together, these findings suggest indicate that stepwise, solubilization-based antigen removal using optSARB followed by ASB-14 reduces the in vivo immune response towards BP-AR compared to native BP; BP following one-step, solubilization-based antigen removal (opt SARB); SDS-decellularized BP; and clinically approved gluraraldehyde-fixed BP. Scale bar represents 500 μm.
Figure 12:
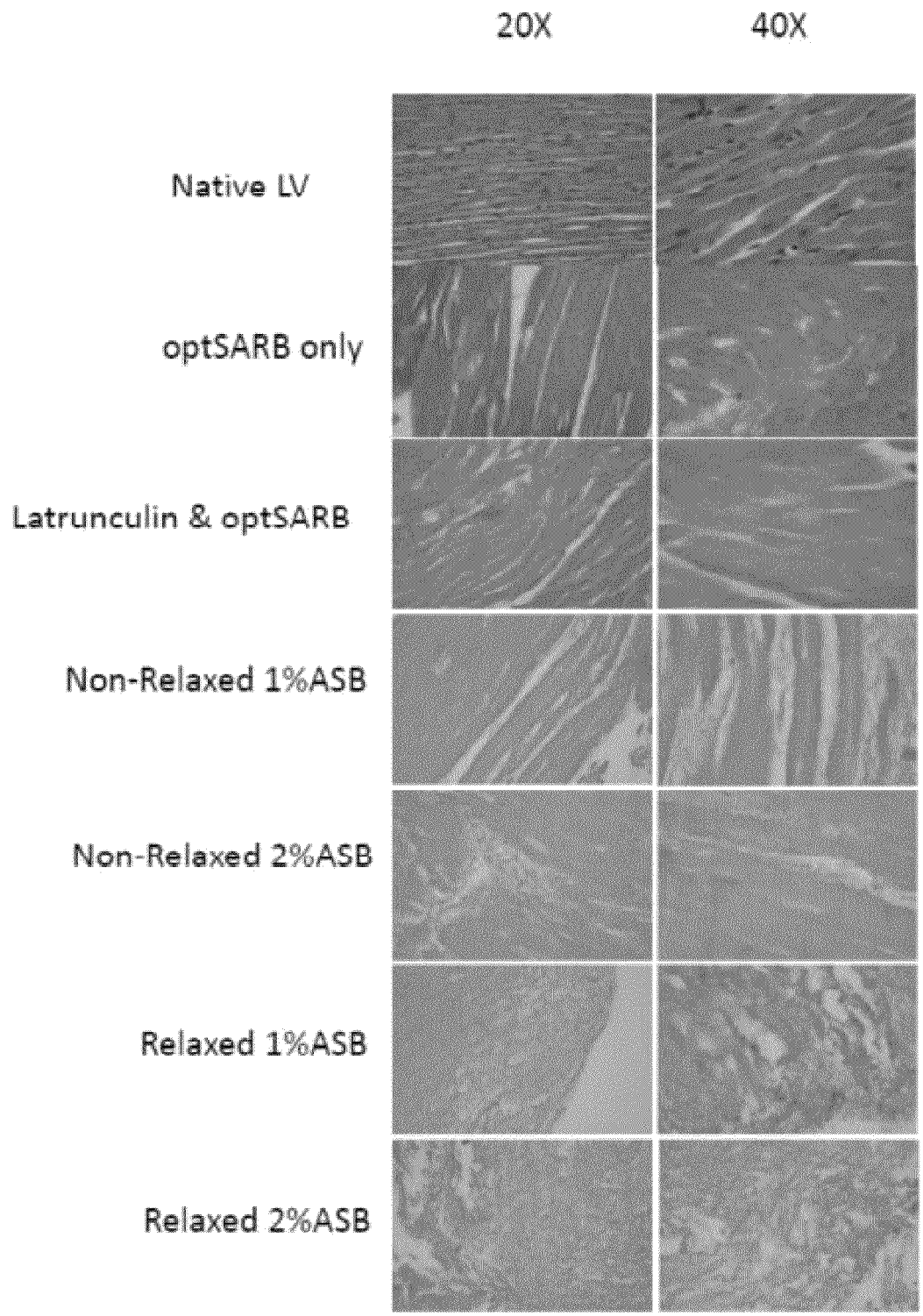
FIG. 12 illustrates Histologic sections of heart muscle scaffolds generated using the protocols described herein. Top Row: Native LV—native unprocessed rat left ventricular (LV) heart muscle tissue. Second Row: Following hydrophilic antigen removal alone using solubilization antigen removal buffer (SARB, containing DTT and KCl) for 2 days, cardiomyocytes show evidence of mild cytoplasmic and nuclear vacuolation. Third Row: Addition of Latrunculin to SARB protocol results in increased coalescing areas of cytoplasmic vacuolation, mild disruption of sarcomeric structure and almost complete removal of nuclei. Fourth and Fifth Rows: Addition of ASB-14 (hydrophobic solubilization) prior to application of Latrunculin/SARB results in complete removal of some cardiomyocytes while retaining normal structure of the extracellular matrix (ECM) in these regions, although some cardiomyocytes remain. Sixth Row: Relaxation of the myocardium prior to application of the 1% ASB-14, Latrunculin, SARB sarcomere disassembly and solubilization protocol, results in a significant increase in the proportion of cardiomyocytes which are completely removed by the protocol, again ECM structure is retained, although some cardiomyocytes remain. Seventh Row: Relaxation of the myocardium followed by application of 2% ASB-14, Latrunculin and SARB results in complete removal of all cardiomyocytes and nuclei from the material. ECM matrix structure is completely retained.
Figure 13:
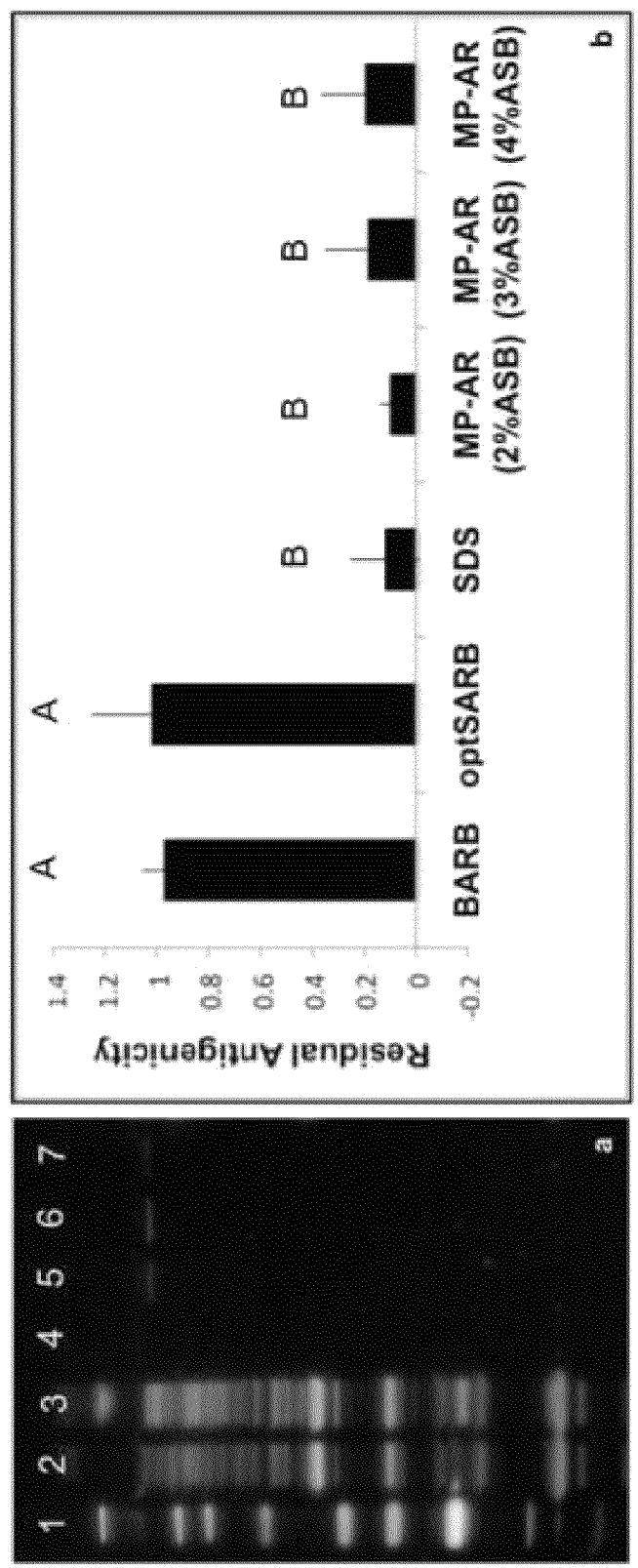
FIG. 13 illustrates reduced antigenicity of left ventricular myocardial tissue. Biomaterial residual antigenicity was assessed using Western blot methods published in the scientific literature and described herein. a; Western blot of residual antigens extracted from myocardial patches (MP) probed using mouse anti-rat LV poly-polyclonal serum. Lanes: 1; MagicMark Protein Ladder (Invitrogen), 2; BARB native tissue control, 3; optSARB, 4; 1% SDS, 5; myocardial patch following antigen removal (MP-AR) as described in the current invention (Step 1 for Water-Soluble antigens: LatrunculinB, KCl, KI; followed by Step 2 for Lipid-Soluble antigens: 2% ASB in optSARB), 6; MP-AR using 3% ASB in optSARB in the second step of AR, 7; MP-AR using 4% ASB in optSARB, b; Densitometry analysis for residual antigenicity. Results displayed as means±standard deviation. Our antigen removal approach (MP-AR) results in removal of >90% of antigens from the myocardial patch. Groups not connected by the same letter are significantly different, p<0.01 (n=6 per group).

Six weeks after subpannicular implantation, the in vivo immune response of New Zealand White rabbits towards BP following stepwise, solubilization-based antigen removal using opt SARB, followed by ASB-14 is markedly less than that towards native BP; BP following one-step, solubilization-based antigen removal (opt SARB); BP decellularized with 1% (w/v) SDS; and even the current clinically accepted gold standard glutaraldehyde-fixed BP (FIG. 11).

A minimal amount of small mononuclear cells (MNCs) are observed in the subdermal, subpannicular, and peri-scaffold regions associated with ASB-14 treated BP-AR. A mild level of small MNCs is associated with SDS-decellularized BP. A moderate amount of small MNCs were found with fixed BP or native BP. A severe level of small MNCs, including formation of lymphoid follicles, is associated with opt SARB alone-treated BP-AR. Stepwise antigen removal using ASB-14 decreases the amount of MNCs in the peri-scaffold region compared to native BP, opt SARB-treated BP, SDS-decellularized BP, or fixed BP.

Little to no fibrous encapsulation is seen with ASB-14 treated BP-AR, opt SARB-treated BP-AR, or native BP. Conversely, notable fibrous encapsulation is associated with SDS-decellularized BP or fixed BP. Stepwise antigen removal using ASB-14 is associated with less fibrous encapsulation than SDS-decellularized BP or fixed BP.

Finally, marked cellular ingrowth is observed with ASB-14 treated BP-AR or opt SARB-treated BP-AR. However, minimal cellular ingrowth is associated with SDS-decellularized BP or fixed BP. Stepwise antigen removal using ASB-14 supports robust cellular repopulation of BP-AR.

Conclusions

We demonstrate herein that stepwise, solubilization-based antigen removal using ASB-14 significantly reduces the global residual antigenicity of BP-AR and eliminates the presence of α-gal and MHC I—the two most critical barriers to xenotransplantation.

This example provides, for the first time, in vivo observations which further validate our in vitro findings for a significant reduction of BP residual antigenicity with stepwise, solubilization-based antigen removal using ASB-14. In contrast to clinically-approved fixed BP or SDS-decellularized BP: (1) Less small MNCs are elicited to respond to ASB-14 treated BP-AR at six weeks following implantation. (2) ASB-14 treated BP-AR has not been walled off by fibrous encapsulation in the rabbit. (3) ASB-14 treated BP-AR is able to support recellularization with host cells. Taken together, these findings suggest that stepwise, solubilization-based antigen removal using ASB-14 reduces the in vivo immune response towards BP-AR compared to native BP; BP following one-step, solubilization-based antigen removal (opt SARB); SDS-decellularized BP; and fixed BP.

Example 3

Antigen Removal from Cardiac Muscle Tissue

Materials and Methods

Myocardial Patch (MP) Isolation.

Whole hearts were isolated from Fischer rats (CDF®, CRL, Kingston, N.Y.) being euthanized from other non-cardiac studies, perfused with heparin via antegrade coronary perfusion and stored in storage solution (DMEM with 15% DMSO v/v) at −80° C. Hearts are defrosted at room temperature and blood removed by antegrade coronary perfusion with 4° C. heparinized PBS (10 IU/ml). MPs are prepared as follows: The left ventricle (LV) is isolated and two 4 mm thick short axis LV slices cut from base to apex. Each LV slice is cut longitudinally through the LV free wall between the papillary muscles. A 3.5 mm biopsy punch (Miltex) is utilized to cut adjacent cylindrical pieces of LV tissue. This approach allows for the generation of 6 identical LV myocardial patches (MP) from each LV slice (total of 12 MPs per heart). MPs are placed in Relaxing Solution comprising of 120 mM KCl, 4 mM $MgCl_2$, 4 mM EGTA, 20 mM TrisHCl pH 7.5, 5.88 mM NaATP, 0.5 mM Pefabloc, 1% Antibiotic Antimycotic Solution (AAS; Sigma) on ice upon isolation until further processing. MPs are patted dry twice and their wet weights recorded (approximately 20 mg per patch).

Generation of Mouse Anti-Rat LV Anti-Serum.

Murine sera generation was conducted following UC Davis institutional procedures and was covered by IACUC #15064. Isolated adult Fischer rat LV's (n=6) were homogenized and injected subcutaneously into C57BL/6 mice (n=6) on days 0, 14, 28, 42, 56 and 72. Serum was collected at days 0, 14, 28, 42, 56, 72, and 84, and stored at −80° C.

Antigen Removal (AR) Procedure.

All steps of the AR protocol are performed at 125 rpm and at RT or 4° C. unless otherwise stated. AR procedure for Water-Soluble antigens (WSA) and Lipid-Soluble antigens (LSA) involves incubating MPs in any given AR additive such as the examples shown in (Table 1) for 1-3 days, depending on the additive used. Anatomically adjacent MP pieces are subjected to 1 min incubations and serve as negative AR controls. Following nucleic acid digestion for 24 h and washout for 48 h, MPs following AR (designated as MP-AR) are stored in 15% DMSO in DMEM at −80° C.

TABLE 1

ANTIGEN REMOVAL ADDITIVES
FOR EACH PROTEIN CLASS AND LEVELS USED

| AR Step | Additive | [Function/Levels] |
|---|---|---|
| Water-Soluble proteins | BARB (Basic AR Buffer); 0.5 mM Pefabloc (Roche) and 1% AAS in 10 mM Tris-HCl, pH 8.0 | Hypotonic solution containing protease inhibitors and antibiotic/antimycotic agent; Cell lysis |
| Water-Soluble proteins | optSARB (optimized Solubilizing Antigen Removal Buffer; 100 mM DTT, 2 mM $MgCl_2$, 100 mM KCl in BARB) | BARB corrected for isotonic/physiologic salt concentration; protein/antigen solubilization with use of reducing reagent (DTT) |
| Actin Depolymerization | Cytochalasin D in organic solvent (such as DMSO) or high glucose DMEM | 0, 100 nM, 1 µM, 10 µM |

TABLE 1-continued

ANTIGEN REMOVAL ADDITIVES
FOR EACH PROTEIN CLASS AND LEVELS USED

| AR Step | Additive | [Function/Levels] |
|---|---|---|
| Actin Depolymerization | Latrunculin B in high glucose DMEM | 0, 50 nM, 100 nM, 200 nM |
| Actin Depolymerization | Mycalolide B in organic solvent (such as DMSO) or high glucose DMEM | 0, 100 nM, 1 μM, 10 μM |
| Actin Depolymerization | Swinholide A in organic solvent (such as DMSO) | 0, 100 nM, 1 μM, 10 μM |
| Cardiac Myosin solubilization | KCl in aqueous buffer containing protease inhibitors and antibiotics | 400 mM, 500 mM, 600 mM, 800 mM |
| Cardiac Titin solubilization | KI in aqueous buffer containing protease inhibitors and antibiotics | 400 mM, 600 mM, 800 mM, 1M |
| Lipid-Soluble proteins | Amidosulfobetaine 14 (ASB-14) | Sulfobetaine detergent. 0, 1%, 2%, 3%, 4%, 5% |
| Lipid-Soluble proteins | ASB-16 | Sulfobetaine detergent. 0, 0.05%, 0.1%, 1%, 2% |
| Lipid-Soluble proteins | Sulfobetaine 3-12 (SB 3-12) | Sulfobetaine Detergent. 0, 0.1%, 0.2%, 0.5%, 2% |
| Lipid-Soluble proteins | SB 3-14 | Sulfobetaine Detergent. 0, 0.1%, 1%, 2%, 4%, 5% |
| [Decellularization/ Literature control] | 1% SDS (w/v) | Strong anionic detergent, literature control |

Example of Water-Soluble and Lipid-Soluble Antigen Removal on a Myocardial Patch.

All steps are performed at 125 rpm at RT unless otherwise stated. Following MP isolation and recording of wet weights as described above, MPs are incubated in relaxing solution for 2×15 min at 125 rpm, at 4° C. MPs are then incubated in the lipid-soluble antigen removal solution comprising of 2% ASB in optimized Standard Antigen Removal Buffer (opt-SARB; 0.5 mM Pefabloc and 1% AAS in 10 mM Tris-HCl, pH 8.0, 100 mM DTT, 2 mM MgCl$_2$, 100 mM KCl) for 2 days at 4° C., with one addition of fresh solution after 24 hrs. MPs are then washed 2×15 min in optSARB, before proceeding with sarcomere disassembly using actin depolymerization followed by solubilization of sarcomeric components and associated water-soluble antigens. Specifically, MPs are incubated for 2 h at 37° C. in 50 nM Latrunculin B in high-glucose DMEM, washed 2×15 min in optSARB, incubated for 2 h in 0.6 M KCl containing 0.5 mM Pefabloc and 1% AAS, washed for 2×15 min in optSARB, incubated for 2 h in 1.0 M KI containing 0.5 mM Pefabloc and 1% AAS, after which they are left in optSARB at 4° C. overnight.

The following day KCl and KI incubations are repeated as described above, with 2×15 min optSARB washes in between them, followed by optSARB wash overnight at 4° C. The next day fresh optSARB is applied to the MP-AR scaffolds for 24 h at 4° C. Following this, MP-AR scaffolds are incubated for 24 h at 4° C. with Nuclease solution (2.5 Kunitz units/mL DNAse I, 7.5 Kunitz units/mL RNAse A, 1% AAS, 0.15 M NaCl, 5 mM MgCl$_2$-6H$_2$O in 10 mM Tris-HCl, pH 7.6). Then, they are washed for 48 h in washing solution (0.5 mM Pefabloc and 1% AAS in 1×TBS) which is changed to fresh solution 1/day and lastly, the scaffolds are stored at 80° C. in 15% v/v DMSO in high glucose DMEM storage solution.

Assessment of Residual Antigenicity in MP-AR Samples.

MP-AR samples and controls are minced and residual proteins extracted. Extracted proteins are subjected to one-dimensional electrophoresis (1-DE) and Western blot (WB) probed with mouse anti-rat native LV poly-polyclonal antiserum diluted 1:100 and assessed for IgG positivity with 1:10,000 hrp-conjugated anti-mouse light chain specific secondary antibody (Jackson Immunoresearch). Western blots are imaged using Fluor Chem Xplor CCD bioimaging system and AlphaView image acquisition and analysis software (Alpha Innotech Corp). Densitometry is used to quantify banding pattern intensity. Residual antigenicity of MP-AR is defined as the ratio of banding intensity for extracts following 2 d of AR compared the 1 min AR controls. Overall residual antigenicity for each AR protocol is calculated with respect to the level of antigens present in negative control (examples shown in Table 1).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of removing immunogenic antigens from a tissue, comprising:
    a) solubilizing water-soluble antigens in the tissue by contacting the tissue with a first solution comprising a first buffering agent, a first reducing agent, a first protease inhibitor, and one or more salts suitable for maintaining protein solubility, wherein the first solution is substantially free of an amphiphile, such that the water-soluble antigens are dissolved in the first solution;
    b) separating the tissue from the solubilized water-soluble antigens in the first solution;
    c) solubilizing lipid-soluble antigens in the tissue by contacting the tissue with a second solution comprising a second buffering agent, a second reducing agent, a second protease inhibitor, one or more salts suitable for maintaining protein solubility and an amphiphile, such that the lipid-soluble antigens are dissolved in the second solution; and
    d) separating the tissue from the solubilized lipid-soluble antigens in the second solution; thereby removing immunogenic antigens from the tissue.

2. The method of claim 1, wherein one or more of the steps are repeated.

3. The method of claim 1, wherein the immunogenic antigens are selected from the group consisting of protein antigens, lipid antigens and carbohydrate antigens.

4. The method of claim 1, wherein the first buffering agent maintains a pH in the range of about 4-11.

5. The method of claim 1, wherein the one or more salts of the first solution comprise a metal halide salt.

6. The method of claim 1, wherein the first reducing agent is selected from the group consisting of Tributylphosphine (TBP), beta mercaptoethanol, 2-mercaptoethylamine, tris(2-carboxyethyl)phosphine (TCEP), cysteine-HCl, and dithiothreitol (DTT).

7. The method of claim 1, wherein the water-soluble antigens are solubilized in the first solution that further comprises a chelation agent.

8. The method of claim 1, wherein the water-soluble antigens are solubilized in the first solution comprising Tris-HCl, dithiothreitol (DTT), the first protease inhibitor, and KCl.

9. The method of claim 1, wherein the amphiphile of the second solution is a sulfobetaine.

10. The method of claim 9, wherein the sulfobetaine is selected from the group consisting of 3-[N,N-Dimethyl(3-myristoylaminopropyl)ammonio]propanesulfonate (amidosulfobetaine-14; ASB-14); amidosulfobetaine-16 (ASB-16); 4-n-Octylbenzoylamido-propyl-dimethylammonio sulfobetaine (ASB-C8Ø); 3-(N,N-Dimethyloctylammonio) propanesulfonate inner salt (SB3-8); N-Decyl-N,N-dimethyl-3-ammonio-1-propanesulfonate (SB 3-10), N-Decyl-N,N-dimethyl-3-ammonio-1-propanesulfonate (SB 3-12), N-Tetradecyl-N,N-dimethyl-3-ammonio-1-propanesulfonate (SB 3-14); 3-(N,N-Dimethylpalmitylammonio) propanesulfonate (SB3-16); 3-(N,N-Dimethyloctadecylammonio) propanesulfonate (SB3-18); 3-(1-Pyridinio)-1-propanesulfonate (NDSB-201); 3-(Benzyldimethylammonio) propanesulfonate (NDSB-256); NDSB-211, NDSB-195, NDSB-221; 3-[(3-Cholamidopropyl)dimethylammonio]-1-propanesulfonate (CHAPS), 3-[(3-Cholamidopropyl)dimethylammonio]-2-hydroxy-1-propanesulfonate (CHAPSO), and mixtures thereof.

11. The method of claim 1, wherein the lipid-soluble antigens are solubilized in the second solution comprising Tris-HCl, dithiothreitol (DTT), the second protease inhibitor, KCl and ASB-14.

12. The method of claim 1, wherein the method yields a substantially intact extracellular matrix (ECM) compatible with viable cell repopulation.

13. The method of claim 12, further comprising repopulating the ECM with live cells.

14. The method of claim 1, wherein the tissue is epithelial tissue, endothelial tissue, muscle tissue, or connective tissue.

15. The method of claim 1, wherein the tissue is selected from the group consisting of cardiac muscle tissue, striated or skeletal muscle tissue, or smooth muscle tissue, heart, pericardium, heart valve, vessel, vascular conduit, artery, vein, skin, dermis, pericardium, dura, intestinal submucosa, ligament, tendon, bone, cartilage, ureter, urinary bladder, kidney, skin, lung, liver, and umbilical cord.

16. The method of claim 1, wherein the tissue is an intact tissue.

17. The method of claim 1, wherein the tissue is within or a part of an intact organ.

18. The method of claim 1, wherein the tissue is intact tissue, the method comprising:
a) solubilizing water-soluble antigens in the tissue by contacting the tissue with the first solution comprising Tris-HCl, dithiothreitol (DTT), the first protease inhibitor, and KCl, wherein the first solution does not comprise an amphiphile, such that the water-soluble antigens are dissolved in the first solution;
b) separating the tissue from the solubilized water-soluble antigens in the first solution;
c) solubilizing lipid-soluble antigens in the tissue by contacting the tissue with a second solution comprising Tris-HCl, dithiothreitol (DTT), the second protease inhibitor, KCl and ASB 14, such that the lipid-soluble antigens are dissolved in the second solution; and
d) separating the tissue from the solubilized lipid-soluble antigens in the second solution; thereby removing immunogenic antigens from the intact tissue.

19. A method of removing immunogenic antigens from a tissue, comprising:
a) contacting the tissue with one or more cytoskeletal destabilizing agents;
b) solubilizing water-soluble antigens in the tissue;
c) separating the tissue from the solubilized water-soluble antigens;
d) solubilizing lipid-soluble antigens in the tissue; and
e) separating the tissue from the solubilized lipid-soluble antigens; thereby removing immunogenic antigens from the tissue.

20. The method of claim 19, wherein the one or more cytoskeletal destabilizing agents comprise one or more actin depolymerization agents.

21. The method of claim 19, wherein the one or more cytoskeletal destabilizing agents comprise one or more microtubule depolymerization or destabilizing agents.

22. A method of removing immunogenic antigens from a muscle tissue, comprising:
a) relaxing the muscle tissue in a relaxing solution comprising an energy source molecule;
b) contacting the muscle tissue with one or more cytoskeletal destabilizing agents;
c) contacting the muscle tissue with a concentrated salt solution;
d) solubilizing water-soluble antigens in the tissue;
e) separating the muscle tissue from the solubilized water-soluble antigens;
f) solubilizing lipid-soluble antigens in the tissue; and
g) separating the muscle tissue from the solubilized lipid-soluble antigens; thereby removing immunogenic antigens from the muscle tissue.

23. The method of claim 22, wherein one or more of the steps are repeated.

24. The method of claim 22, wherein the steps are performed in an order selected from the group consisting of:
i) a), b), c), d), e), f) and g);
ii) a), f), g), b), c), d) and e);
iii) a), d), e), b), c), f) and g);
iv) a), d), e), f), g), b) and c);
v) a), b), c), d), e), f), g), b), c), and e); and
vi) a), f), g), b), c), d), e), f), and g).

25. The method of claim 22, wherein the muscle tissue is cardiac muscle tissue, striated or skeletal muscle tissue, or smooth muscle tissue.

26. The method of claim 22, wherein the method comprises the step of relaxing the muscle tissue prior to contacting the tissue with one or more cytoskeletal destabilizing agents.

27. The method of claim 22, wherein the muscle tissue is relaxed in a relaxing solution comprising an energy source molecule.

28. The method of claim 27, wherein the energy source molecule is selected from the group consisting of a nucleotide 5'-triphosphate (NTP), adenosine, inosine, aspartate, glutamate, creatine phosphate, a Kreb's cycle precursor or intermediate, glucose, and dextrose.

29. The method of claim 27, wherein the energy source molecule is a Pyrophosphate (PPi) or a nucleotide 5'-triphosphate (NTP) selected from the group consisting of adenosine 5'-triphosphate (ATP), inosine 5'-triphosphate (ITP), guanidine 5'-triphosphate (GTP), cytidine 5'-triphosphate (CTP), and uridine 5'-triphosphate (UTP).

30. The method of claim 27, wherein the energy source molecule is a precursor of adenosine 5'-triphosphate (ATP).

31. The method of claim 22, wherein the relaxing solution further comprises a calcium ion chelating agent.

32. The method of claim 22, wherein the relaxing solution further comprises a permeabilization agent.

33. The method of claim 22, wherein concentrated salt solution comprises one or more salts in a concentration range from about 0.5 M to about 3.0 M.

34. The method of claim 22, wherein the concentrated salt solution comprises one or more metal halide salts.

35. The method of claim 22, wherein sarcomeric constituents are not detectable in the muscle tissue.

\* \* \* \* \*